United States Patent
Ghosh

(10) Patent No.: US 9,528,994 B2
(45) Date of Patent: Dec. 27, 2016

(54) TARGET OF THE PHOSPHOINOSITIDE 3-KINASE PATHWAY

(75) Inventor: Pradipta Ghosh, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 176 days.

(21) Appl. No.: 14/235,036

(22) PCT Filed: Jul. 25, 2012

(86) PCT No.: PCT/US2012/048206
§ 371 (c)(1),
(2), (4) Date: May 6, 2014

(87) PCT Pub. No.: WO2013/016465
PCT Pub. Date: Jan. 31, 2013

(65) Prior Publication Data
US 2014/0234872 A1 Aug. 21, 2014

Related U.S. Application Data

(60) Provisional application No. 61/511,518, filed on Jul. 25, 2011.

(51) Int. Cl.
*C07K 16/44* (2006.01)
*C07K 16/18* (2006.01)
*G01N 33/574* (2006.01)

(52) U.S. Cl.
CPC ......... *G01N 33/57496* (2013.01); *C07K 16/18* (2013.01); *C07K 16/44* (2013.01); *G01N 33/57415* (2013.01); *G01N 33/57484* (2013.01); *G01N 2440/14* (2013.01); *G01N 2800/50* (2013.01)

(58) Field of Classification Search
CPC .............. G01N 33/57496; G01N 33/57415; G01N 33/57484; G01N 2440/14; G01N 2800/50; C07K 16/18; C07K 16/44
See application file for complete search history.

(56) References Cited

U.S. PATENT DOCUMENTS

| | | | |
|---|---|---|---|
| 5,741,689 | A | 4/1998 | Dhand et al. |
| 7,183,385 | B2 | 2/2007 | Comb et al. |
| 7,306,921 | B2 | 12/2007 | Nevalainen et al. |

FOREIGN PATENT DOCUMENTS

| | | |
|---|---|---|
| WO | 94/07913 A1 | 4/1994 |
| WO | 96/25488 A1 | 8/1996 |
| WO | 2008/054597 | 5/2008 |

OTHER PUBLICATIONS

Garcia-Marcos et al. (Expression of GIV/Girdin, a metastasis-related protein, predicts patient survival in colon cancer, FASEB Journal 25: 590-599 (Feb. 2011)).*
International Search Report and Written Opinion received for PCT Patent Application No. PCT/US2012/048206, mailed on Sep. 28, 2012, 7 pages.
International Preliminary Report on Patentability received for PCT Patent Application No. PCT/US2012/048206, mailed on Feb. 6, 2014, 6 pages.
Garcia-Marcos et al., 2009. "GIV is a nonreceptor GEF for G alpha i with a unique motif that regulates Akt signaling." Proc Natl Acad Sci USA. 106(9):3178-83.
Garcia-Marcos et al., 2010. "A structural determinant that renders G alpha(i) sensitive to activation by GIV/girdin is required to promote cell migration." J Biol Chem. 285(17):12765-77.
Ghosh et al., 2010. "A G(alpha)i-GIV molecular complex binds epidermal growth factor receptor and determines whether cells migrate or proliferate." Mol Biol Cell. 21(13):2338-54.
Garcia-Marcos et al., 2011. "Expression of GIV/Girdin, a metastasis-related protein, predicts patient survival in colon cancer." FASEB J. 25(2):590-9.
Garcia-Marcos et al., 2011. "A GDI (AGS3) and a GEF (GIV) regulate autophagy by balancing G protein activity and growth factor signals." Mol Biol Cell. 22(5):673-86.
Garcia-Marcos et al., 2011. "G Protein binding sites on Calnuc (nucleobindin 1) and NUCB2 (nucleobindin 2) define a new class of G(alpha)i-regulatory motifs." J Biol Chem. 286(32):28138-49.
Garcia-Marcos et al., 2012. "Functional characterization of the guanine nucleotide exchange factor (GEF) motif of GIV protein reveals a threshold effect in signaling." Proc Natl Acad Sci USA, 109(6):1961-6.
Ghosh et al., 2008. "Activation of Galphai3 triggers cell migration via regulation of GIV." J Cell Biol., 182(2):381-93.
Ghosh et al., 2011. "GIV/Girdin is a rheostat that fine-tunes growth factor signals during tumor progression." Cell Adh Migr. 5(3):237-48.
Lin et al., 2011. "Tyrosine phosphorylation of the Gα-interacting protein GIV promotes activation of phosphoinositide 3-kinase during cell migration." Sci Signal. 4(192):ra64. 32 pages.
Mittal et al., 2011 "Src homology domain 2-containing protein-tyrosine phosphatase-1 (SHP-1) binds and dephosphorylates G(alpha)-interacting, vesicle-associated protein (GIV)/Girdin and attenuates the GIV-phosphatidylinositol 3-kinase (PI3K)-Akt signaling pathway." J Biol Chem. 286(37):32404-15.

* cited by examiner

*Primary Examiner* — Gail R Gabel
(74) *Attorney, Agent, or Firm* — Morrison & Foerster LLP

(57) ABSTRACT

The present disclosure generally relates to tyrosine phosphorylation sites of an Akt enhancer, and methods for the detection of the phosphorylated tyrosine residues. In particular, anti-phosphotyrosine antibodies and binding proteins find use in the compositions and methods of the present disclosure.

18 Claims, 38 Drawing Sheets

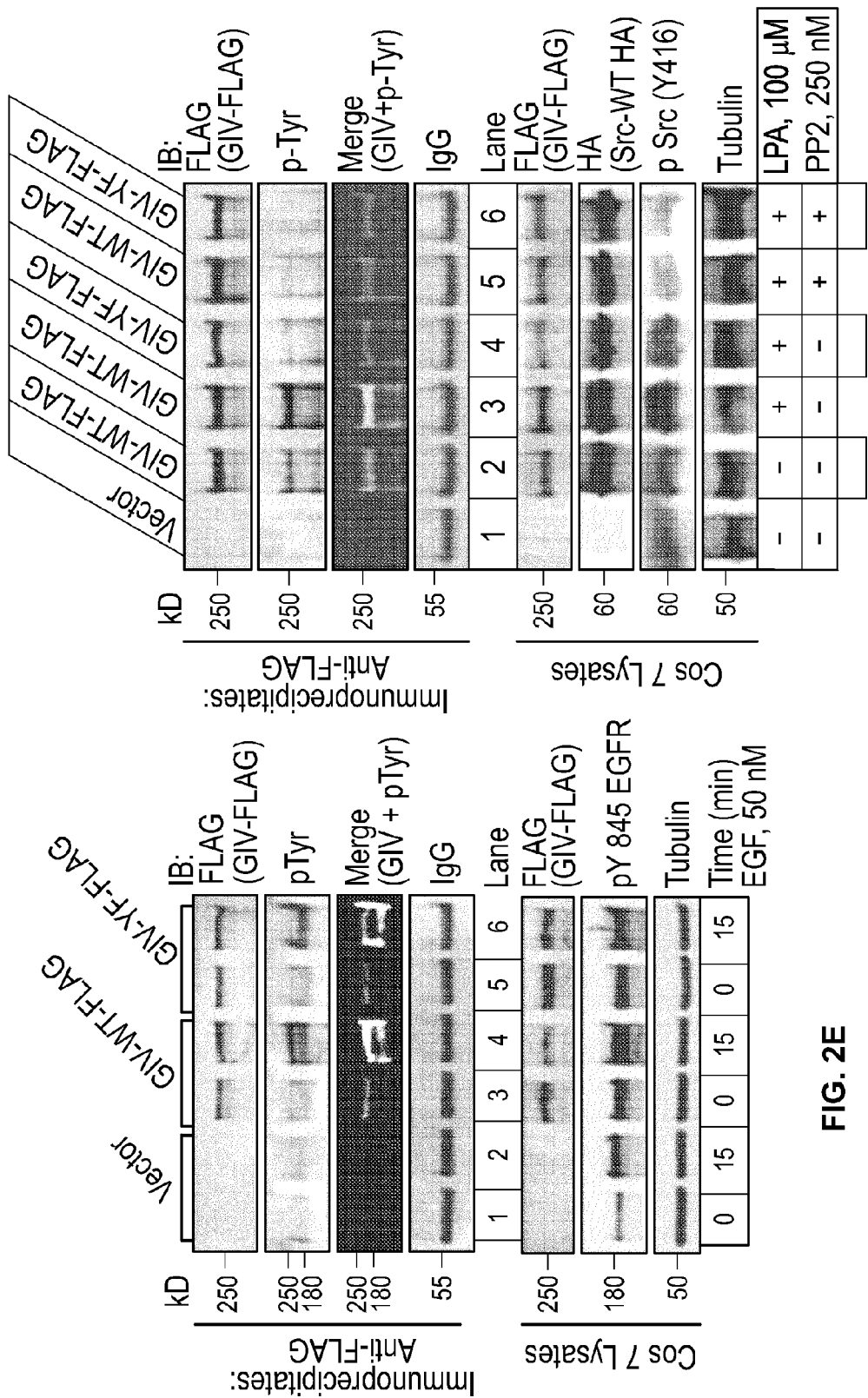

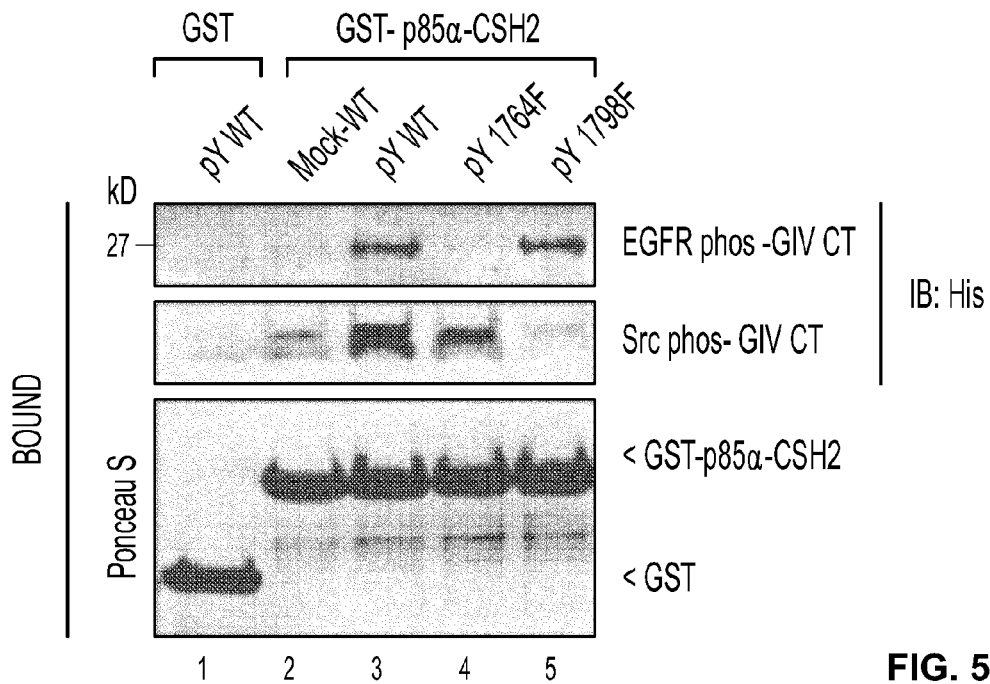
FIG. 5A
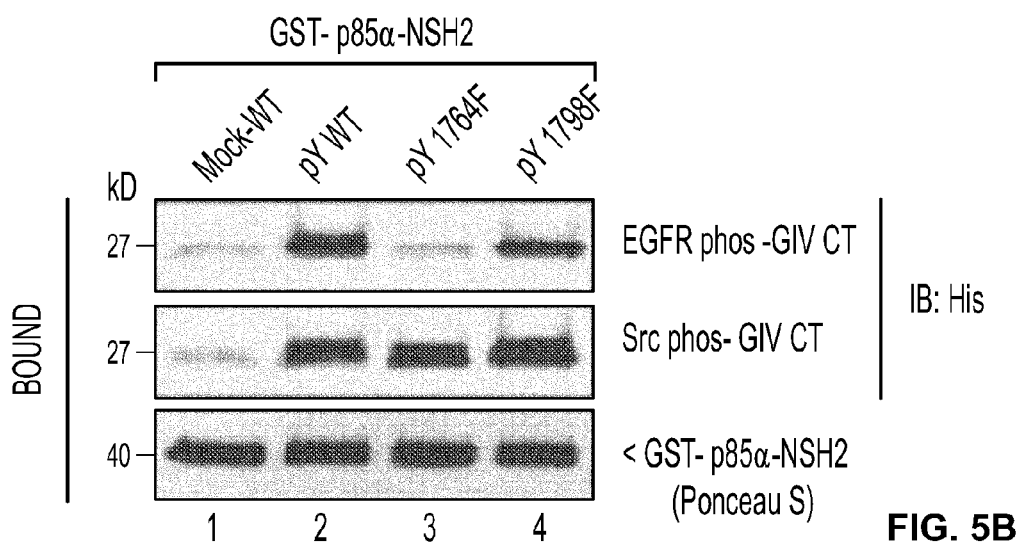
FIG. 5B
| INS REC | Y1322 | HIPYTHMN |
| MET REC | Y1356 | GEHYVHVN |
| PDGFRB | Y0751 | SVDYVPML |
| PDGFRA | Y0751 | TTQYVPML |
| CBL | Y0737 | SCTYEAMY |
| MET REC | Y1349 | NATYVNVK |
| EPO REC | Y0343 | QDTYLVLD |
| TIE2 | Y1101 | RKTYVNTT |
| SYK | Y0317 | FNPYEPTG |
| GIV/GIRDIN | Y1764 | EDTYFISS |
| GIV/GIRDIN | Y1798 | SNPYATLP |
| | | * |
FIG. 5C

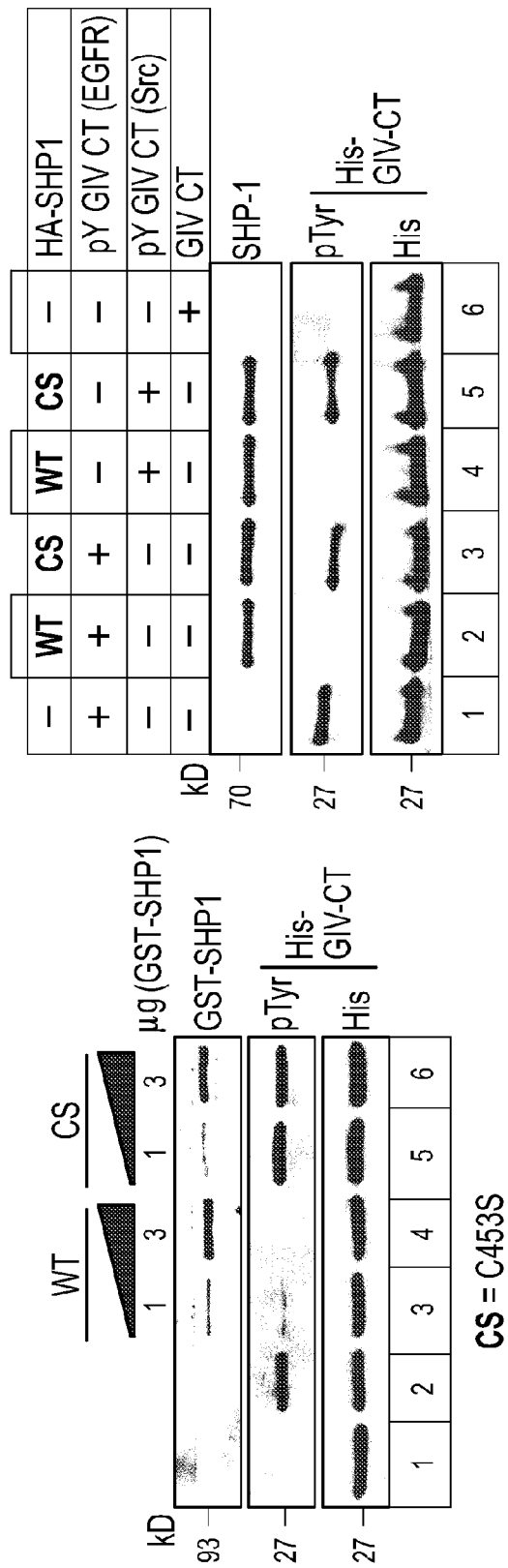
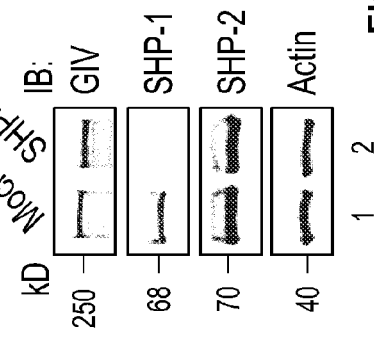
FIG. 16C
FIG. 16D
FIG. 16E

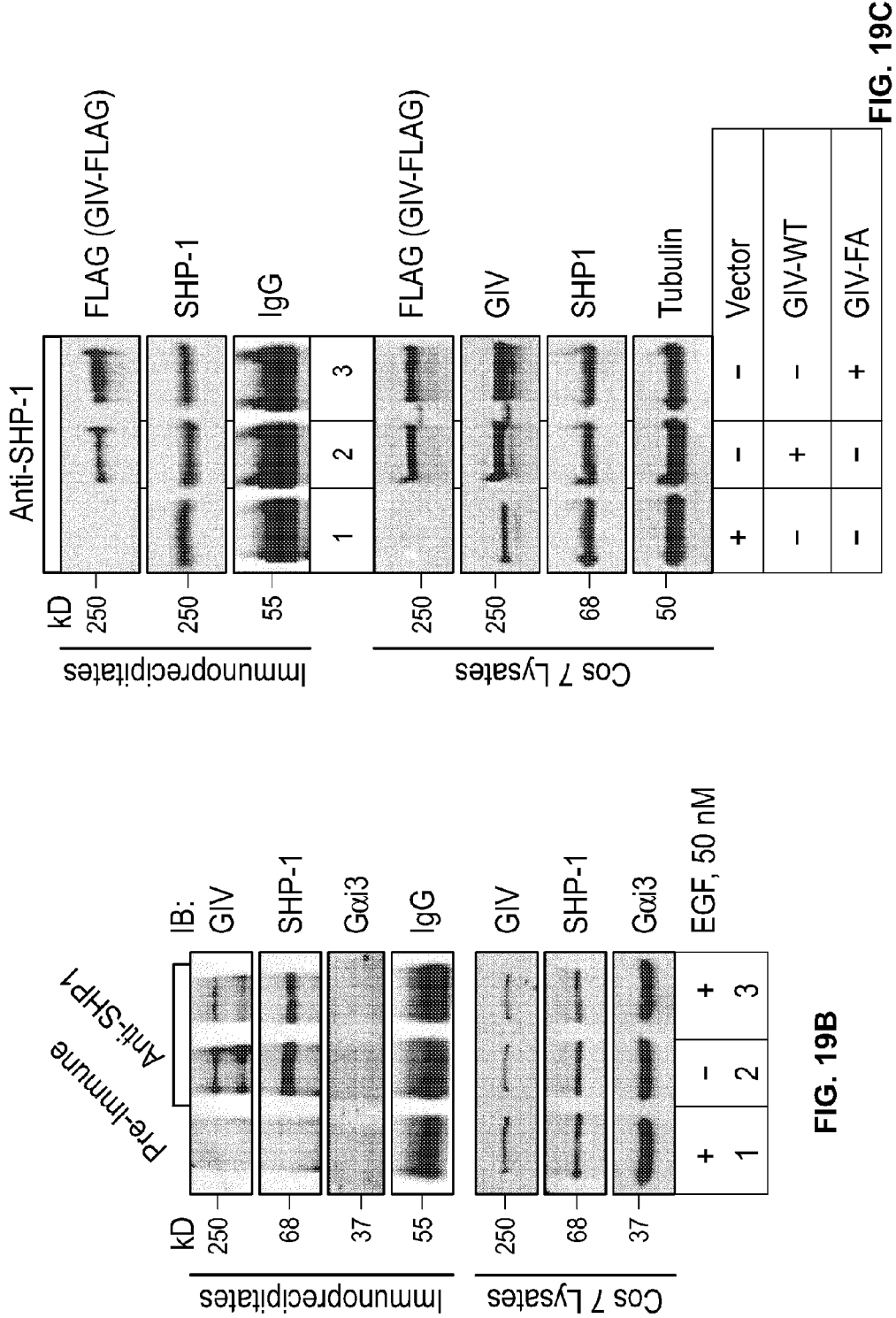

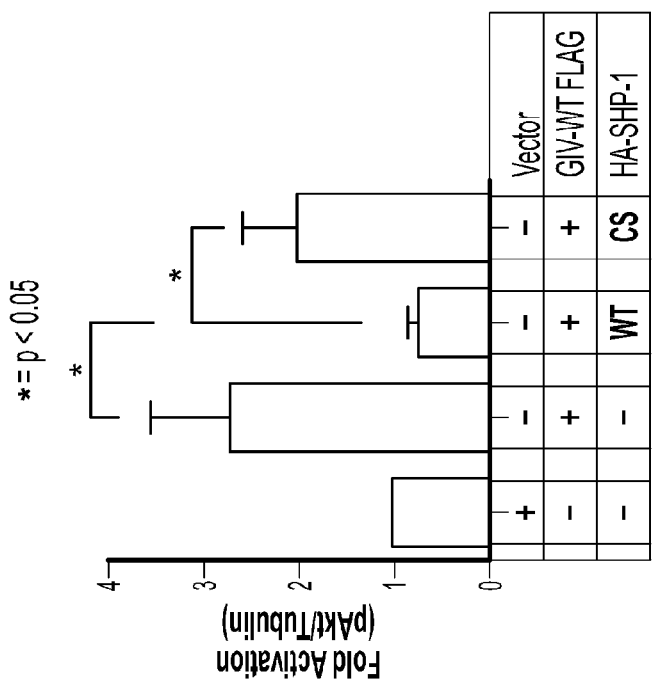
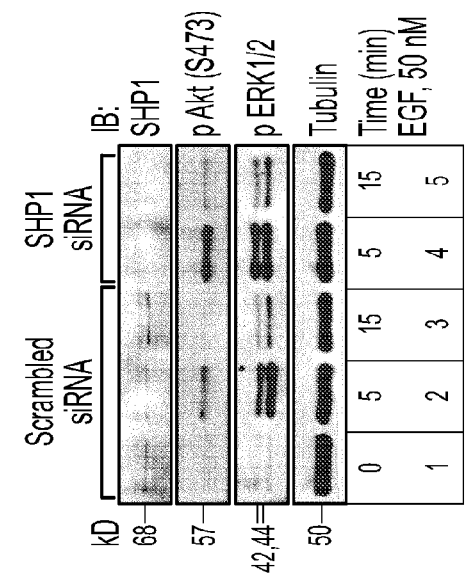
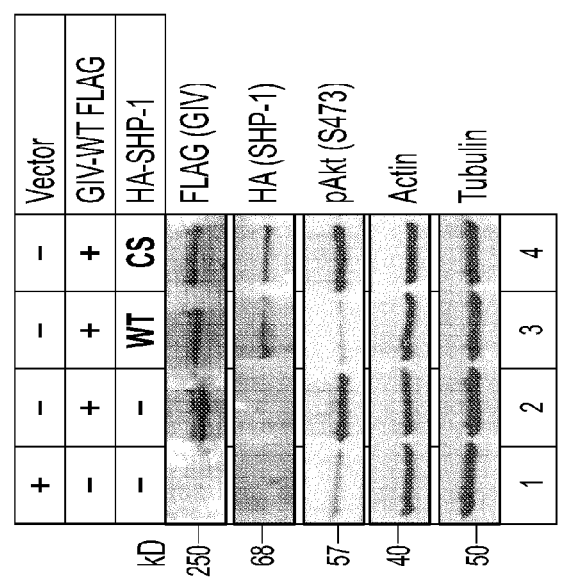
CS = C453S
FIG. 22A
FIG. 22B
FIG. 22C

SEQUENCE LISTING

<160> NUMBER OF SEQ ID NOS: 31

<210> SEQ ID NO 1
<211> LENGTH: 1870
<212> TYPE: PRT

-continued

<213> ORGANISM: Homo sapiens

<400> SEQUENCE: 1

```
Met Glu Asn Glu Ile Phe Thr Pro Leu Leu Glu Gln Phe Met Thr Ser
  1               5                  10                  15

Pro Leu Val Thr Trp Val Lys Thr Phe Gly Pro Leu Ala Ala Gly Asn
             20                  25                  30

Gly Thr Asn Leu Asp Glu Tyr Val Ala Leu Val Asp Gly Val Phe Leu
         35                  40                  45

Asn Gln Val Met Leu Gln Ile Asn Pro Lys Leu Glu Ser Gln Arg Val
 50                  55                  60

Asn Lys Lys Val Asn Asn Asp Ala Ser Leu Arg Met His Asn Leu Ser
 65                  70                  75                  80

Ile Leu Val Arg Gln Ile Lys Phe Tyr Tyr Gln Glu Thr Leu Gln Gln
                 85                  90                  95

Leu Ile Met Met Ser Leu Pro Asn Val Leu Ile Ile Gly Lys Asn Pro
            100                 105                 110

Phe Ser Glu Gln Gly Thr Glu Glu Val Lys Lys Leu Leu Leu Leu Leu
        115                 120                 125

Leu Gly Cys Ala Val Gln Cys Gln Lys Lys Glu Phe Ile Glu Arg
    130                 135                 140

Ile Gln Gly Leu Asp Phe Asp Thr Lys Ala Ala Val Ala Ala His Ile
145                 150                 155                 160

Gln Glu Val Thr His Asn Gln Glu Asn Val Phe Asp Leu Gln Trp Met
                165                 170                 175

Glu Val Thr Asp Met Ser Gln Glu Asp Ile Glu Pro Leu Leu Lys Asn
            180                 185                 190

Met Ala Leu His Leu Lys Arg Leu Ile Asp Glu Arg Asp Glu His Ser
        195                 200                 205

Glu Thr Ile Ile Glu Leu Ser Glu Glu Arg Asp Gly Leu His Phe Leu
    210                 215                 220

Pro His Ala Ser Ser Ala Gln Ser Pro Cys Gly Ser Pro Gly Met
225                 230                 235                 240

Lys Arg Thr Glu Ser Arg Gln His Leu Ser Val Glu Leu Ala Asp Ala
                245                 250                 255

Lys Ala Lys Ile Arg Arg Leu Arg Gln Glu Leu Glu Glu Lys Thr Glu
            260                 265                 270

Gln Leu Leu Asp Cys Lys Gln Glu Leu Glu Gln Met Glu Ile Glu Leu
        275                 280                 285

Lys Arg Leu Gln Gln Glu Asn Met Asn Leu Leu Ser Asp Ala Arg Ser
    290                 295                 300

Ala Arg Met Tyr Arg Asp Glu Leu Asp Ala Leu Arg Glu Lys Ala Val
305                 310                 315                 320

Arg Val Asp Lys Leu Glu Ser Glu Val Ser Arg Tyr Lys Glu Arg Leu
                325                 330                 335

His Asp Ile Glu Phe Tyr Lys Ala Arg Val Glu Glu Leu Lys Glu Asp
            340                 345                 350

Asn Gln Val Leu Leu Glu Thr Lys Thr Met Leu Glu Asp Gln Leu Glu
        355                 360                 365

Gly Thr Arg Ala Arg Ser Asp Lys Leu His Glu Leu Glu Lys Glu Asn
    370                 375                 380

Leu Gln Leu Lys Ala Lys Leu His Asp Met Glu Met Glu Arg Asp Met
385                 390                 395                 400
```

-continued

```
Asp Arg Lys Lys Ile Glu Glu Leu Met Glu Asn Met Thr Leu Glu
                405                 410                 415
Met Ala Gln Lys Gln Ser Met Asp Glu Ser Leu His Leu Gly Trp Glu
            420                 425                 430
Leu Glu Gln Ile Ser Arg Thr Ser Glu Leu Ser Glu Ala Pro Gln Lys
        435                 440                 445
Ser Leu Gly His Glu Val Asn Glu Leu Thr Ser Ser Arg Leu Leu Lys
    450                 455                 460
Leu Glu Met Glu Asn Gln Ser Leu Thr Lys Thr Val Glu Glu Leu Arg
465                 470                 475                 480
Thr Thr Val Asp Ser Val Glu Gly Asn Ala Ser Lys Ile Leu Lys Met
            485                 490                 495
Glu Lys Glu Asn Gln Arg Leu Ser Lys Lys Val Glu Ile Leu Glu Asn
        500                 505                 510
Glu Ile Val Gln Glu Lys Gln Ser Leu Gln Asn Cys Gln Asn Leu Ser
    515                 520                 525
Lys Asp Leu Met Lys Glu Lys Ala Gln Leu Glu Lys Thr Ile Glu Thr
530                 535                 540
Leu Arg Glu Asn Ser Glu Arg Gln Ile Lys Ile Leu Glu Gln Glu Asn
545                 550                 555                 560
Glu His Leu Asn Gln Thr Val Ser Ser Leu Arg Gln Arg Ser Gln Ile
            565                 570                 575
Ser Ala Glu Ala Arg Val Lys Asp Ile Glu Lys Glu Asn Lys Ile Leu
        580                 585                 590
His Glu Ser Ile Lys Glu Thr Ser Ser Lys Leu Ser Lys Ile Glu Phe
    595                 600                 605
Glu Lys Arg Gln Ile Lys Lys Glu Leu Glu His Tyr Lys Glu Lys Gly
610                 615                 620
Glu Arg Ala Glu Glu Leu Glu Asn Glu Leu His His Leu Glu Lys Glu
625                 630                 635                 640
Asn Glu Leu Leu Gln Lys Lys Ile Thr Asn Leu Lys Ile Thr Cys Glu
            645                 650                 655
Lys Ile Glu Ala Leu Glu Gln Glu Asn Ser Glu Leu Glu Arg Glu Asn
        660                 665                 670
Arg Lys Leu Lys Lys Thr Leu Asp Ser Phe Lys Asn Leu Thr Phe Gln
    675                 680                 685
Leu Glu Ser Leu Glu Lys Glu Asn Ser Gln Leu Asp Glu Glu Asn Leu
690                 695                 700
Glu Leu Arg Arg Asn Val Glu Ser Leu Lys Cys Ala Ser Met Lys Met
705                 710                 715                 720
Ala Gln Leu Gln Leu Glu Asn Lys Glu Leu Glu Ser Glu Lys Glu Gln
            725                 730                 735
Leu Lys Lys Gly Leu Glu Leu Leu Lys Ala Ser Phe Lys Lys Thr Glu
        740                 745                 750
Arg Leu Glu Val Ser Tyr Gln Gly Leu Asp Ile Glu Asn Gln Arg Leu
    755                 760                 765
Gln Lys Thr Leu Glu Asn Ser Asn Lys Lys Ile Gln Gln Leu Glu Ser
770                 775                 780
Glu Leu Gln Asp Leu Glu Met Glu Asn Gln Thr Leu Gln Lys Asn Leu
785                 790                 795                 800
Glu Glu Leu Lys Ile Ser Ser Lys Arg Leu Glu Gln Leu Glu Lys Glu
            805                 810                 815
Asn Lys Ser Leu Glu Gln Glu Thr Ser Gln Leu Glu Lys Asp Lys Lys
```

-continued

```
                820                 825                 830
Gln Leu Glu Lys Glu Asn Lys Arg Leu Arg Gln Gln Ala Glu Ile Lys
            835                 840                 845
Asp Thr Thr Leu Glu Glu Asn Val Lys Ile Gly Asn Leu Glu Lys
        850                 855                 860
Glu Asn Lys Thr Leu Ser Lys Glu Ile Gly Ile Tyr Lys Glu Ser Cys
865                 870                 875                 880
Val Arg Leu Lys Glu Leu Glu Lys Glu Asn Lys Glu Leu Val Lys Arg
                885                 890                 895
Ala Thr Ile Asp Ile Lys Thr Leu Val Thr Leu Arg Glu Asp Leu Val
            900                 905                 910
Ser Glu Lys Leu Lys Thr Gln Gln Met Asn Asn Asp Leu Glu Lys Leu
        915                 920                 925
Thr His Glu Leu Glu Lys Ile Gly Leu Asn Lys Glu Arg Leu Leu His
        930                 935                 940
Asp Glu Gln Ser Thr Asp Asp Arg Tyr Lys Leu Leu Glu Ser Lys Leu
945                 950                 955                 960
Glu Ser Thr Leu Lys Lys Ser Leu Glu Ile Lys Glu Glu Lys Ile Ala
                965                 970                 975
Ala Leu Glu Ala Arg Leu Glu Glu Ser Thr Asn Tyr Asn Gln Gln Leu
            980                 985                 990
Arg Gln Glu Leu Lys Thr Val Lys Lys Asn Tyr Glu Ala Leu Lys Gln
        995                 1000                1005
Arg Gln Asp Glu Glu Arg Met Val Gln Ser Ser Pro Pro Ile Ser Gly
    1010                1015                1020
Glu Asp Asn Lys Trp Glu Arg Glu Ser Gln Glu Thr Thr Arg Glu Leu
1025                1030                1035                1040
Leu Lys Val Lys Asp Arg Leu Ile Glu Val Glu Arg Asn Asn Ala Thr
                1045                1050                1055
Leu Gln Ala Glu Lys Gln Ala Leu Lys Thr Gln Leu Lys Gln Leu Glu
            1060                1065                1070
Thr Gln Asn Asn Asn Leu Gln Ala Gln Ile Leu Ala Leu Gln Arg Gln
        1075                1080                1085
Thr Val Ser Leu Gln Glu Gln Asn Thr Thr Leu Gln Thr Gln Asn Ala
    1090                1095                1100
Lys Leu Gln Val Glu Asn Ser Thr Leu Asn Ser Gln Ser Thr Ser Leu
1105                1110                1115                1120
Met Asn Gln Asn Ala Gln Leu Leu Ile Gln Gln Ser Ser Leu Glu Asn
                1125                1130                1135
Glu Asn Glu Ser Val Ile Lys Glu Arg Glu Asp Leu Lys Ser Leu Tyr
            1140                1145                1150
Asp Ser Leu Ile Lys Asp His Glu Lys Leu Glu Leu Leu His Glu Arg
        1155                1160                1165
Gln Ala Ser Glu Tyr Glu Ser Leu Ile Ser Lys His Gly Thr Leu Lys
    1170                1175                1180
Ser Ala His Lys Asn Leu Glu Val Glu His Arg Asp Leu Glu Asp Arg
1185                1190                1195                1200
Tyr Asn Gln Leu Leu Lys Gln Lys Gly Gln Leu Glu Asp Leu Glu Lys
                1205                1210                1215
Met Leu Lys Val Glu Gln Glu Lys Met Leu Leu Glu Asn Lys Asn His
            1220                1225                1230
Glu Thr Val Ala Ala Glu Tyr Lys Lys Leu Cys Gly Glu Asn Asp Arg
        1235                1240                1245
```

-continued

Leu Asn His Thr Tyr Ser Gln Leu Leu Lys Glu Thr Glu Val Leu Gln
    1250                1255                1260

Thr Asp His Lys Asn Leu Lys Ser Leu Leu Asn Asn Ser Lys Leu Glu
1265                1270                1275                1280

Gln Thr Arg Leu Glu Ala Glu Phe Ser Lys Leu Lys Glu Gln Tyr Gln
            1285                1290                1295

Gln Leu Asp Ile Thr Ser Thr Lys Leu Asn Asn Gln Cys Glu Leu Leu
            1300                1305                1310

Ser Gln Leu Lys Gly Asn Leu Glu Glu Asn Arg His Leu Leu Asp
        1315                1320                1325

Gln Ile Gln Thr Leu Met Leu Gln Asn Arg Thr Leu Leu Glu Gln Asn
        1330                1335                1340

Met Glu Ser Lys Asp Leu Phe His Val Glu Gln Arg Gln Tyr Ile Asp
1345                1350                1355                1360

Lys Leu Asn Glu Leu Arg Arg Gln Lys Glu Lys Leu Glu Glu Lys Ile
            1365                1370                1375

Met Asp Gln Tyr Lys Phe Tyr Asp Pro Ser Pro Arg Arg Gly
            1380                1385                1390

Asn Trp Ile Thr Leu Lys Met Arg Lys Leu Ile Lys Ser Lys Lys Asp
        1395                1400                1405

Ile Asn Arg Glu Arg Gln Lys Ser Leu Thr Leu Thr Pro Thr Arg Ser
    1410                1415                1420

Asp Ser Ser Glu Gly Phe Leu Gln Leu Pro His Gln Asp Ser Gln Asp
1425                1430                1435                1440

Ser Ser Ser Val Gly Ser Asn Ser Leu Glu Asp Gly Gln Thr Leu Gly
            1445                1450                1455

Thr Lys Lys Ser Ser Met Val Ala Leu Lys Arg Leu Pro Phe Leu Arg
        1460                1465                1470

Asn Arg Pro Lys Asp Lys Asp Lys Met Lys Ala Cys Tyr Arg Arg Ser
        1475                1480                1485

Met Ser Met Asn Asp Leu Val Gln Ser Met Val Leu Ala Gly Gln Trp
    1490                1495                1500

Thr Gly Ser Thr Glu Asn Leu Glu Val Pro Asp Asp Ile Ser Thr Gly
1505                1510                1515                1520

Lys Arg Arg Lys Glu Leu Gly Ala Met Ala Phe Ser Thr Thr Ala Ile
            1525                1530                1535

Asn Phe Ser Thr Val Asn Ser Ser Ala Gly Phe Arg Ser Lys Gln Leu
        1540                1545                1550

Val Asn Asn Lys Asp Thr Thr Ser Phe Glu Asp Ile Ser Pro Gln Gly
        1555                1560                1565

Val Ser Asp Asp Ser Ser Thr Gly Ser Arg Val His Ala Ser Arg Pro
    1570                1575                1580

Ala Ser Leu Asp Ser Gly Arg Thr Ser Thr Ser Asn Ser Asn Asn
1585                1590                1595                1600

Ala Ser Leu His Glu Val Lys Ala Gly Ala Val Asn Asn Gln Ser Arg
            1605                1610                1615

Pro Gln Ser His Ser Ser Gly Glu Phe Ser Leu Leu His Asp His Glu
        1620                1625                1630

Ala Trp Ser Ser Ser Gly Ser Ser Pro Ile Gln Tyr Leu Lys Arg Gln
        1635                1640                1645

Thr Arg Ser Ser Pro Val Leu Gln His Lys Ile Ser Glu Thr Leu Glu
    1650                1655                1660

```
Ser Arg His His Lys Ile Lys Thr Gly Ser Pro Gly Ser Glu Val Val
1665                1670                1675                1680

Thr Leu Gln Gln Phe Leu Glu Glu Ser Asn Lys Leu Thr Ser Val Gln
            1685                1690                1695

Ile Lys Ser Ser Ser Gln Glu Asn Leu Leu Asp Glu Val Met Lys Ser
        1700                1705                1710

Leu Ser Val Ser Ser Asp Phe Leu Gly Lys Asp Lys Pro Val Ser Cys
    1715                1720                1725

Gly Leu Ala Arg Ser Val Ser Gly Lys Thr Pro Gly Asp Phe Tyr Asp
    1730                1735                1740

Arg Arg Thr Thr Lys Pro Glu Phe Leu Arg Pro Gly Pro Arg Lys Thr
1745                1750                1755                1760

Glu Asp Thr Tyr Phe Ile Ser Ser Ala Gly Lys Pro Thr Pro Gly Thr
            1765                1770                1775

Gln Gly Lys Ile Lys Leu Val Lys Glu Ser Ser Leu Ser Arg Gln Ser
        1780                1785                1790

Lys Asp Ser Asn Pro Tyr Ala Thr Leu Pro Arg Ala Ser Ser Val Ile
    1795                1800                1805

Ser Thr Ala Glu Gly Thr Thr Arg Arg Thr Ser Ile His Asp Phe Leu
1810                1815                1820

Thr Lys Asp Ser Arg Leu Pro Ile Ser Val Asp Ser Pro Ala Ala
1825                1830                1835                1840

Ala Asp Ser Asn Thr Thr Ala Ala Ser Asn Val Asp Lys Val Gln Glu
            1845                1850                1855

Ser Arg Asn Ser Lys Ser Arg Ser Arg Glu Gln Gln Ser Ser
            1860                1865                1870

<210> SEQ ID NO 2
<211> LENGTH: 17
<212> TYPE: PRT
<213> ORGANISM: Homo sapiens
<220> FEATURE:
<221> NAME/KEY: VARIANT
<222> LOCATION: 9
<223> OTHER INFORMATION: Xaa = phosphor-tyrosine

<400> SEQUENCE: 2

Gly Pro Arg Lys Thr Glu Asp Thr Xaa Phe Ile Ser Ser Ala Gly Lys
1               5                   10                  15

Pro

<210> SEQ ID NO 3
<211> LENGTH: 17
<212> TYPE: PRT
<213> ORGANISM: Homo sapiens
<220> FEATURE:
<221> NAME/KEY: VARIANT
<222> LOCATION: 9
<223> OTHER INFORMATION: Xaa = phosphor-tyrosine

<400> SEQUENCE: 3

Arg Gln Ser Lys Asp Ser Asn Pro Xaa Ala Thr Leu Pro Arg Ala Ser
1               5                   10                  15

Ser

<210> SEQ ID NO 4
<211> LENGTH: 4
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 1
<223> OTHER INFORMATION: Xaa = phosphor-tyrosine
<220> FEATURE:
<221> NAME/KEY: VARIANT
<222> LOCATION: 2
<223> OTHER INFORMATION: Xaa = Val or Met or Leu or Ile
<220> FEATURE:
<221> NAME/KEY: VARIANT
<222> LOCATION: 3
<223> OTHER INFORMATION: Xaa = Any Amino Acid

<400> SEQUENCE: 4

Xaa Xaa Xaa Met
 1

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = phosphor-tyrosine

<400> SEQUENCE: 5

Xaa Phe Ile Ser Ser
 1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = phosphor-tyrosine

<400> SEQUENCE: 6

Xaa Ala Thr Leu Pro
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

His Ile Pro Tyr Thr His Met Asn
 1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Gly Glu His Tyr Val His Val Asn
 1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ser Val Asp Tyr Val Pro Met Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Thr Thr Gln Tyr Val Pro Met Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

Ser Cys Thr Tyr Glu Ala Met Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Asn Ala Thr Tyr Val Asn Val Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Gln Asp Thr Tyr Leu Val Leu Asp
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Arg Lys Thr Tyr Val Asn Thr Thr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Phe Asn Pro Tyr Glu Pro Thr Gly
 1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Glu Asp Thr Tyr Phe Ile Ser Ser
 1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ser Asn Pro Tyr Ala Thr Leu Pro
 1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 5
<223> OTHER INFORMATION: Xaa = Any Amino Acid

<400> SEQUENCE: 18

Tyr Xaa Xaa Met Xaa
 1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 5
<223> OTHER INFORMATION: Xaa = Any Amino Acid
<220> FEATURE:
<221> NAME/KEY: VARIANT
<222> LOCATION: 4
<223> OTHER INFORMATION: Xaa = Ser or Thr

<400> SEQUENCE: 19

Tyr Xaa Xaa Xaa Xaa
 1               5

<210> SEQ ID NO 20
<211> LENGTH: 8
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = phosphor-tyrosine

<400> SEQUENCE: 20

Glu Asp Thr Xaa Phe Ile Ser Ser
 1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = phosphor-tyrosine

<400> SEQUENCE: 21

Ser Asn Pro Xaa Ala Thr Leu Pro
 1               5

<210> SEQ ID NO 22
<211> LENGTH: 248
<212> TYPE: PRT
<213> ORGANISM: Homo sapiens

<400> SEQUENCE: 22

Gly Glu Phe Ser Leu Leu His Asp His Glu Ala Trp Ser Ser Ser Gly
 1               5                  10                  15

Ser Ser Pro Ile Gln Tyr Leu Lys Arg Gln Thr Arg Ser Ser Pro Val
                20                  25                  30

Leu Gln His Lys Ile Ser Glu Thr Leu Glu Ser Arg His His Lys Ile
            35                  40                  45

Lys Thr Gly Ser Pro Gly Ser Glu Val Val Thr Leu Gln Gln Phe Leu
50                  55                  60

Glu Glu Ser Asn Lys Leu Thr Ser Val Gln Ile Lys Ser Ser Ser Gln
65                  70                  75                  80

Glu Asn Leu Leu Asp Glu Val Met Lys Ser Leu Ser Val Ser Ser Asp
                85                  90                  95

Phe Leu Gly Lys Asp Lys Pro Val Ser Cys Gly Leu Ala Arg Ser Val
            100                 105                 110

Ser Gly Lys Thr Pro Gly Asp Phe Tyr Asp Arg Arg Thr Thr Lys Pro
        115                 120                 125

Glu Phe Leu Arg Pro Gly Pro Arg Lys Thr Glu Asp Thr Tyr Phe Ile
    130                 135                 140

Ser Ser Ala Gly Lys Pro Thr Pro Gly Thr Gln Gly Lys Ile Lys Leu
145                 150                 155                 160

Val Lys Glu Ser Ser Leu Ser Arg Gln Ser Lys Asp Ser Asn Pro Tyr
                165                 170                 175

Ala Thr Leu Pro Arg Ala Ser Ser Val Ile Ser Thr Ala Glu Gly Thr
            180                 185                 190

Thr Arg Arg Thr Ser Ile His Asp Phe Leu Thr Lys Asp Ser Arg Leu
        195                 200                 205

Pro Ile Ser Val Asp Ser Pro Pro Ala Ala Ala Asp Ser Asn Thr Thr
```

Ala Ala Ser Asn Val Asp Lys Val Gln Glu Ser Arg Asn Ser Lys Ser
225                 230                 235                 240

Arg Ser Arg Glu Gln Gln Ser Ser
                245

<210> SEQ ID NO 23
<211> LENGTH: 227
<212> TYPE: PRT
<213> ORGANISM: Pan troglodyte

<400> SEQUENCE: 23

Gly Glu Phe Ser Leu Leu His Asp His Glu Ala Trp Ser Ser Ser Gly
1               5                   10                  15

Ser Ser Pro Ile Gln Tyr Leu Lys Arg Gln Thr Arg Ser Ser Pro Val
                20                  25                  30

Leu Gln His Lys Ile Ser Glu Thr Leu Glu Ser Arg His His Lys Ile
            35                  40                  45

Lys Thr Gly Ser Pro Gly Ser Glu Val Val Thr Leu Gln Gln Phe Leu
50                  55                  60

Glu Glu Ser Asn Lys Leu Thr Ser Ile Gln Ile Lys Ser Ser Ser Gln
65                  70                  75                  80

Glu Asn Leu Leu Asp Glu Val Met Lys Ser Leu Ser Val Ser Ser Asp
                85                  90                  95

Phe Leu Gly Lys Asp Lys Pro Val Ser Cys Gly Leu Ala Arg Ser Val
            100                 105                 110

Ser Gly Lys Thr Pro Gly Asp Phe Tyr Asp Arg Arg Thr Thr Lys Pro
        115                 120                 125

Glu Phe Leu Arg Pro Gly Pro Arg Lys Thr Glu Asp Thr Tyr Phe Ile
130                 135                 140

Ser Ser Ala Gly Lys Pro Thr Pro Gly Thr Gln Gly Lys Ile Lys Leu
145                 150                 155                 160

Val Lys Glu Ser Ser Leu Ser Arg Gln Ser Lys Asp Ser Asn Pro Tyr
                165                 170                 175

Ala Thr Leu Pro Arg Ala Ser Ser Val Ile Ser Thr Ala Glu Gly Thr
            180                 185                 190

Thr Arg Arg Thr Ser Ile His Asp Phe Leu Thr Lys Asp Ser Arg Leu
        195                 200                 205

Pro Ile Ser Val Asp Ser Pro Pro Ala Ala Asp Ser Asn Thr Thr
210                 215                 220

Ala Ala Ser
225

<210> SEQ ID NO 24
<211> LENGTH: 249
<212> TYPE: PRT
<213> ORGANISM: Mus musculus

<400> SEQUENCE: 24

Gly Asp Phe Ser Leu Leu His Asp His Glu Thr Trp Ser Ser Ser Gly
1               5                   10                  15

Ser Ser Pro Ile Gln Tyr Leu Lys Arg Gln Thr Arg Ser Ser Pro Met
                20                  25                  30

Leu Gln His Lys Ile Ser Glu Thr Ile Glu Ser Arg Ala His His Lys
            35                  40                  45

Met Lys Ala Gly Ser Pro Gly Ser Glu Val Val Thr Leu Gln Gln Phe

```
              50                  55                  60
Leu Glu Glu Ser Asn Lys Leu Thr Ser Ile Gln Leu Lys Ser Ser Ser
 65                  70                  75                  80

Gln Glu Asn Leu Leu Asp Glu Val Met Lys Ser Leu Ser Val Ser Ser
                 85                  90                  95

Asp Phe Leu Gly Lys Asp Lys Pro Val Ser Cys Thr Leu Ala Arg Ser
                100                 105                 110

Val Ser Gly Lys Thr Pro Gly Asp Phe Tyr Asp Arg Arg Thr Thr Lys
            115                 120                 125

Pro Glu Phe Leu Arg Thr Gly Pro Gln Lys Thr Glu Asp Ala Tyr Thr
130                 135                 140

Ile Ser Ser Ala Gly Lys Pro Thr Pro Ser Thr Gln Gly Lys Ile Lys
145                 150                 155                 160

Leu Val Lys Glu Thr Ser Val Ser Arg Gln Ser Lys Asp Ser Asn Pro
                165                 170                 175

Tyr Ala Thr Leu Pro Arg Ala Ser Ser Val Ile Ser Thr Ala Glu Gly
                180                 185                 190

Thr Thr Arg Arg Thr Ser Ile His Asp Phe Leu Ser Lys Asp Ser Arg
            195                 200                 205

Leu Pro Val Ser Val Asp Ser Ser Pro Pro Thr Ala Gly Ser Ser Ser
210                 215                 220

Thr Thr Ala Ser Asn Val Asn Lys Val Gln Glu Ser Arg Asn Ser Lys
225                 230                 235                 240

Ser Arg Ser Arg Glu Gln Gln Ser Ser
            245

<210> SEQ ID NO 25
<211> LENGTH: 249
<212> TYPE: PRT
<213> ORGANISM: Rattus norvegicus

<400> SEQUENCE: 25

Gly Asp Phe Ser Leu Leu His Asp His Glu Thr Trp Ser Ser Ser Gly
 1               5                  10                  15

Ser Ser Pro Val Gln Tyr Leu Lys Arg Gln Thr Arg Ser Ser Pro Met
            20                  25                  30

Leu Gln His Lys Met Ser Glu Thr Val Asp Ser Gln Ala His His Lys
        35                  40                  45

Met Asn Ala Gly Ser Pro Gly Ser Glu Val Val Thr Leu Gln Gln Phe
 50                  55                  60

Leu Glu Glu Ser Asn Lys Leu Thr Ser Ile Gln Leu Lys Ser Ser Ser
 65                  70                  75                  80

Gln Glu Asn Leu Leu Asp Glu Val Met Lys Ser Leu Ser Val Ser Ser
                 85                  90                  95

Asp Phe Leu Gly Lys Asp Lys Pro Val Ser Cys Thr Leu Ala Arg Ser
                100                 105                 110

Val Ser Gly Lys Ala Pro Gly Asp Phe Tyr Asp Arg Arg Thr Ala Lys
            115                 120                 125

Pro Glu Phe Leu Arg Thr Gly Pro Gln Lys Thr Glu Asp Ala Tyr Ser
130                 135                 140

Ile Ser Ser Ala Gly Lys Pro Thr Pro Ser Thr Gln Gly Lys Ile Lys
145                 150                 155                 160

Leu Val Lys Glu Thr Ser Val Leu Arg Gln Ser Lys Asp Ser Asn Pro
                165                 170                 175
```

```
Tyr Ala Thr Leu Pro Arg Ala Ser Ser Val Ile Ser Thr Ala Glu Gly
            180                 185                 190

Thr Thr Arg Arg Thr Ser Ile His Asp Phe Leu Ser Lys Asp Ser Arg
        195                 200                 205

Leu Pro Val Ser Val Glu Pro Ala Pro Pro Ala Gly Gly Ser Ser
    210                 215                 220

Thr Ala Ala Ser Asn Val Asn Lys Val Gln Glu Ser Arg Asn Ser Lys
225                 230                 235                 240

Ser Arg Ser Arg Glu Gln Gln Ser Ser
            245
```

<210> SEQ ID NO 26
<211> LENGTH: 254
<212> TYPE: PRT
<213> ORGANISM: Ornithorhynchus anatinus

<400> SEQUENCE: 26

```
Gly Glu Phe Ser Leu Leu His Asp His Asp Ala Trp Ser Ser Ser Ser
  1               5                  10                  15

Ser Ser Pro Ile Gln Tyr Leu Lys Arg Asn Thr Arg Ser Ser Pro Gly
             20                  25                  30

Leu Gln His Lys Met Pro Glu Thr Leu Asp Gly Gln Gly Tyr His Arg
         35                  40                  45

Ile Lys Thr Gly Ser Pro Gly Ser Glu Val Val Thr Leu Gln Gln Phe
 50                  55                  60

Leu Glu Glu Ser Asn Lys Leu Thr Ser Val Gln Ile Lys Ser Ser Ser
 65                  70                  75                  80

Gln Glu Asn Leu Leu Asp Glu Val Met Lys Ser Leu Ser Val Ser Pro
             85                  90                  95

Asp Phe Met Gly Arg Glu Lys Thr Val Lys Gln Ser Ala Val Gly Cys
            100                 105                 110

Gly Ile Ser Arg Ser Val Ser Val Arg Cys Thr Thr Asp Phe Ser Asp
        115                 120                 125

Gly Lys Pro Thr Lys Pro Glu Gln Phe Val Leu Pro Asn Pro Arg Lys
    130                 135                 140

Thr Glu Asp Ser Tyr Phe Ser Ser Ser Gly Lys Ser Gly Thr Gln
145                 150                 155                 160

Thr Lys Val Lys Leu Val Lys Glu Thr Ser Leu Ser Gln Arg Gln Ser
                165                 170                 175

Lys Asp His Asn Pro Tyr Ala Thr Leu Pro Arg Ala Ser Ser Val Ile
            180                 185                 190

Ser Thr Ala Glu Gly Thr Thr Arg Arg Thr Ser Ile His Asp Phe Leu
        195                 200                 205

Ser Lys Asp Ser Arg Gln Pro Ile Ser Ile Asp Pro Ser Pro Ser Thr
    210                 215                 220

Thr Asp Ser Thr Phe Ser Ser Thr Ser Asn Val Glu Ala Ile Gln Glu
225                 230                 235                 240

Ser Arg Asn Ser Lys Ser Arg Ser Arg Glu Gln Gln Ser Ser
            245                 250
```

<210> SEQ ID NO 27
<211> LENGTH: 237
<212> TYPE: PRT
<213> ORGANISM: Gallus gallus

<400> SEQUENCE: 27

```
Gly Glu Phe Ser Met Leu His Glu His Asp Ala Trp Ser Ser Ser Ser
1               5                   10                  15

Ser Ser Pro Ile Gln Tyr Leu Lys Gly His Thr Arg Ser Ser Pro Val
            20                  25                  30

Leu Gln Gln Arg Thr Pro Glu Thr Leu Asp Arg Cys Gly Arg Gln Ile
        35                  40                  45

Lys Thr Asp Ser Pro Gly Ser Glu Val Val Thr Leu Gln Gln Phe Leu
50                  55                  60

Glu Glu Ser Asn Lys Ser Thr Ser Ser Glu Met Lys Ser Gly Ser Glu
65                  70                  75                  80

Glu Asn Leu Leu Asp Glu Val Met Arg Ser Leu Ser Glu Ser Ser Glu
                85                  90                  95

Leu Ala Gly Lys Glu Lys Leu Arg Lys Ala Ser Ala Gly Cys Gly Ile
            100                 105                 110

Val Arg Ser Leu Ser Val Lys Asn Pro Val Asp Phe Ser Glu Gly Arg
        115                 120                 125

Ser Ile Lys Pro Glu Gln Leu Val Arg Pro Ser Leu Arg Arg Thr Glu
    130                 135                 140

Asp Ala Tyr Phe Thr Ser Ser Pro Ile Lys Phe Thr Ser Gly Thr Gln
145                 150                 155                 160

Gly Lys Ala Lys Ser Val Lys Glu Met Met Gln Thr Ser Val Ser Gln
                165                 170                 175

Arg Gln Ser Arg Asp Cys Asn Pro Tyr Ala Thr Leu Pro Arg Ala Ser
            180                 185                 190

Ser Val Ile Ser Thr Ala Glu Gly Thr Thr Arg Arg Thr Ser Ile His
        195                 200                 205

Asp Phe Leu Ser Lys Asp Ile Arg Gln Pro Ala Ser Gly Asp Pro Ala
210                 215                 220

Thr Ser Thr Ala Asp Arg Ser Val Pro Ala Thr Ser Asn
225                 230                 235

<210> SEQ ID NO 28
<211> LENGTH: 171
<212> TYPE: PRT
<213> ORGANISM: Tetraodon nigroviridis

<400> SEQUENCE: 28

Gly Glu Phe Ser Leu Ser Leu Asp Gln Glu Leu Trp Ser Ser Ser Gly
1               5                   10                  15

Ser Ser Pro Val Ala Gln Pro Ser Arg Ser Ser Arg Gln Ser Pro Leu
            20                  25                  30

Gln Leu Arg Lys Ser Leu Asp Pro Asn Ala Ser Gly Ser Ser Pro Gly
        35                  40                  45

Gln Ser Arg Ala Gly Glu Val Leu Ser Leu Gln Gln Phe Leu Asp Glu
50                  55                  60

Gly Ile Asp Pro Ala Glu Val Cys Gln Thr Thr Gly Thr Pro His Leu
65                  70                  75                  80

Arg Lys Ala Glu Ser Thr Arg Val Arg Gly Ser Val Pro Ile Arg Pro
                85                  90                  95

Ser Leu Ser Ser Gln Gly Lys Ala Thr Ser Val Ser Glu Arg Leu Asp
            100                 105                 110

Ser Ala Ser Ser Thr Leu Pro Arg Ala Ser Ser Val Ile Ser Thr Ala
        115                 120                 125

Glu Gly Ser Thr Arg Arg Thr Ser Ile His Asp Met Leu Ser Lys Asp
    130                 135                 140
```

Ser Arg Gln Pro Val Ser Ala Gly Pro Arg Pro Gln Pro Thr Pro Ser
145                 150                 155                 160

Glu Tyr His Ser Asn Ser Ser Ala Leu Lys Val
                165                 170

<210> SEQ ID NO 29
<211> LENGTH: 173
<212> TYPE: PRT
<213> ORGANISM: Danio rerio

<400> SEQUENCE: 29

Ser Glu Ser Ser Gly Asp Val Ser Val Gly Val Asp Ala Gln Leu Gly
1               5                   10                  15

Ala Pro Asp Ala Arg Arg Ser Ala Pro Ser Thr Gly Ser Asp Val Val
                20                  25                  30

Ser Leu Gln Gln Phe Leu Glu Glu Asn Thr His Thr Ala Glu Asp Pro
            35                  40                  45

Pro Ser Ala Pro Pro Ser Ser Arg Glu Arg Val Lys Ala Arg Gly Ile
        50                  55                  60

Leu Arg Ser Ser Ser Gly Arg Ala Ala Ser Glu Ser Arg Ser Gly
65                  70                  75                  80

Ala Gly Arg Pro Ser Leu Arg Lys Thr Glu Ser Thr Arg Ala Arg Gly
                85                  90                  95

Cys Ala Pro Pro Arg Ala Gly Ser Ala Thr Gln Arg Ala Ala Ser Val
                100                 105                 110

Ser Ala Leu Asp Ser Ser Gly Leu Pro Arg Ala Ser Ser Val Ile Ser
            115                 120                 125

Thr Ala Glu Gly Ser Val Arg Arg Thr Ser Ile His Asp Leu Leu Ser
        130                 135                 140

Arg Asp Ser Arg Gln Pro Val Leu Val Asp Pro Pro Ala Leu Arg Ser
145                 150                 155                 160

Gly Ser Ser Asn Val Glu Asn Arg Lys Ser Lys Ser Arg
                165                 170

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 4, 5
<223> OTHER INFORMATION: Xaa = Any Amino Acid

<400> SEQUENCE: 30

Gly Xaa Phe Xaa Xaa Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = phosphor-tyrosine

```
<400> SEQUENCE: 31

Xaa Val Pro Met Leu
 1               5
```

TARGET OF THE PHOSPHOINOSITIDE 3-KINASE PATHWAY

CROSS REFERENCE TO RELATED APPLICATIONS

This application is a U.S. National Phase of PCT/US2012/048206, filed Jul. 25, 2012, which claims the benefit under 35 USC 119(e) of U.S. Provisional Application No. 61/511,518, filed Jul. 25, 2011, each of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643882000700SeqList.txt, date recorded: May 5, 2014, size: 35 KB).

FIELD

The present disclosure generally relates to tyrosine phosphorylation sites of an Akt enhancer, and methods for the detection of the phosphorylated tyrosine residues. In particular, anti-phosphotyrosine antibodies and binding proteins find use in the compositions and methods of the present disclosure.

BACKGROUND

Cancer is a heterogeneous disease for which curative treatment options remain elusive. The most promising treatment approaches today are molecularly targeted therapies tailored to address varied cellular defects in a tumor type- and stage-specific manner. Consequently, there is widespread interest in diagnostic and prognostic tools that aid in the identification and monitoring of molecular signaling events in tumor cells. Novel targeted therapeutics are needed that interfere with specific aberrant enzyme activities or protein interactions. The PI3K-Akt pathway is of particular interest because it is frequently hyperactivated during cancer invasion. Moreover, the progressive enhancement of PI3K-Akt signaling coupled to efficient cell migration is a hallmark of high metastatic potential.

Current state-of-the-art practice for prognostication and treatment is limited, especially for invasive tumors. Although the expression of several genes and proteins associated with PI3K-Akt signaling, actin remodeling, motility and invasion has been shown to vary among tumors, only a few of these markers are suitable for prognostication purposes. Thus, there is a persistent need for new biomarkers that play a critical role during tumor invasion, that are mechanistically well characterized, and that may also serve to stratify the clinical risk of metastasis among cancer patients.

Existing therapies in cancer invasion center around the pharmacologic blockade of individual receptor pathways such as VEGFR and EGFR pathways. However, in most carcinomas, including colon, breast and lung carcinomas, rapid resistance develops to single or combination receptor blocking therapies. Moreover, relapsed tumors are often more aggressive under these circumstances. Thus, new molecular targets are needed that are involved in the regulation of multiple signaling pathways, the inhibition of which may result in more efficacious treatments than single receptor blocking therapies. Additionally, many traditional kinase inhibitors targeting the kinase-domain suffer from severe dose-limiting toxicity. Alternative targets are therefore desired to create further options for the regulation of kinase activities, for example by interfering with the interaction between the kinase and another protein cofactor.

BRIEF SUMMARY

The present disclosure generally relates to tyrosine phosphorylation sites of an Akt enhancer, and methods for the detection of the phosphorylated tyrosine residues. In particular, anti-phosphotyrosine antibodies and binding proteins find use in the compositions and methods of the present disclosure.

Specifically, the present disclosure provides methods for assessing risk of metastasis of a solid tumor, the method comprising: a) subjecting a sample from the solid tumor to a procedure for quantitation of tyrosine phosphorylation of human Galpha-interacting protein (GIV); and b) detecting an elevated level of tyrosine phosphorylation of GIV in the sample as compared to a control sample, wherein the elevated level of tyrosine phosphorylation is associated with mestastasis or an increased risk of metastasis, and wherein the tyrosine phosphorylation of GIV comprises phosphorylation of one or both Y1764 and Y1798 of GIV. In some embodiments, the control sample comprises normal cells or non-metastatic cancer cells of the same tissue type as the solid tumor. In some embodiments, the solid tumor is a carcinoma. In a subset of these embodiments, the carcinoma is selected from the group consisting of a breast carcinoma, a colon carcinoma and a pancreatic carcinoma. In some embodiments, the carcinoma is breast carcinoma. In a subset of these embodiments, the breast carcinoma is from a patient with lymph node-negative breast cancer, while in others the breast carcinoma is from a patient with lymph node-positive breast cancer. In some embodiments, the elevated level of tyrosine phosphorylation is further associated with a poor prognosis for disease outcome (e.g., reduced disease-free survival or reduced overall survival. In some embodiments, the procedure for the quantitation of tyrosine phosphorylation of GIV comprises an antibody-based assay for measurement of anti-phosphotyrosine antibody binding to one or both of pY1764 and pY1798 of GIV in the sample from the solid tumor. In some embodiments the anti-phosphotyrosine antibody specifically binds to a polypeptide comprising the phosphorylated amino acid sequence of SEQ ID NO:5 (pYFISS) or the phosphorylated amino acid sequence of SEQ ID NO:2, but not the unphosphorylated forms thereof or tyrosine phosphorylated isoforms of other proteins. In some embodiments the anti-phosphotyrosine antibody specifically binds to a polypeptide comprising the phosphorylated amino acid sequence of SEQ ID NO:6 (pYATLP) or the phosphorylated amino acid sequence of SEQ ID NO:3, but not the unphosphorylated forms thereof or tyrosine phosphorylated isoforms of other proteins. In some embodiments the antibody-based assay is selected from the group consisting of immunofluorescence analysis, flow cytometry, immunohistochemistry, immunocytochemistry, antibody microarray, enzyme-linked immunosorbent assay (ELISA), and Western blotting. In some embodiments, the polypeptide is human Galpha-interacting protein (GIV). In some embodiments the procedure for the quantitation of tyrosine phosphorylation of GIV comprises the step of contacting the sample from a solid tumor with a protein that comprises an SH2 domain of p85alpha(PI3K).

The present disclosure also provides isolated antibodies that bind specifically to a polypeptide comprising the phosphorylated amino acid sequence of SEQ ID NO:5 (pYFISS) or the phosphorylated amino acid sequence of SEQ ID NO:6 (pYATLP). In some embodiments, the present disclosure provides an isolated antibody that binds to pY1764GIV but not Y1764 GIV. In some embodiments, the present disclosure provides an isolated antibody that binds to pY1798GIV but not Y1798 GIV. In some preferred embodiments, the antibody essentially does not bind unphosphorylated forms of the amino acid sequences or tyrosine phosphorylated forms of other proteins. In some embodiments the antibody specifically binds to the polypeptide comprising the phosphorylated amino acid sequence of SEQ ID NO:5 (pYFISS) or the phosphorylated amino acid sequence of SEQ ID NO:2. In some embodiments, the polypeptide comprising pYFISS comprises pY1764GIV. In some embodiments the antibody specifically binds to the polypeptide comprising the phosphorylated amino acid sequence of SEQ ID NO:6 (pYATLP) or the phosphorylated amino acid sequence of SEQ ID NO:3. In some embodiments, the polypeptide comprising pYATLP comprises pY1798GIV. In some embodiments, the polypeptide is human Galpha-interacting protein (GIV). In some embodiments, the antibody is a monoclonal antibody, while in other embodiments the antibody is a polyclonal antibody. In some embodiments, the antibody is an antibody fragment. In some embodiments, the antibody fragment is an Fab, F(ab')2, Fv or Sfv fragment. In some embodiments, the antibody is coupled to a detectable marker. In a subset of these embodiments, the detectable marker is selected from the group consisting of a radioisotope, a metal chelator, an enzyme, a fluorescent compound, a bioluminescent compound, or a chemiluminescent compound.

Additionally, the present disclosure provides methods of screening for modulators of PI3K-GIV association, the method comprising: a) providing a first protein comprising one or both of the phosphorylated amino acid sequence of SEQ ID NO:5 (pYFISS) or the phosphorylated amino acid sequence of SEQ ID NO:2, and the phosphorylated amino acid sequence of SEQ ID NO:6 (pYATLP) or the phosphorylated amino acid sequence of SEQ ID NO:3; b) providing a second protein comprising an SH2 domain of p85alpha (PI3K); c) contacting the first protein with the second protein in the presence and absence of a test compound; d) measuring the level of binding of the first protein to the second protein; e) detecting a difference in binding of the first protein to the second protein in the presence of the test compound as compared to the absence of the test compound, wherein when the difference in binding is a decrease in binding in the presence of the test compound, the test compound is determined to be a PI3K-GIV antagonist (inhibitor), or when the difference in binding is an increase in binding in the presence of the test compound, the test compound is determined to be a PI3K-GIV agonist (activator). The present disclosure further provides methods of screening for inhibitors of PI3K-GIV association, the method comprising: a) providing a first protein comprising one or both of the phosphorylated amino acid sequence of SEQ ID NO:5 (pYFISS) or the phosphorylated amino acid sequence of SEQ ID NO:2, and the phosphorylated amino acid sequence of SEQ ID NO:6 (pYATLP) or the phosphorylated amino acid sequence of SEQ ID NO:3; b) providing a second protein comprising an SH2 domain of p85alpha (PI3K); c) contacting the first protein to the second protein in the presence and absence of a test compound; d) measuring the level of binding of the first protein to the second protein; e) detecting a reduction in binding of the first protein to the second protein in the presence of the test compound as compared to the absence of the test compound, wherein the reduction in binding in the presence of the test compound indicates that the test compound is an inhibitor of PI3K-GIV association. In some embodiments the contacting is done within a host cell. In some embodiments the first and second proteins are isolated proteins. In some embodiments the first protein is human Galpha-interacting protein (GIV) or a carboxy-terminal fragment thereof. In some embodiments the test compound is an antibody. In some embodiments the test compound is a small molecule.

BRIEF DESCRIPTION OF THE DRAWINGS

FIG. 1 illustrates the role of GIV/Girdin in PI3K-pathway activation.

FIG. 2 illustrates that GIV is phosphorylated on tyrosines 1764 and 1798 by receptor and non-receptor tyrosine kinases. FIG. 2E shows that specific stimulation of GIV tyrosine phosphorylation by EGF. EGF stimulates tyrosine phosphorylation of GIV-WT but not of a phosphotyrosine mutant of GIV (GIV-YF) in which Y1764 and Y1798 are mutated to phenylalanines. Cos7 cells transiently transfected with FLAG-tagged wild-type (GIV-WT-FLAG), or GIV-YF-FLAG, or vector control were starved (0 min) or stimulated with 50 nM EGF for 15 min prior to lysis. Equal aliquots of cell lysates (lower panel) were incubated with anti-FLAG mAb. Immunoprecipitated complexes (top) were analyzed by two-color immunoblotting (IB) for GIV and pTyr using LI-COR Odyssey. Grayscale image for GIV (top panel) shows that GIV-FLAG is immunoprecipitated in lanes 3-6, but not in vector controls (lanes 1, 2). pTyr panel shows that tyrosine phosphorylation occurred upon ligand stimulation (lanes 4, 6). Yellow pixels of the overlaid GIV and pTyr (green) images (Merge panel) confirm that the immunoprecipitated GIV-WT (lane 4), but not GIV-YF mutant (lane 6) is phosphorylated on tyrosine(s) after EGF treatment. The ~180 kD band detected by anti-pTyr antibody (lanes 4, 6) was determined to be the GIV-associated pool of ligand-activated EGF receptor by immunoblotting for EGFR. FIG. 2F shows that Src kinase phosphorylates GIV after LPA stimulation. Cos7 cells transiently co-transfected with c-Src-HA and FLAG-tagged wild-type (GIV-WT-FLAG) or GIV-YF-FLAG, or vector control were starved for 12 h and then incubated for 1 h in the presence or absence of 250 nM PP2 (a Src kinase inhibitor). Cells were subsequently stimulated with 20 μM LPA for 15 min prior to lysis. Equal aliquots of lysates (bottom panels) were separated by SDS-PAGE and immunoblotted to confirm effective inhibition of Src, as determined by suppressed Src phosphorylation at Y416 in the presence of PP2. Remaining lysates were incubated with anti-FLAG mAb, and the immune complexes (top panels) were analyzed by two-color immunoblotting (IB) for GIV and pTyr using the LI-COR Odyssey Infrared Western Blot Imaging System. Grayscale image (topmost panel) shows that GIV is immunoprecipitated (lanes 2-6) only from GIV-FLAG transfected cells, but not from vector transfected cells (lane 1). The pTyr panel shows that tyrosine phosphorylation occurred in GIV-WT expressing cells exclusively upon ligand stimulation and in the absence of PP2 (lane 3). Yellow pixels of the overlaid GIV-FLAG (22) and pTyr (Green) images (Merge panel) confirm that GIV-WT is tyrosine phosphorylated after LPA stimulation in the absence of PP2, when Src kinases are active. Phosphorylation of GIV-WT is undetectable when Src is inhibited with the selective Src-inhibitor, PP2 (lane 5). No tyrosine phosphorylation is detected in GIV-YF either in the absence (lane 4) or presence (lane 6) of PP2.

FIG. 3 illustrates that tyrosine phosphorylation of GIV does not affect its ability to bind or activate Gαi, but is required for phosphorylation of Akt, actin remodeling, and cell migration. In FIG. 3E, mock-treated GIV-CT and in vitro EGFR-phosphorylated pY GIV-CT were incubated with 5 μg GST-Gαi3 or GST preloaded with GDP immobilized on glutathione beads. Bound proteins were analyzed by two-color immunoblotting (IB) for GIV CT (His) and pTyr using LI-COR Odyssey as in 2C. Yellow pixels in the overlaid GIV-CT and pTyr (green) images (Merge panels) confirm that His-GIV CT bound GST-Gαi3 equally, irrespective of GIV's phosphorylation status. FIG. 3F shows the amount of GTP hydrolyzed in 10 min by His-Gαi3, which was determined in the presence of the indicated amounts of sham-treated (●, GIV-CT) and in vitro EGFR-phosphorylated (○, pY GIV-CT) His-GIV-CT. Both GIV-CT and pY GIV-CT increased the steady-state GTPase activity of His-Gαi3 efficiently and equally in a dose-dependent manner.

FIG. 4 illustrates that GIV interacts with p85α via its phosphorylated C-terminus.

FIG. 5 illustrates the structural basis for the GIV-p85α interaction. FIG. 5A shows that both phosphotyrosines 1764 and 1798 on GIV's C-terminus directly bind p85α-CSH2. His-GIV CT wild-type (pY-WT) and single tyrosine mutants (pY1764F and pY1798F) were phosphorylated in vitro using recombinant EGFR or Src kinase. Equal aliquots (~6 μg) of each phosphoprotein or a mock-treated control (mock-WT) were used in pulldown assays with 35 μg GST-p85α-CSH2 or GST immobilized on glutathione beads. Bound proteins were analyzed for His (His-GIV CT) by immunoblotting (IB). EGFR-phosphorylated pY-WT (top panel, lane 3) and pY1798F (lane 5), but not pY1764F (lane 4) bound GST-p85α-CSH2. Src-phosphorylated pY-WT (bottom panel, lane 3) and pY1764F (lane 4), but not pY1798F (lane 5) bound GST-p85α-CSH2. As anticipated, without phosphorylation the mock-treated GIV-CT (mock-WT, both panels, lane 2) did not bind. FIG. 5B shows that GIV's phosphotyrosines 1764 and 1798 directly bind p85α-NSH2. In vitro phosphorylated His-GIV CT wild-type (pY-WT) and single tyrosine mutants (pY1764F and pY1798F) were used in pulldown assays with GST-p85α-NSH2. EGFR-phosphorylated pY-WT (top panel, lane 2) and pY1798F (lane 4), but not pY1764F (lane 3) bound GST-p85α-NSH2. Src-phosphorylated pY-WT (bottom panel, lane 2), pY1764F (lane 3), and pY1798F (lane 4) bound GST-p85α-NSH2. As anticipated, without phosphorylation the mock-treated GIV CT (mock-WT, lane 1) did not bind. FIG. 5C provides an alignment of Y1764 on GIV with other known binding partners of p85α-CSH2 (SEQ ID NOs:7-17). The sequence flanking Y1764 in GIV was aligned with known phosphopeptide-binding sites on other p85α-interacting proteins. In most proteins the YXXMX motif (SEQ ID NO:18) is the canonical p85α-phosphotyrosine recognition site. In Tie2, Syk, and GIV, the YXXS/TX motif (SEQ ID NO:19) emerges as the non-canonical consensus for p85α recognition. FIG. 5D shows the proposed structure of the complex between CSH2 domain of p85α and GIV-derived phosphopeptide EDTpY$^{1764}$FISS (SEQ ID NO:20). FIG. 5E shows the proposed structure of the complex between NSH2 domain of p85α and GIV-derived phosphopeptide SNPpY$^{1798}$ATLP (SEQ ID NO:21). pY$^{1764}$ of GIV makes hydrogen bonds with residues of CSH2 in a manner similar to the established crystal structure of this domain with pY$^{751}$ of PDGFRβ. Similarly, pY$^{1798}$ of GIV makes hydrogen bonds with residues of NSH2 as seen in the resolved crystal structure of this domain complexed with phosphotyrosyl peptide of c-Kit. Multiple favorable polar and non-polar contacts are formed in both cases, including packing of F1765 (FIG. 5D) and L1801 (FIG. 5E) into the hydrophobic pockets occupied by M$^{754}$ of PDGFRβ and M$^{724}$ of c-Kit in their respective complex structures with the SH2 domains of p85α. No steric clashes were observed in either model.

FIG. 7 illustrates GIV's dual role as an enhancer of and a substrate for Akt kinase.

FIG. 9 illustrates a homology model of GIV's SH2 domain.

FIG. 10 shows that GIV is phosphorylated in vitro by RTKs and in cells in response to growth factors.

FIG. 12 shows that the GEF domain is not required for tyrosine phosphorylation of GIV.

FIG. 13 shows that GIV interacts with p85α (PI3K) and EGFR upon growth factor stimulation.

Figure 1B:
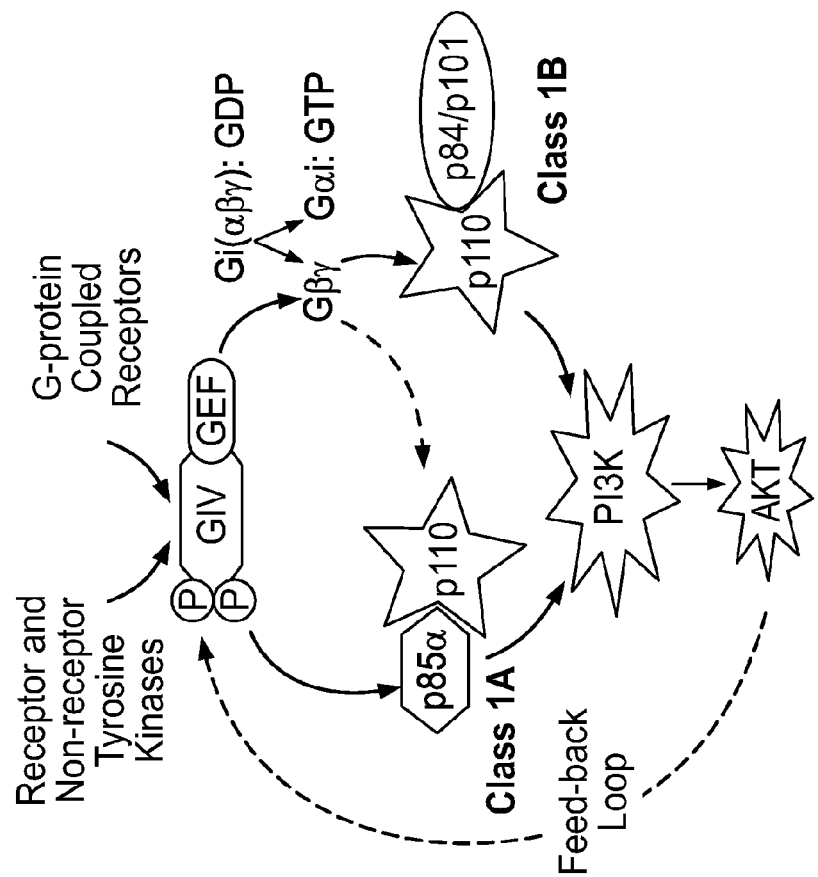
FIG. 1B provides a detailed model for the enhancement of Class 1 PI3K by GIV. GIV's phosphotyrosines directly interact with and activate Class 1A PI3Ks that are regulated by p85α-subunits (solid, left arrow). Akt-dependent phosphorylation of GIV on S1416 requires GIV-dependent activation of the PI3K-Akt pathway but not vice versa. The enhancement of the PI3K-Akt pathway via tyrosine phosphorylated GIV occurs therefore upstream of Akt-mediated phosphorylation of GIV at S1416. The latter event subsequently triggers a "feedback loop" (interrupted, left arrow). GIV's GEF motif activates Gi, releases 'free Gβγ-subunits, which in turn directly interact and activate the catalytic p110γ-subunits of the Class 1B PI3Ks that are regulated by p84/p101-subunits (solid, right arrow). The Gβγ-pathway can additionally bind and activate the catalytic p110β-subunits of Class 1A PI3Ks (interrupted, right arrow). Thus, GIV enhances Class 1(A+B) PI3Ks both directly via its phosphotyrosines and indirectly via Gβγ; two processes that synergistically amplify the resultant PI3K activity at the PM.

were serum starved (−) and subsequently treated with 50 nM EGF prior to lysis. Equal aliquots of lysates (bottom) were incubated with preimmune (lane 1) or anti-GIV CT (lanes 2-5) IgGs and protein A agarose beads Immune complexes (top) were analyzed for endogenous GIV and p85α by immunoblotting (IB). p85α was detectable in GIV-bound complexes after EGF stimulation but not in starved cells (compare lanes 2 and 3), undetectable in cells expressing SHP-1 WT, but restored in cells expressing SHP-1 C453S.

FIG. 22 shows that SHP-1 inhibits GIV's ability to enhance Akt phosphorylation. (A, B) Wild-type (WT), but not the catalytically inactive C453S (CS) mutant of SHP-1 inhibits GIV-dependent Akt phosphorylation. (A) COS7 cells were transfected with empty vector (lane 1), GIV-FLAG alone (lane 2), GIV-FLAG and HA-SHP-1 WT (lane 3), or GIV-FLAG and HA-SHP-1 CS (lane 4). Cells were maintained in the presence of 2% FBS for 20 h prior to lysis. Equal aliquots of whole cell lysates were analyzed for FLAG, HA (HA-SHP-1), phospho-Akt (pAkt), actin and tubulin by immunoblotting. Akt phosphorylation at S473 (pAkt) was increased in cells expressing GIV-FLAG (compare lanes 1 and 2), decreased in cells co-expressing GIV-FLAG and SHP-1 WT (lane 3), and increased in cells co-expressing GIV-FLAG and SHP-1 CS (lane 4). (B) Bar graphs showing quantification of pAkt: actin ratios in A expressed as fold increase compared to vector control. Quantifications were performed by band densitometry using LiCOR Odyssey Infrared Imager. Results are shown as mean+/−SEM (n=5). (C) Depletion of SHP-1 enhances Akt phosphorylation at 5 min after EGF stimulation. HeLa cells treated with scrambled (lanes 1-3) or SHP-1 (lanes 4, 5) siRNA were serum starved and subsequently stimulated with EGF for 5 and 15 min. Equal aliquots of whole cell lysates were analyzed for phosphorylated Akt (pAkt), phosphorylated ERK (pERK1/2), SHP-1 and tubulin by immunoblotting (IB). pAkt, but not pERK1/2 was specifically and significantly enhanced at both 5 and 15 min after EGF stimulation in SHP-1-depleted cells as compared to control cells (compare lanes 4, 5 with 2, 3), temporally coinciding with the enhancement of tyrosine-phosphorylation of GIV.

Figure 23:
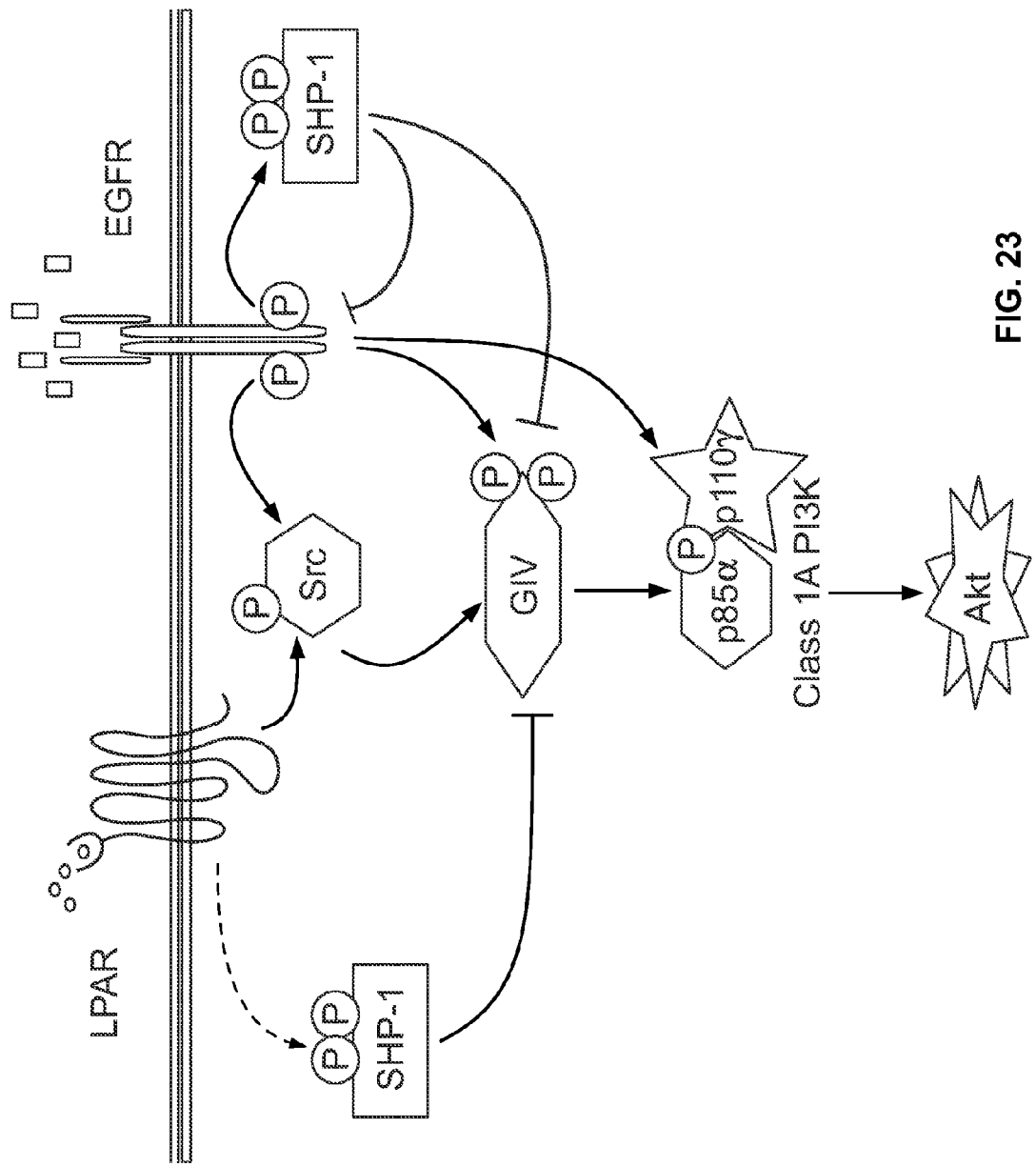

FIG. 23 provides a model of the tyrosine phoshphorylation of GIV, which is triggered by ligands for either RTKs (i.e., EGFR) or GPCRs (i.e., LPAR). Activation of non-RTKs (i.e., Src) downstream of both classes of receptors can also phosphorylate GIV on identical tyrosines (14). Tyrosine-phosphorylated GIV directly binds p85α and activates Class 1 PI3Ks, which in turn activate Akt. SHP-1 protein tyrosine phosphatase is activated downstream of both RTKs and GPCRs. Activated SHP-1 is known to bind and dephosphorylate autophosphorylation site(s) on the cytoplasmic tail of EGFR (19,20), and is known to effectively dephosphorylate substrates of Src kinase (66). Here we demonstrate that SHP-1 binds and dephosphorylates GIV, prevents the formation of GIV-p85α(PI3K) complexes, and thereby inhibits activation of Akt via the GIV-PI3K axis.

Figure 24:
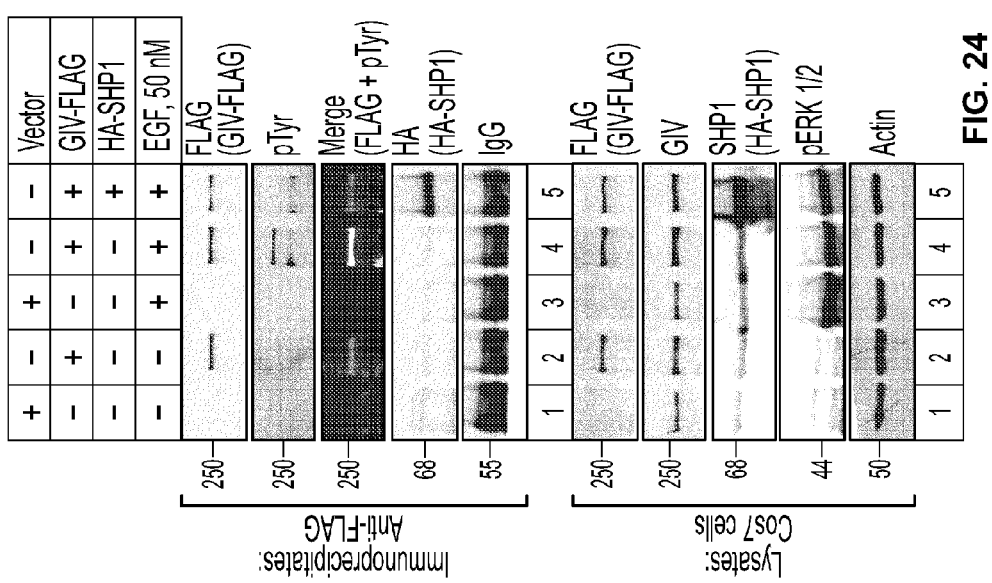

FIG. 24 illustrates that SHP-1 inhibits tyrosine phosphorylation of GIV after stimulation with EGF. COS7 cells transfected with vector alone (lanes 1 and 3), GIV-FLAG alone (lanes 2 and 4), or GIV-FLAG and HA-SHP-1 WT (lane 5) were serum starved (−) and subsequently stimulated with EGF (50 nM, +) for 10 min. Equal aliquots of lysates (bottom) were incubated with anti-FLAG mAb and protein G agarose beads Immune complexes (top) were analyzed by two-color immunoblotting (IB) for GIV and pTyr using the Li-COR Odyssey Infrared Western Blot Imaging System. Single channel images for GIV and pTyr are displayed in grayscale which show that immunoprecipitated GIV was phosphorylated on tyrosine(s) exclusively after EGFR stimulation (compare lanes 2 and 4). Yellow pixels in the overlay of GIV (red) and pTyr (green) images (Merge panels) confirm that GIV was phosphorylated on tyrosine(s) after EGF treatment (lane 4). This EGF-dependent tyrosine phosphorylation of GIV was undetectable in cells co-transfected with HA-SHP-1 (lane 5). Expression of GIV and SHP-1 in all lysates was analyzed by immunoblotting (IB) for FLAG, GIV, SHP-1 and tubulin (bottom).

Figure 25:
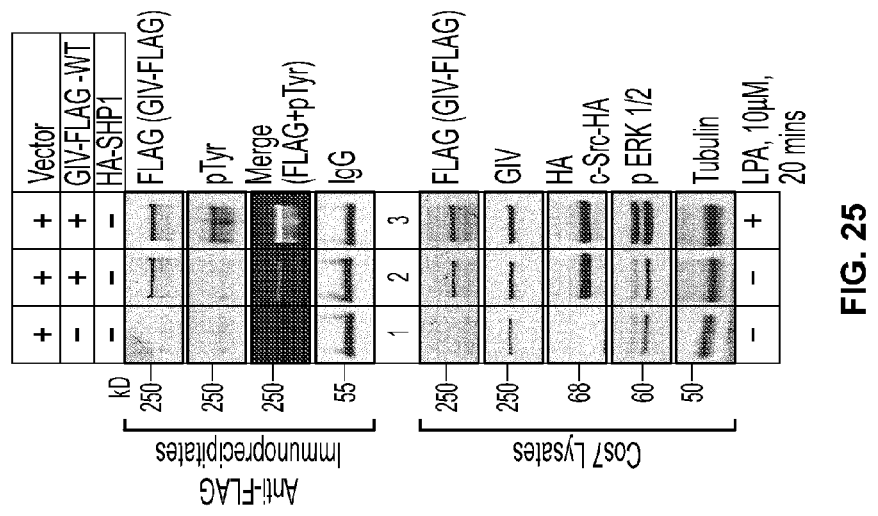

FIG. 25 shows that GIV is tyrosine phosphorylated after stimulation of LPA receptor. COS7 cells transfected with vector alone (lane 1), or co-transfected with Src-HA and GIV-FLAG (lanes 2, 3) were serum starved (−) and subsequently stimulated with 10 μM LPA (+) for 20 min. Equal aliquots of lysates (bottom) were incubated with anti-FLAG mAb and protein G agarose beads Immune complexes (top) were analyzed by two-color immunoblotting (IB) for GIV and pTyr using the Li-COR Odyssey Infrared Western Blot Imaging System. Grayscale image for GIV (top panel) shows that GIV-FLAG is immunoprecipitated in lanes 2 and 3, but not in vector control (lane 1). pTyr panel shows that tyrosine phosphorylation occurred upon ligand stimulation (lane 3). Yellow pixels of the overlaid GIV-FLAG (red) and pTyr (green) images (Merge panel) confirm that the immunoprecipitated GIV-WT is phosphorylated on tyrosine(s) exclusively after LPA treatment (compare lanes 2 and 3). Adequate stimulation of cells by LPA, as determined by activation of ERK1/2, and expression of GIV-FLAG and Src-HA in lysates were analyzed by immunoblotting (IB) for FLAG, GIV, SHP-1, HA (Src-HA), phospho-ERK1/2 and tubulin (bottom).

Figures 26, 27:
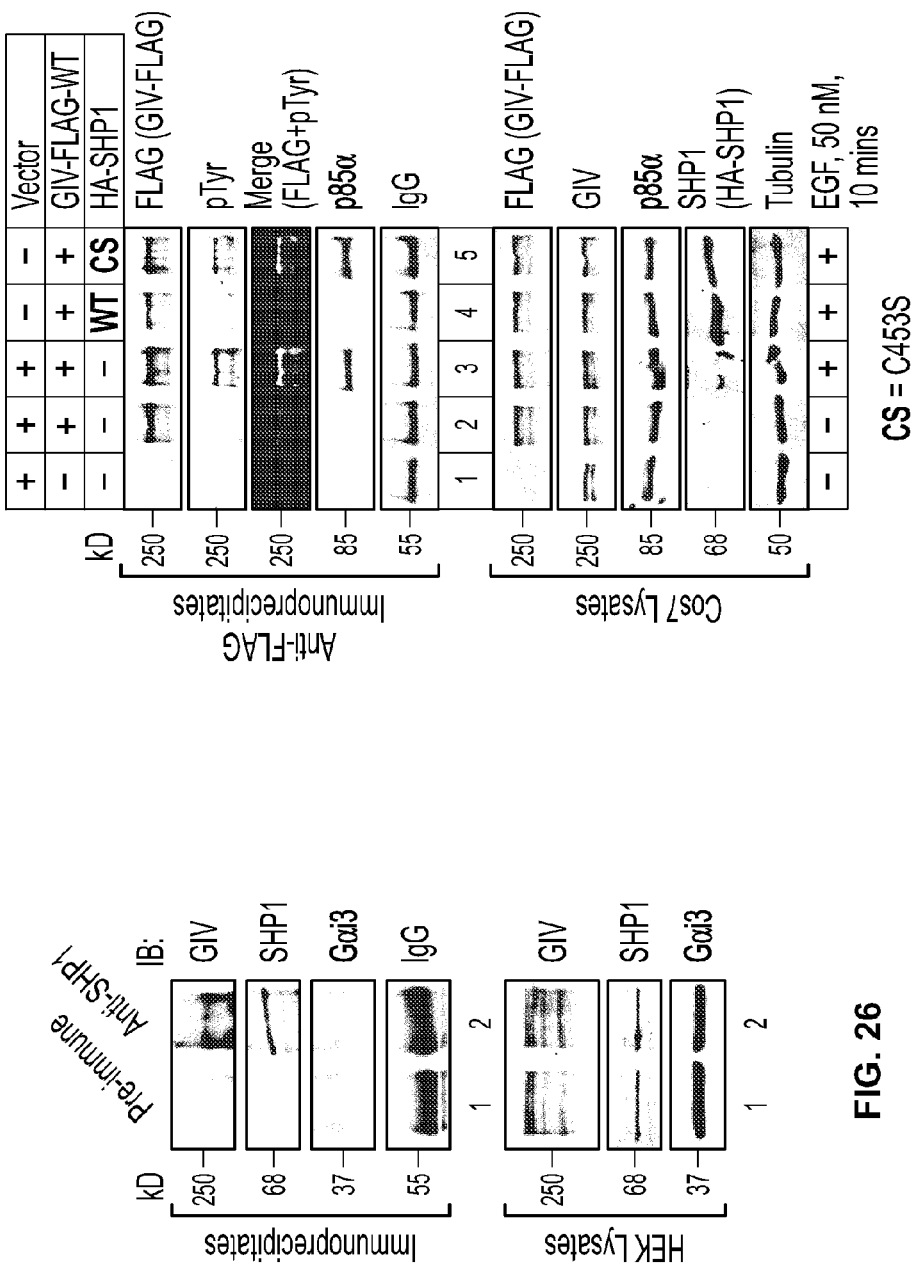

FIG. 26 shows that GIV, but not Gαi3, interacts with SHP-1 in HEK cells. Equal aliquots of HEK lysates (bottom) were incubated with either rabbit preimmune (lane 1) or anti-SHP-1 (lane 2) IgGs, and protein A agarose beads. Lysates and immune complexes (top) were analyzed for GIV, SHP-1, and Gαi3 by immunoblotting (IB). SHP-1 was immunoprecipitated efficiently and specifically by anti-SHP-1 (lane 2), but not control (lane 1) IgG. GIV, but not Gαi3 was detected in SHP-1-bound protein complexes (lane 2).

FIG. 27 shows that Wild-type (WT), but not the catalytically inactive C453S (CS) mutant of SHP-1 inhibits tyrosine phosphorylation of GIV and the formation of phospho-GIV-p85α(PI3K) complexes after EGF stimulation. COS7 cells were transfected with vector alone (lane 1), GIV-FLAG alone (lanes 2, 3), GIV-FLAG and HA-SHP-1 WT (lane 4), or GIV-FLAG and HASHP-1 CS mutant (lane 5). Cells were serum starved (−) and subsequently stimulated with 50 nM EGF (+) for 10 min. Equal aliquots of lysates (bottom) were incubated with anti-FLAG mAb and protein G agarose beads Immune complexes (top) were analyzed by two-color immunoblotting (IB) for GIV and pTyr as well as p85α using the LI-COR Odyssey Infrared Western Blot Imaging System. Grayscale image for GIV (top panel) shows that GIV-FLAG is immunoprecipitated in lanes 2-5, but not in vector control (lane 1). pTyr panel shows that tyrosine phosphorylation occurred upon ligand stimulation (lane 3), undetectable in cells transfected with HA-SHP-1 WT (lane 4), and restored in cells expressing HA-SHP-1 CS (lane 5). Yellow pixels in the overlay of GIV-FLAG (red) and pTyr (green) images (Merge panel) confirm that tyrosine-phosphorylation of GIV is inhibited in the presence of catalytically active SHP-1 (lane 4), but not the catalytically inactive SHP-1 CS (lane 5). Equal aliquots of lysates (bottom) were analyzed for FLAG, GIV, p85α, SHP-1, and tubulin by immunoblotting (IB).

Figure 28:
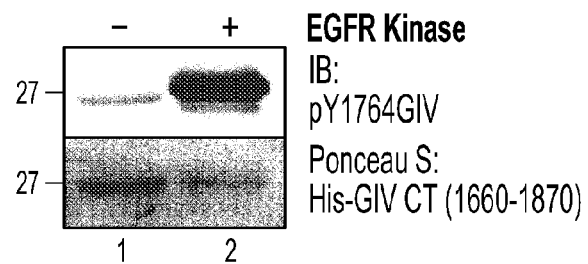

FIG. 28 shows that the pY1764GIV antibody is specific for detecting phosphoGirdin/GIV in immunoblots of phosphoGirdin/GIV produced in an in vitro kinase assay.

Figure 29:
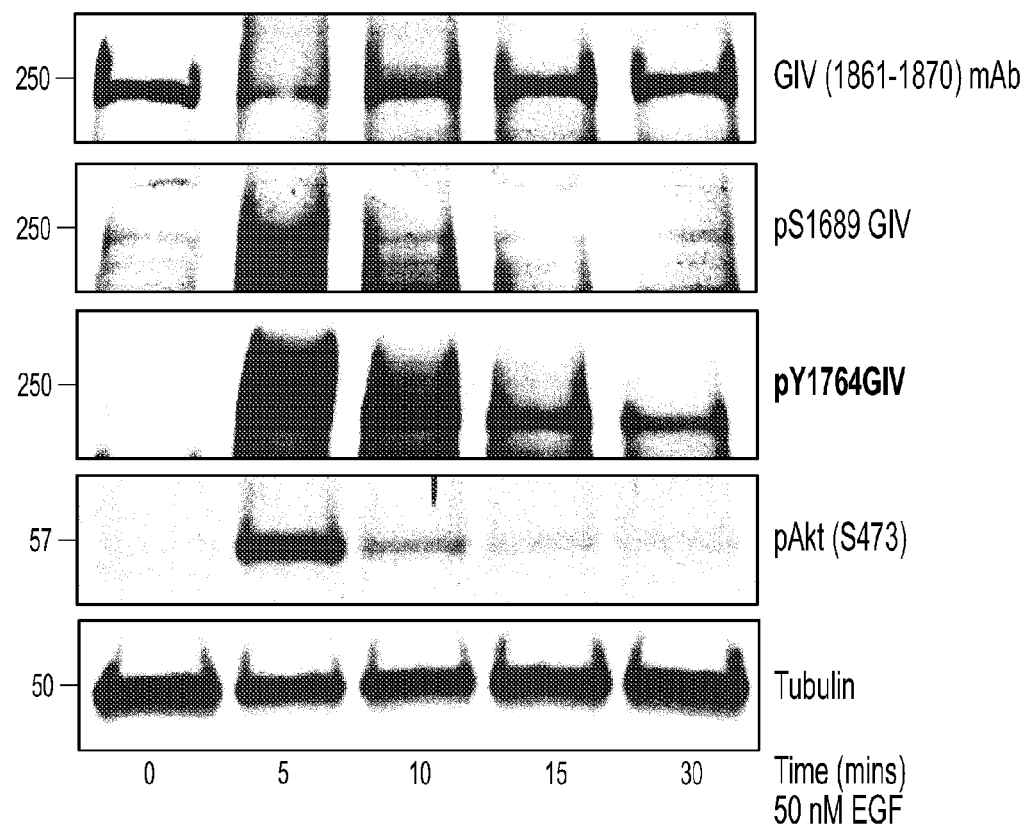

FIG. 29 shows that the pY1764GIV antibody is specific for detecting phosphoGirdin/GIV in immunoblots of HeLa cell lysates. The pY1764GIV antibody is also specific for detecting phosphoGirdin/GIV in whole cells by immunofluorescence and for detecting phosphoGirdin/GIV in breast tumors in situ by immunohistochemistry.

DETAILED DESCRIPTION

The present disclosure generally relates to tyrosine phosphorylation sites of an Akt enhancer (GIV or Girdin), and methods for the detection of the phosphorylated tyrosine residues. In particular, anti-phosphotyrosine antibodies and binding proteins find use in the compositions and methods of the present disclosure.

A GIV phosphotyrosine motif is provided as a marker for PI3K pathway signaling and as a target for therapeutic intervention. Moreover, quantitation of GIV tyrosine phosphorylation permits diagnostic assessments to be made regarding the invasiveness of solid tumors and prognostic assessments to be made regarding disease progression and outcome. Additionally, GIV tyrosine phosphorylation serves as a biomarker for the efficacy of therapeutic regimens affecting PI3K signaling Disruption of the phosphotyrosine-dependent GIV-PI3K interaction inhibits PI3K signaling and therefore provides a viable target for the treatment of cancer.

GIV (Galpha-Interacting, Vesicle-Associated Protein or Girdin)

GIV (Girdin), is a multi-domain protein, which is required for growth factors such as EGF (Enomoto et al., Developmental Cell, 9:389-402, 2005; and Ghosh et al., J Cell Biol, 182:381-393, 2008), IGF (Jiang et al., Cancer Research, 68:1310-1318. 2008), VEGF (Kitamura et al., Nat Cell Biol, 10:329-337, 2008) and insulin (Anai et al., J Biol Chem, 280:18525-18535, 2005; and Garcia-Marcos et al., Proc Natl Acad Sci USA, 106:3178-3183, 2009) to enhance Akt activation in a PI3K-dependent manner, remodel actin and trigger cell migration. GIV is also required for Akt enhancement downstream of G-protein coupled receptors (GPCRs) (Ghosh et al., supra, 2008; Garcia-Marcos et al., supra 2009; and Garcia-Marcos, J Biol Chem, 285:12765-12777, 2010). Working downstream of growth factor receptor tyrosine kinases (RTKs) and GPCRs, GIV serves as a common enhancer of Akt signals during a diverse set of biological processes, e.g., epithelial wound healing, macrophage chemotaxis, development, autophagy, tumor angiogenesis, tumor cell migration, and cancer invasion/metastasis (supra; and Garcia-Marcos et al., FASEB J, 25:590-599, 2011; and Ghosh et al., Mol Biol Cell, 21:2338-2354, 2010).

Recent work has provided some mechanistic insights into these biological functions of GIV. GIV is a non-receptor Guanine-nucleotide Exchange Factor (GEF) for Gαi (Garcia-Marcos et al., Proc Natl Acad Sci USA, 106:3178-3183, 2009), which binds ligand-activated epidermal growth factor receptor (EGFR) (Ghosh et al., Mol Biol Cell, 21:2338-2354, 2010). By linking G protein signaling to EGFR and assembling a Gαi-GIV-EGFR signaling complex, GIV enhances EGFR autophosphorylation, prolongs receptor association with the plasma membrane (PM), and specifically enhances Akt signals to trigger cell migration. Although these studies have established that GIV enhances Akt signaling by operating at the interface between growth factor and G protein signaling, the underlying mechanism of how multiple receptors utilize GIV for Akt-enhancement was not known.

The present disclosure demonstrates that GIV is a novel tyrosine phosphoprotein that directly binds and activates PI3K. Upon ligand stimulation, GIV is phosphorylated at tyrosines 1764 and 1798 by both receptor and non-receptor protein tyrosine kinases, directly binds N- and C-terminal SH2 domains of p85α(PI3K), stabilizes receptor association with PI3-kinase, and enhances PI3-kinase activity at the plasma membrane to trigger cell migration. Tyrosine phosphorylation of GIV and its association with p85α(PI3-kinase) increases during metastatic progression of breast carcinoma, implicating GIV-dependent PI3-kinase activation in cancer invasion. Thus as determined during development of the present disclosure, multiple receptors activate PI3-kinase via tyrosine phosphorylation of GIV, thereby making the GIV-PI3K interface an effective and attractive target within the PI3K-Akt pathway.

The amino acid sequence of human GIV is provided by GenBank Accession No. BAE44387. Tyrosines 1764 and 1798 are shown in bold, while the putative SH2-like domain (aa1623-1870) is italicized:

```
                                                         (SEQ ID NO: 1)
  1 MENEIFTPLL EQFMTSPLVT WVKTFGPLAA GNGTNLDEYV ALVDGVFLNQ VMLQINPKLE

61 SQRVNKKVNN DASLRMHNLS ILVRQIKFYY QETLQQLIMM SLPNVLIIGK NPFSEQGTEE

121 VKKLLLLLLG CAVQCQKKEE FIERIQGLDF DTKAAVAAHI QEVTHNQENV FDLQWMEVTD

181 MSQEDIEPLL KNMALHLKRL IDERDEHSET IIELSEERDG LHFLPHASSS AQSPCGSPGM

241 KRTESRQHLS VELADAKAKI RRLRQELEEK TEQLLDCKQE LEQMEIELKR LQQENMNLLS

301 DARSARMYRD ELDALREKAV RVDKLESEVS RYKERLHDIE FYKARVEELK EDNQVLLETK

361 TMLEDQLEGT RARSDKLHEL EKENLQLKAK LHDMEMERDM DRKKIEELME ENMTLEMAQK

421 QSMDESLHLG WELEQISRTS ELSEAPQKSL GHEVNELTSS RLLKLEMENQ SLTKTVEELR

481 TTVDSVEGNA SKILKMEKEN QRLSKKVEIL ENEIVQEKQS LQNCQNLSKD LMKEKAQLEK

541 TIETLRENSE RQIKILEQEN EHLNQTVSSL RQRSQISAEA RVKDIEKENK ILHESIKETS

601 SKLSKIEFEK RQIKKELEHY KEKGERAEEL ENELHHLEKE NELLQKKITN LKITCEKIEA

661 LEQENSELER ENRKLKKTLD SFKNLTFQLE SLEKENSQLD EENELRRNV  ESLKCASMKM
```

```
 721 AQLQLENKEL ESEKEQLKKG LELLKASFKK TERLEVSYQG LDIENQRLQK TLENSNKKIQ

781 QLESELQDLE MENQTLQKNL EELKISSKRL EQLEKENKSL EQETSQLEKD KKQLEKENKR

841 LRQQAEIKDT TLEENNVKIG NLEKENKTLS KEIGIYKESC VRLKELEKEN KELVKRATID

901 IKTLVTLRED LVSEKLKTQQ MNNDLEKLTH ELEKIGLNKE RLLHDEQSTD DRYKLLESKL

961 ESTLKKSLEI KEEKIAALEA RLEESTNYNQ QLRQELKTVK KNYEALKQRQ DEERMVQSSP

1021 PISGEDNKWE RESQETTREL LKVKDRLIEV ERNNATLQAE KQALKTQLKQ LETQNNNLQA

1081 QILALQRQTV SLQEQNTTLQ TQNAKLQVEN STLNSQSTSL MNQNAQLLIQ QSSLENENES

1141 VIKEREDLKS LYDSLIKDHE KLELLHERQA SEYESLISKH GTLKSAHKNL EVEHRDLEDR

1201 YNQLLKQKGQ LEDLEKMLKV EQEKMLLENK NHETVAAEYK KLCGENDRLN HTYSQLLKET

1261 EVLQTDHKNL KSLLNNSKLE QTRLEAEFSK LKEQYQQLDI TSTKLNNQCE LLSQLKGNLE

1321 EENRHLLDQI QTLMLQNRTL LEQNMESKDL FHVEQRQYID KLNELRRQKE KLEEKIMDQY

1381 KFYDPSPPRR RGNWITLKMR KLIKSKKDIN RERQKSLTLT PTRSDSSEGF LQLPHQDSQD

1441 SSSVGSNSLE DGQTLGTKKS SMVALKRLPF LRNRPKDKDK MKACYRRSMS MNDLVQSMVL

1501 AGQWTGSTEN LEVPDDISTG KRRKELGAMA FSTTAINFST VNSSAGFRSK QLVNNKDTTS

1561 FEDISPQGVS DDSSTGSRVH ASRPASLDSG RTSTSNSNNN ASLHEVKAGA VNNQSRPQSH

1621 SSGEFSLLHD HEAWSSSGSS PIQYLKRQTR SSPVLQHKIS ETLESRHHKI KTGSPGSEVV

1681 TLQQFLEESN KLTSVQIKSS SQENLLDEVM KSLSVSSDFL GKDKPVSCGL ARSVSGKTPG

1741 DFYDRRTTKP EFLRPGPRKT EDTYFISSAG KPTPGTQGKI KLVKESSLSR QSKDSNPYAT

1801 LPRASSVIST AEGTTRRTSI HDFLTKDSRL PISVDSPPAA ADSNTTAASN VDKVQESRNS

1861 KSRSREQQSS.
```

Antibodies

In some embodiments isolated antibodies are provided that specifically bind to an epitope comprising phosphorylated GIV tyrosine residues Y1764 or Y1798. In one embodiment the isolated antibody specifically binds an epitope comprising the phosphorylated GIV tyrosine residue Y1764. In another embodiment the isolated antibody specifically binds an epitope comprising the phosphorylated GIV residue Y1798. In another embodiment the isolated antibody specifically binds an epitope comprising the phosphorylated GIV tyrosine residues Y1764 and Y1798. Specifically binding antibodies may have a 10, 30, 100, 300, 1,000, 3,000, 10,000, 30,000, 100,000, 300,000, or 1,000,000-fold greater binding affinity for the phosphorylated epitopes than for the unphosphorylated epitopes.

Immunization.

A mammal (e.g., rodent) can be immunized with a purified or enriched preparation of an antigen and/or recombinant protein antigen, or cells expressing the protein antigen, or a fusion protein of the antigen as described (Lonberg et al., Nature 368:856-859, 1994; Fishwild et al., Nature Biotechnology, 14:845-851, 1996; and PCT Publication Nos. WO 98/24884 and WO 01/14424). For example, a purified or recombinant preparation (5-50 μg) of antigen can be used to immunize the mice intraperitoneally when the mice reach 6-16 weeks of age. Mice typically respond when initially immunized intraperitoneally (IP) with antigen in complete Freund's adjuvant, followed by every other week IP immunizations with antigen in incomplete Freund's adjuvant. However, adjuvants other than Freund's are also found to be effective. The immune response is monitored over the course of the immunization protocol with plasma samples. The plasma can be screened by ELISA and mice with sufficient titers can be used for fusions. Mice can be boosted intravenously with antigen, for example 3 days before sacrifice and removal of the spleen. It is expected that 2-3 fusions for each immunization may need to be performed. Between 6 and 24 mice are typically immunized for each antigen.

Generation of Hybridomas Producing Monoclonal Antibodies.

To generate hybridomas producing monoclonal antibodies, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC No. CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie, Md.). Cells are plated at approximately $2 \times 10^5$ in flat bottom microtiter plate, followed by a two week incubation in selective medium containing 20% fetal Clone Serum, 18% "653" conditioned media, 5% origin (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be re-plated, screened again, and if still positive, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies.

Antibodies of this disclosure also can be produced in a host cell transfectoma using, for example, a combination of recombinant DNA techniques and gene transfection methods as is well known in the art (Morrison, Science, 229: 1202, 1985). For instance to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described (Goeddel, Gene Expression Technology, in Methods in Enzymology 185, Academic Press, San Diego, Calif., 1990). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., Mol Cell Biol, 8:466-472, 1988).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216; 4,634,665; and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood, Immunology Today, 6:12-13, 1985).

Preferred mammalian host cells for expressing the recombinant antibodies of this disclosure include Chinese Hamster Ovary (CHO cells, including dhfr⁻ CHO cells, Urlaub and Chasin, *Proc Natl Acad Sci USA,* 77:4216-4220, 1980; and Kaufman and Sharp, *J Mol Biol,* 159:601-621, 1982), NSO myeloma cells, COS cells and SP2 cells. In particular, for use with NSO myeloma cells, another preferred expression system is the GS gene expression system (See, e.g., Publication Nos. WO 87/04462; WO 89/01036 and EP 338,841). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Production of Monoclonal Antibodies Using Phage Display Methods.

In another embodiment, antibodies are prepared using a combination immunized-mammal and phage display techniques (U.S. Pat. No. 6,794,132 to Buechler et al.). More specifically, the method first involves raising an antibody response in a mammal by immunizing the mammal with an antigen of interest, in this case a polypeptide comprising: the phosphorylated amino acid sequence of SEQ ID NO:5 (pYFISS), the phosphorylated amino acid sequence of SEQ ID NO:2, the phosphorylated amino acid sequence of SEQ ID NO:6 (pYATLP), or the phosphorylated amino acid sequence of SEQ ID NO:3. Next, nucleic acids encoding the antibody chains from lymphatic cells are isolated and introduced into a display vector (e.g., phage) to provide a library of display packages. Thus, each library member comprises a nucleic acid encoding a antibody chain and each antibody chain is displayed from the display package. Such phage display methods for isolating antibodies are established in the art (See, e.g., U.S. Pat. Nos. 5,223,409, 5,403,484, and U.S. Pat. No. 5,571,698 to Ladner et al.; U.S. Pat. Nos. 5,427,908 and 5,580,717 to Dower et al.; U.S. Pat. Nos. 5,885,793, 6,521,404, 6,544,731, 6,555,313, 6,582,915 and U.S. Pat. No. 6,593,081 to Griffiths et al.; U.S. Pat. Nos. 5,969,108 and 6,172,197 to McCafferty et al.; U.S. Pat. No. 6,248,516 to Winter; and U.S. Pat. Nos. 6,291,158, 6,291, 159, 6,291,160 and U.S. Pat. No. 6,291,161 to Huse et al.). The library then is screened with the antigen of interest to isolate library members that specifically bind to the antigen. Nucleic acid inserts of the selected library members then are isolated and sequenced by standard methods to determine the light and heavy chain variable sequences of the selected antigen binders. The variable regions can be converted to full-length antibody chains by standard recombinant DNA techniques, such as cloning of the variable regions into an expression vector that carries the heavy and light chain constant regions such that the $V_H$ region is operatively linked to the $C_H$ region and the $V_L$ region is operatively linked to the $C_L$ region.

Characterization of Monoclonal Antibody Binding to Antigen.

Antibodies of the present disclosure can be tested for binding to an antigen of interest by, for example, standard flow cytometry methods. Since some antibodies of the present disclosure preferably recognize an antigen in its native conformation within a membrane, testing for binding to the antigen preferably is done with an assay (e.g., flow cytometry) that utilizes a reagent expressing native conformation antigen. Nonlimiting examples of reagents expressing native conformation antigen that can be used in the binding assays include cells that naturally express the antigen, cells that have been transfected to express the antigen and liposomes into which the antigen has been incorporated. Briefly, for the flow cytometry assay, cells expressing the antigen are incubated with the test antibody, washed, incubated with a labeled secondary reagent capable of binding to the test antibody, washed again, and subjected to analysis to detect the binding of the secondary reagent to the cells (e g, using a FACS machine). Preferably, mice that develop the highest titers as evaluated by flow cytometry are used for fusions or for further selection of antibodies. A flow cytometry assay as described above can also be used to screen for hybridomas that show positive reactivity with the antigen used as an immunogen. Hybridomas expressing antibodies that bind with high avidity to the antigen are subcloned and further characterized. One clone from each hybridoma that retains the reactivity of the parent cells is chosen for making a 5-10 vial cell bank stored at −140° C., and for antibody purification purposes.

To purify anti-antigen antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity The buffer solution can be exchanged into PBS, and the concentration can be determined by OD280 using 1 43 extinction coefficient The monoclonal antibodies can be aliquoted and stored at −80° C. To determine if the selected anti-antigen monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using a whole cell ELISA assay in which microtiter plates are coated with cells expressing the antigen (or in the case of a soluble antigen, coated with recombinant or purified antigen), and the ability of the unlabeled antibody to compete with the biotinylated antibody for binding to the antigen-expressing cells is examined. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either IgG1 or IgM-specific alkaline phosphatase-conjugated probes. Plates are developed and analyzed as described above.

Anti-antigen IgGs can be further tested for reactivity with recombinant or purified antigen by Western blotting. Briefly, antigen can be prepared and subjected to sodium dodecyl sulfate polyacrylamide gel electrophoresis (SDS-PAGE). After electrophoresis, the separated antigens are transferred to nitrocellulose membranes, blocked with 10% fetal calf serum, and probed with the monoclonal antibodies to be tested. IgG binding can be detected using anti-species IgG alkaline phosphatase and developed with BCDVNBT substrate tablets (Sigma Chem Co., St Louis, Mo.).

The binding specificity of an antibody is also determined by monitoring binding of the antibody to cells expressing the antigen, for example by flow cytometry. Typically, a cell line, such as a CHO cell line, is transfected with an expression vector encoding a transmembrane form of the antigen. The transfected protein may comprise a tag, such as a myc-tag, preferably at the N-terminus, for detection using an antibody to the tag. Binding of an antibody of this disclosure to antigen is determined by incubating the transfected cells with the antibody, and detecting bound antibody. Binding of an antibody to the tag on the transfected protein is used as a positive control.

In an exemplary embodiment, an antibody specific for phosphoGirdin/GIV was produced (pY1764GIV antibody). This antibody was determined to be specific for detecting phosphoGirdin/GIV in immunoblots (FIGS. 28 and 29), by immunofluorescence and by immunohistochemistry.

Screening Assays

In some embodiments screening assays for inhibitors of the GIV-PI3K interaction is provided. In one embodiment the screening assay is performed in a cell, such as a eukaryotic cell or a prokaryotic cell. In a specific embodiment the cell-based screening assay comprises a high-content imaging step. In another specific embodiment the cell-based screening assay monitors the recruitment of a GIV construct to the plasma membrane. In another specific embodiment the GIV construct comprises a fluorescent protein such a GFP, RFP, or YFP. In another specific embodiment tyrosine phosphorylation of the cellular GIV construct is triggered by through the activation of a receptor tyrosine or non-receptor tyrosine kinase pathway, such as the EGFR, PDGFR, VEGFR, or InsR pathway. In one embodiment the screening assay is performed using purified proteins. In one embodiment the purified GIV is phosphorylated at tyrosine residues Y1764 or 1798. In one specific embodiment the screening assay using purified proteins is a homogeneous assay, such as a TR-FRET assay. In one specific embodiment the screening assay using purified proteins is a heterogeneous assay, such as an ELISA or SPR assay. In one embodiment the screening assay is an endpoint assay. In another embodiment the screening assay is a kinetic assay. The concentrations of GIV and PI3K constructs may be chosen such that 10%, 20%, 30%, 40%, 50%, 60%, 70%, 80%, 90%, 99%, or 99.9% of the GIV construct or the PI3K construct present in the screening assay forms part of a GIV-PI3K complex.

In one embodiment the screening assay includes the steps of contacting GIV and PI3K constructs in the presence of a test compound or a control compound and performing a procedure for quantitation of the interaction between the GIV and PI3K constructs. In one specific embodiment the GIV construct comprises a 4, 6, 8, 10, 12, 14, 16, 18, 20, 40, 60, 80, 100, 150, 200, or 250 amino acid sequence of GIV and tyrosine residues Y1764 or 1798. In one specific embodiment tyrosine residues Y1764 or 1798 of the GIV construct are phosphorylated. In one specific embodiment, the PI3K construct comprises the N-terminal or C-terminal SH2 domains of PI3K.

In one specific embodiment the test compound includes small molecules, antibodies, protein domains, and peptides. In one specific embodiment, the control compound is a positive control compound or a negative control compound. In one specific embodiment the control compound includes organic solvents such as DMSO, Ethanol, DMF, or Acetone, small molecules, antibodies, proteins or protein domains, such as proteins or protein domains mimicking phosphorylated or unphosphorylated GIV and peptides such as peptide mimics of phosphorylated or unphosphorylated GIV. In one specific embodiment the test compound or control compound are tested at a single concentration. In another specific embodiment the test compound or control compound are tested at a range of different concentrations such as a range from 1 pM to 1 mM. Negative control compounds may inhibit or activate the interaction between GIV and PI3K constructs by 0%, 1%, 2%, 4,%, 6%, 8%, 10%, 15% or 20% as compared to an experimental condition where no control or test compounds are present (100% interaction). Positive control compounds may behave like test compounds that are inhibitors or activators of the GIV-PI3K interaction. Test compounds may include inhibitors or activators of the GIV-PI3K interaction Inhibitors of the GIV-PI3K interaction may inhibit 10%, 20%, 30%, 50%, 60%, 70%, 80%, 90%, or 100% of the interaction between GIV and PI3K constructs as compared to an experimental condition where no control or test compounds are present (100% interaction) Inhibitors of the GIV-PI3K interaction may be irreversible covalent inhibitors or reversible inhibitors. Activators of the GIV-PI3K interaction may increase the interaction between GIV and PI3K constructs by 20%, 40%, 60%, 80%, 100%, 300%, or 1,000% as compared to an experimental condition where no control or test compounds are present.

In one specific embodiment the procedure for quantitation includes optical measurements, such as absorbance, fluorescence, luminescence, or plasmon resonance measurements, thermal measurements, such as isothermal titration calorimetry or differential scanning calorimetry, nuclear magnetic resonance spectroscopy, and mass spectrometry.

The present disclosure provides cellular and purified protein assays to screen for inhibitors of the GIV-PI3K interaction. Generally, detectably labeled molecular constructs including phosphorylated GIV tyrosine residues Y1764 or Y 1789 are contacted with detectably labeled molecular constructs including the N-terminal or C-terminal PI3K domain in the presence and absence of a test compound. An assay signal is subsequently recorded that correlates with the relative amount of GIV-PI3K complex formation. The relative activity of a test compound is determined by comparing the assay signal indicative of relative GIV-PI3K complex formation in the presence of a test compound with the corresponding signal in the absence of the test compound (and preferably in the presence of a control compound). When screening for inhibitors of the GIV-PI3K interaction assay conditions are typically selected such that the assay signal baseline in the presence of the control compound corresponds to 80% or less of the assay signal achievable under conditions where GIV-PI3K complex formation is 100%. Assay conditions that can be varied to achieve different assay signal baselines include protein concentrations of the GIV and PI3K constructs, composition and pH of the protein binding buffer, or the degree of RTK or NRTK pathway activation.

The molecular compound libraries screened include diverse small molecule libraries, known drug collections, and peptide libraries. The compounds are either untargeted or have been preselected through rational, structure guided design efforts or through medicinal chemistry efforts. Typical compound screening concentrations range from 1 nM to 1 mM, but preferred concentrations range from 1 μM and 10 μM. Diverse compound collections are well known in the art and readily accessible through commercial vendors or public screening centers such as the NIH Chemical Genomics Center (see, e.g., Inglese et al., Proc. Natl. Acad. Sci. U.S.A. 103:11473-78, 2006).

A range of assay formats and detection technologies are suitable for the quantitation of GIV-PI3K purified protein complexes, including homogeneous assays, such as (TR-) FRET-based assays, or heterogeneous assays, such as ELISA or SPR-based assays. A range of assay formats and detection technologies are further suitable for the quantitation of GIV-PI3K complexes in a living cell, including (TR-)FRET-based assays or high-content image-based protein translocation assays. Various detectable labels can be used in the screening methods, including fluorescent dyes, such as FITC, or GFP, enzymes such as HRP, or affinity tags such as biotin, $His_6$-, or Flag-tags (see, e.g., Inglese et al., Nat. Chem. Biol. 3:466-79, 2007).

Diagnostic and Prognostic Methods

In some embodiments of the disclosure a method for assessing the risk of metastasis formation by a tumor in a cancer patient is provided. In one embodiment the method comprises the steps of a) subjecting a sample from the tumor to a procedure for quantitation of GIV tyrosine phosphorylation levels and b) detecting the presence of elevated GIV tyrosine phosphorylation levels or normal GIV tyrosine phosphorylation levels in the sample, wherein elevated GIV tyrosine phosphorylation levels are associated with an elevated risk of metastasis formation as compared to the risk of metastasis formation associated with normal GIV tyrosine phosphorylation levels. Normal GIV tyrosine phosphorylation levels may be established by determining GIV phosphorylation levels in an untransformed primary cell, in a cell derived from normal tissue such as 16N (21T series of human mammary cells), or in a tissue sample, such as a biopsy, derived from a healthy human subject or from the healthy tissue of a cancer patient. GIV tyrosine phosphorylation levels equal to or greater than 2-fold normal levels, such as 2, 3, 4, 5, 6, 7, 8, 9, 10, 30, 100, 300, or 1,000-fold greater than normal levels are elevated GIV tyrosine phosphorylation levels. Normal levels of GIV tyrosine phosphorylation are typically associated with a risk of metastasis formation equal to the risk that metastases would be formed by an untransformed primary cell, a cell derived from normal tissue, such as 16N (21T series of human mammary cells), or a cell derived from a healthy human subject. Elevated levels of GIV tyrosine phosphorylation are typically associated with risks of metastasis formation comparable to the risk presented by primary tumor cells such as NT cells (21T series of human mammary cells, invasive ductal carcinoma cells) or even metastatic MT2 cells (21T series, collected from metastatic pleural effusions).

In one embodiment the elevated risk of metastasis formation in a patient is associated with a worse prognosis of disease progression or outcome than the normal risk of metastasis formation. Disease progression or outcome may be measured by factors including median survival times, median tumor free survival times, responsiveness to cancer treatments, such as effects on tumor burdens, or quality of life parameters, such as physical pain, physical discomfort, or mental depression.

In one embodiment the tumor is a solid tumor. In one embodiment the solid tumor is a manifestation of a cancer including breast cancer, lung cancer, kidney cancer, liver cancer, colon cancer, pancreatic cancer, ovarian cancer, testicular cancer, prostate cancer, head and neck cancer, skin cancer, brain cancer, lymphatic cancer or brain cancer. Possible cancer patients are human, mouse, rat, dog, cat, monkey, horse, hamster, or rabbit patients.

In one embodiment the procedure for quantitation of GIV tyrosine phosphorylation levels comprises the step of contacting the sample from the solid tumor with an isolated antibody that specifically binds to phosphorylated GIV tyrosine residues. In one specific embodiment the procedure comprises an antibody-based detection method such as immunohistochemistry, antibody microarray, ELISA, western blotting, or magnetic resonance imaging. In another embodiment the procedure comprises the step of contacting the sample from the solid tumor with a phosphospecific protein binding domain. The phosphospecific protein binding domain may have a 3, 10, 30, 100, 300, 1,000, 3,000, 10,000, 30,000 or 100,000-fold greater binding affinity to GIV phosphorylated at residues Y1764 or Y1798 than to GIV not phosphorylated to GIV residues Y1764 and Y1798. In a specific embodiment the phospospecific protein binding domain comprises a SH2 domain. In another specific embodiment the phosphospecific protein binding domain comprises the N-terminal or C-terminal SH2 domain of PI3K.

Biomarkers

In some embodiments of the disclosure a method for assessing the efficacy of a treatment in a patient in need thereof is provided. In one embodiment the method comprises the steps of a) obtaining a tissue sample from the patient at a time before the treatment is provided, b) providing the treatment, c) obtaining a tissue sample from the patient at a time after the treatment is provided, d) subjecting the tissue sample to a procedure for quantitation of GIV tyrosine phosphorylation levels, and d) detecting the presence of reduced, unchanged, or elevated GIV tyrosine phosphorylation levels in the tissue sample of step c) as compared to the tissue sample of step a). Unchanged GIV tyrosine phosphorylation levels are associated with a non-efficacious treatment. Reduced GIV tyrosine phosphorylation levels are associated with an efficacious treatment with an inhibitor of the GIV-PI3K interaction. Elevated GIV tyrosine phosphorylation levels are associated with an efficacious treatment with an activator of the GIV-PI3K interaction. Reduced levels of GIV tyrosine phosphorylation in the tissue sample of step c) may be reduced by 20%, 30%, 40%, 50%, 60%, 70%, 80%, 90%, or 100% as compared to GIV tyrosine phosphorylation levels in the tissue sample of step a). Elevated levels of GIV tyrosine phosphorylation in the tissue sample of step c) may be elevated 1.2, 1.4, 1.6, 1.8, 2.0, 4, 6, 8, 10, 30, 100, 300, 1,000, 3,000, or 10,000-fold as compared to GIV tyrosine phosphorylation levels in the tissue sample of step a). Unchanged levels of GIV tyrosine phosphorylation in the tissue sample of step c) may be reduced by 0%, 2%, 4%, 8%, 12%, or 16% or elevated by 1.1 fold as compared to GIV tyrosine phosphorylation levels in the tissue sample of step a).

In one embodiment the treatment is a treatment with inhibitors of the GIV-PI3K interaction. In another embodiment the treatment is a treatment with activators of the GIV-PI3K interaction.

In one embodiment the treatment is a treatment for disease conditions including breast cancer, lung cancer, kidney cancer, liver cancer, colon cancer, pancreatic cancer, ovarian cancer, testicular cancer, prostate cancer, head and neck cancer, skin cancer, brain cancer, lymphatic cancer, brain cancer, obesity, diabetes, metabolic syndrome, transplant rejection, and wound healing.

In one embodiment the treatment comprises providing an inhibitor of a tyrosine kinase such as EGFR, VEGFR, PDGFR, Kit, CSF1R, INSR, TRKA, IGFR, HER2, FGFR, HGFR, EPHR, AXL, ALK/LTK, ITK, TIE, ROR, DDR, RET, or KLG, RYK, MuSK, a non-receptor tyrosine kinase such as SRC, LCK, HCK, YES1, ABL, or JAK, PI3K, AKT or a PI3K-coupled GPCR. Possible inhibitors include small molecule inhibitors, inhibitory oligonucleotides such as siRNA, RNAi, and microRNA, antagonistic antibodies or RNA aptamers, neutralizing antibodies, RNA aptamers, or decoy receptors, small molecule GPCR inhibitors, partial GPCR antagonists, or reverse GPCR agonists.

In one embodiment the treatment comprises providing an activator of a tyrosine kinase such as EGFR, VEGFR, PDGFR, Kit, CSF1R, INSR, TRKA, IGFR, HER2, FGFR, HGFR, EPHR, AXL, ALK/LTK, ITK, TIE, ROR, DDR, RET, or KLG, RYK, MuSK, a non-receptor tyrosine kinase such as SRC, LCK, HCK, YES1, ABL, or JAK, PI3K, AKT or a PI3K-coupled GPCR. Possible activators include agonistic antibodies, RNA aptamers, small molecule agonists, or partial GPCR agonists.

In one embodiment the procedure for quantitation of GIV tyrosine phosphorylation levels comprises the step of contacting the tissue samples with an isolated antibody that specifically binds to phosphorylated GIV tyrosine residues. In one specific embodiment the procedure for quantitation of GIV tyrosine phosphorylation levels comprises an antibody based detection method such as immunohistochemistry, antibody microarray, ELISA, western blotting, or magnetic resonance imaging. In another embodiment the procedure for quantitation of GIV tyrosine phosphorylation levels comprises the step of contacting the tissue samples with a phosphospecific protein binding domain. In a specific embodiment the phospospecific protein binding domain comprises a SH2 domain. In another specific embodiment the phosphospecific protein binding domain comprises the N-terminal or C-terminal SH2 domain of PI3K.

DEFINITIONS

To facilitate an understanding of the embodiments disclosed herein, a number of terms and phrases are defined below.

As used herein, an intact "antibody" comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcRη) and the first component (Clq) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., 1989 Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv or scFv (See e.g., Bird et al., Science 242:423 426, 1988; and Huston et al., Proc Natl Acad Sci USA, 85:5879-5883, 1988). Such single chain antibodies are included by reference to the term "antibody" Fragments can be prepared by recombinant techniques or enzymatic or chemical cleavage of intact antibodies.

The terms "single-chain Fv" or "scFv" as used herein, refer to antibody fragments that contain the VH and VL domains of an antibody, where these domains are present in a single polypeptide chain. Preferably, the Fv polypeptide further contains a polypeptide linker between the VH and VL domains that enables the scFv to form the desired structure for antigen binding. For a review of scFv see Plückthun in The Pharmacology of Monoclonal Antibodies, vol. 113, Rosenburg and Moore eds., Springer-Verlag, New York, pp. 269-315 (1994).

An "isolated" antibody or immunoglobulin, as used herein, refers to an antibody or immunoglobulin that is substantially free of other components in which such antibodies or immunoglobulin are naturally found. Moreover, an isolated antibody or immunoglobulin may be substantially free of other cellular material and/or chemicals.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Specific binding" refers to preferential binding of an antibody to a specified antigen relative to other non-specified antigens. The phrase "specifically (or selectively) binds" to an antibody refers to a binding reaction that is determinative of the presence of the protein in a heterogeneous population of proteins and other biologics. Typically, the antibody binds with a dissociation constant (KD) of about $1\times10^{-7}$ M or less, more preferably about $1\times10^{-8}$ M or less and even more preferably $1\times10^{-9}$ M or less, and binds to the specified antigen with an affinity that is at least two-fold greater than its affinity for binding to a non-specific antigen (e.g., BSA, KLH, casein) other than the specified antigen or a closely-related antigen. The phrases "an antibody recognizing an antigen" and "an antibody specific for an antigen" are used interchangeably herein with the term "an antibody that binds specifically to an antigen". A predetermined antigen is an antigen that is chosen prior to the selection of an antibody that binds to that antigen.

The phrase "specifically bind(s)" or "bind(s) specifically" when referring to an antibody which has intermediate or high binding affinity, exclusively or predominately, to a target antigen. The phrase "specifically binds to" refers to a binding reaction which is determinative of the presence of a target antigen in the presence of a heterogeneous population of antigens. Thus, under designated assay conditions, the specified binding moieties bind preferentially to a particular target antigen and do not bind in a significant amount to other components present in a test sample. A variety of assay formats may be used to select antibodies that are specifically reactive with a particular antigen. For example, solid-phase ELISA immunoassays, immunoprecipitation, surface plasmon resonance, and Western blot are used to identify antibodies that specifically react with the antigen. Typically a specific or selective reaction will be at least twice background signal or noise and more typically more than 10 fold background signal.

Except when noted, the terms "patient" or "subject" are used interchangeably and refer to mammals such as human patients and non-human primates, as well as experimental animals such as rabbits, rats, and mice, and other animals.

The term "substantially pure" or "isolated" means an object species (e.g. an antibody of the disclosure) has been identified and separated and/or recovered from a component of its environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the disclosure) can also be purified to essential homogeneity (contaminant species cannot be detected in the composition by conventional detection methods) wherein the composition consists essentially of derivatives of a single macromolecular species. For example, an isolated antibody to a human antigen can be substantially free of other antibodies that do not bind to the human antigen of interest (e.g., bind to a different antigen). Further, an isolated antibody that specifically binds to an epitope, isoform or variant of human antigen may, however, have cross-reactivity to other related antigens, e.g., from other species (e.g., species homologs). Moreover, an isolated antibody of the disclosure may be substantially free of other cellular material (e.g., non-immunoglobulin associated proteins) and/or chemicals.

EXAMPLES

The present disclosure is described in further detail in the following examples, which are not in any way intended to limit the scope of the disclosure as claimed. The following examples are offered to illustrate, but not to limit the claimed disclosure.

In the experimental disclosure which follows, the following abbreviations apply: M (molar); mM (millimolar); µM (micromolar); nM (nanomolar); pM (picomolar); mol (moles); mmol (millimoles); µmol (micromoles); nmol (nanomoles); pmol (picomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); miRNA (microRNA); siRNA (small inhibitory RNA); RNAi (inhibitory RNA); OD (optical density); PCR (polymerase chain reaction); and RT-PCR (reverse transcription PCR).

Additional abbreviations include: EGF(R) (Epithelial Growth Factor (Receptor)); GIV (Gα-Interacting, Vesicle-associated protein, Girdin); GPCR (G-protein coupled receptor); LPA (lysophosphatidic acid); PDGF(R) (Platelet Derived Growth Factor (Receptor)); NRTK (Non-Receptor Tyrosine Kinase); RTK (Receptor Tyrosine Kinase); SPR (surface plasmon resonance); TK (tyrosine kinase); TR-FRET (time-resolved fluorescence resonance energy transfer); and VEGF(R) (Vascular Epithelial Growth Factor (Receptor)).

Example 1

Tyrosine Phosphorylated GIV/Girdin Binds and Activates PI3-Kinase During Cell Migration and Tumor Invasion This example describes GIV phosphotyrosine modifications that mediate PI3K binding. Through the formation of GIV-PI3K complexes tyrosine-phosphorylated GIV increases PI3K signaling and promotes cell migration and tumor invasion.

Materials and Methods

Reagents and Antibodies.

Unless otherwise indicated all reagents were of analytical grade and obtained from Sigma-Aldrich (St. Louis, Mo.). Cell culture media were purchased from Invitrogen (Carlsbad, Calif.). Epidermal growth factor (EGF) and Insulin were obtained from Invitrogen and Novagen, respectively. Recombinant EGFR, VEGFR and PDGFRβ kinases were purchased from Cell Signaling. The Src kinase inhibitor, PP2 was obtained from Calbiochem. Silencer Negative Control scrambled (Scr) siRNA and Gαi3 siRNA (Ghosh et al., J. Cell Biol. 182:381-93, 2008) were purchased from Ambion and Santa Cruz, respectively, whereas GIV siRNA (Ghosh et al., J. Cell Biol. 182:381-93, 2008; Ghosh et al., Mol. Biol. Cell, 21:2338-54, 2010; and Garcia-Marcos et al., Proc. Natl. Acad. Sci. USA 106:3178-83, 2009) was custom ordered from Dharmacon. Antibodies against GIV that were used in this work include rabbit serum and affinity purified anti-GIV coiled-coil IgG (GIV-ccAb; for immunoblotting only) raised against the coiled coil domain of GIV (Ghosh et al., J. Cell Biol. 182:381-93, 2008; Ghosh et al., Mol. Biol. Cell, 21:2338-54. 2010; and Garcia-Marcos et al., Proc. Natl. Acad. Sci. USA 106:3178-83, 2009), and affinity purified anti-Girdin C-terminus (GIV-CTAb; for immunoprecipitation) raised against the last 19 aa of GIV's C-terminus (IBL America, Minnesota and Santa Cruz Biotechnology). To visualize total EGFR by immunofluorescence, mAb #225 raised against the ectodomain (Gill et al., J. Biol. Chem. 259:775-60, 1984) or pAb anti-EGFR (Santa Cruz). Mouse monoclonal antibodies (mAb) against phosphotyrosine (pTyr, BD Bioscsiences, Cat#610000), FLAG (Sigma, for immunoprecipitation), polyhistidine (Sigma), GFP (Living Colors, Invitrogen), HA (Covance), and tubulin (Sigma) were purchased from commercial sources. Rabbit polyclonal antibodies (Rpc) against FLAG (Invitrogen; for immunoblotting), p85α (Millipore Inc.), Gαi3 (M-14; Santa Cruz Biotechnology), phospho-Akt S473 (Cell Signaling), pan-G13 (Santa Cruz Biotechnology), and phospho-ERK 1/2 (Cell Signaling) were obtained commercially. mAb anti-mouse and anti-rabbit Alexa-594- and Alexa-488-coupled goat secondary antibodies for immunofluorescence were purchased from Invitrogen. Goat anti-rabbit and goat anti-mouse Alexa Fluor 680 or IRDye 800 F(ab')2 for immunoblotting were from Li-Cor Biosciences (Lincoln, Nebr.). Control mouse and rabbit IgGs for immunoprecipitations were purchased from BioRad (Hercules, Calif.) and Sigma (St. Louis, Mo.), respectively.

Plasmid Constructs and Mutagenesis.

Cloning of Gαi3 and GIV into pGEX-4T-1 or pET28b was described previously (Garcia-Marcos et al., Proc Natl. Acad. Sci. USA 106:3178-83, 2009). GST-EGFR-T (aa 1046 to 1210) were cloned into pGEX-4T-1 based on the reported sequence (NM_005228) (Garcia-Marcos et al., supra, 2009). For mammalian expression, C-terminal FLAG-tagged GIV was generated by cloning GIV into p3xFLAG-CMV-14 between NotI and BamH1. RNAi-resistant GIV was generated by silent mutations as described previously (Garcia-Marcos et al., supra, 2009). FLAG-GIV and His-GIV-CT phospho-mutants (Y1764F, Y1798F and Y1764,1798F) were generated by site-directed mutagenesis (sequences of primers available upon request) using Quick-Change kit (Stratagene, San Diego, Calif.) as per manufacturer's protocols. GST-Src (aa 1-257, accession # NM_001025395) was cloned into pGEX-4T-1 between EcoRI and BamH1. C-terminal HA-tagged c-Src for mammalian expression was generated by cloning the entire coding sequence into pcDNA 3.1 between XhoI and EcoRI. The following plasmids/constructs were generous gifts from other investigators: un-tagged-EGFR (Zheng et al., Mol Biol Cell, 15:5538-50, 2004) and GST-TrkA-CT (aa 448-552) construct encoding the 75-amino acid, juxtamembrane region of rat TrkA (Lou et al., Mol Biol Cell 12:615-27, 2001) from M. Farquhar; GST-p85 N and C-SH2 constructs from R. Rajala (Rajala et al., Invest Ophthalmol Vis Sci, 42:3110-3117, 2001); GST-Grb2 and Gab1 from M. Holgado-Madruga (Fixman et al., J Biol Chem, 272:20167-20172, 1997); GFP-Akt-PH from R. Tsien (University of California, San Diego); GFP-Btk-PH from S. Field (University of California, San Diego); GST-PLCγ1 N and C-SH2 from T. Pawson (McGlade et al., Mol. Cell Biol., 12:991-97, 1992); and p85alpha-HA from H. Band (Fukazawa et al., J. Biol. Chem., 270:20177-20182, 1995). All constructs were checked by DNA sequencing.

Protein Expression and Purification.

GST, GST-Gαi3, GST-EGFR-T (aa 1046-1210), GST-TrkA-CT (aa 448-552), the various GST-SH2 adaptors (p85-NSH2, p85-CSH2, Src-SH2, Gab1, Grb2), His-Gαi3, His-GIV-CT WT (aa 1660-1870) and phosphomutants (Y1764F, Y1798F and Y1764,1798F) constructs were expressed and purified from *E. coli* strain BL21(DE3) (Invitrogen) as described previously (Garcia-Marcos et al., J. Biol. Chem., 285:12765-77, 2010), Garcia-Marcos et al., Proc. Natl. Acad. Sci. USA 106:3178-83, 2009). Briefly, cultures of transformed bacteria were induced overnight at 25° C. with 1 mM isopropyl β-D-1-thiogalactopyranoside (IPTG), bacterial pellet from 1 L of culture was re-suspended in 10 ml GST-lysis buffer [25 mM Tris-HCl, pH 7.5, 20 mM NaCl, 1 mM EDTA, 20% (v:v) glycerol, 1% (v:v) Triton X-100, 2× protease inhibitor cocktail (Complete EDTA-free, Roche Diagnostics)] or His-lysis buffer [50 mM NaH$_2$PO$_4$ pH 7.4, 300 mM NaCl, 10 mM imidazole, 1% (v:v) Triton X-100, 2× protease inhibitor cocktail (Complete EDTA-free, Roche Diagnostics)] for GST or His-fused proteins, respectively. After sonication (4×20 s, 1 min between cycles), lysates were centrifuged at 12,000 g at 4° C. for 20 min. Solubilized proteins were affinity purified on glutathione-Sepharose 4B beads (GE Healthcare) or HisPur Cobalt Resin (Pierce). Proteins were eluted, dialyzed overnight against PBS and stored at −80° C. His-Gαi3 was buffer exchanged into G protein storage buffer (20 mM Tris-HCl, pH 7.4, 200 mM NaCl, 1 mM MgCl$_2$, 1 mM DTT, 10 μM GDP, 5% (v:v) glycerol) prior to storage at −80° C.

In Vitro and In Vivo Phosphorylation Assays.

In vitro kinase assays were performed using bacterially expressed His (6×His, hexahistidine) tagged GIV-CT (His-GIV-CT, aa 1660-1870) proteins (~10-15 μg per reaction), and recombinant kinases which were obtained commercially (EGFR, Millipore Inc. and Cell Signaling; c-Src, VEGFR2 and PDGFRβ, Cell Signaling) or expressed in bacteria (GST-TrkA kinase domain). Reactions were started by addition of 200-1000 μM ATP and carried out at 25° C. for 60 min in tyrosine kinase buffer [60 mM HEPES pH 7.5, 5 mM MgCl2, 5 mM MnCl2, 3 μM Na$_3$OV$_4$]. Reactions were stopped by addition of Laemmli's sample buffer and boiling at 100° C. For in vivo phosphorylation assays on endogenous GIV, HeLa cells were serum starved for 12-16 h, pre-incubated with 100 μM sodium orthovanadate for 1 h prior to EGF or insulin stimulation. Reactions were stopped using PBS chilled at 4° C., supplemented with 200 μM sodium orthovanadate, and immediately scraped and lysed for immunoprecipitation. For in vivo phosphorylation assays using overexpressed GIV, FLAG-tagged GIV was co-expressed with untagged EGFR or HA-tagged Src, and at 32 h after transfection cells were processed exactly as the HeLa cells above. For all assays, tyrosine phosphorylations were analyzed by immunoblotting using anti-pTyr mAb (BD Biosciences).

Phosphopeptide Enrichment and LC-MS/MS Analysis.

In vitro-phosphorylated His-GIV-CT protein was resuspended, reduced with TCEP and carboxymethylated with iodoacetamide prior to digestion with trypsin. Samples were then processed as described previously (Guttman et al., Proteomics 9:5016-28, 2009), and the phosphopeptides were enriched using TiO2 (Pinske, Anal. Chem. 76:3935-43, 2004) before their separation and analysis using nano-flow high pressure liquid chromatography (HPLC) coupled with tandem mass spectroscopy (LC-MS/MS) using a QSTAR-Elite hybrid mass spectrometer (ABSciex®). The collected data was searched using Protein Pilot 2.0 (ABSciex®) (Mc Cormack et al., Anal. Chem, 69:767-76, 1997) and MASCOT (Matrix Science®) for sequence identifications.

Cell Culture, Transfection and Lysis.

Unless mentioned otherwise, all cell lines used in this work were cultured according to ATCC guidelines. Transfection was carried out using Genejuice (Novagen) for DNA plasmids or Oligofectamine (Invitrogen) for siRNA oligos following the manufacturers' protocols, and stable cell lines were selected as previously described (Ghosh et al., Mol. Biol. Cell, 21:2338-54, 2010; and Garcia-Marcos et al., Proc. Natl. Acad. Sci. USA 106:3178-83, 2009) using the neomycin analogue, G418 (Cellgro). HeLa cell lines stably expressing GIV-wt (HeLa-GIV-wt), GIV-F1685A mutant (HeLa-GIV-FA) and GIV-Y1764,1798F mutant (HeLa-GIV-YF) were generated and maintained as previously described. All these cell lines were maintained in the presence of G418 (500 μg/ml). Clones were chosen for each construct that had relatively low expression levels of GIV (~2 times the endogenous levels). For each construct, two separate clones were investigated, and similar results were obtained. The 21 T breast cell lines (16N, NT and MT2) were obtained from A. Pardee (Dana-Farber Cancer Institute and Harvard Medical School, Boston, Mass.) (Band et al., Cancer Res. 50:7351-57, 1990; and Qiao et al., Cancer Res. 67:5293-99, 2007).

Lysates used as a source of proteins in immunoprecipitation or pull-down assays were prepared by re-suspending cells in lysis buffer [20 mM HEPES, pH 7.2, 5 mM Mg-acetate, 125 mM K-acetate, 0.4% Triton X-100, 1 mM DTT, supplemented with sodium orthovanadate (500 μM), phosphatase (Sigma) and protease (Roche) inhibitor cocktails], after which they were passed through a 30 G needle at 4° C., and cleared (10-14,000 g for 10 min) before use in subsequent experiments.

Steady-State GTPase Assay.

These assays were done as described previously (Ghosh et al., J. Cell Biol. 182:381-93, 2008; Garcia-Marcos et al., Proc. Natl. Acad. Sci. USA, 106:3178-83, 2009; and Ghosh et al., Mol. Biol. Cell, 21:2338-54, 2010). Briefly, 100 nM of His-Gαi3 was preincubated with different concentrations of sham-treated or in vitro EGFR-phosphorylated His-GIV-CT (aa 1660-1870) for 15 min at 30° C. in assay buffer [20 mM Na-HEPES, pH 8, 100 mM NaCl, 1 mM EDTA, 2 mM $MgCl_2$, 1 mM DTT, 0.05% (w:v) C12E10]. GTPase reactions were initiated at 30° C. by adding an equal volume of assay buffer containing 1 μM [γ-$^{32}$P]GTP (~50 c.p.m/fmol). Duplicate aliquots (50 μl) were removed at 10 min and reactions stopped with 950 μl ice-cold 5% (w/v) activated charcoal in 20 mM $H_3PO_4$, pH 3. Samples were then centrifuged for 10 min at 10,000×g, and 500 μl of the resultant supernatant were scintillation counted to quantify released [$^{32}$P]$P_i$. To determine the specific Pi produced, the background [$^{32}$P]$P_i$ detected at 10 min in the absence of G protein was subtracted from each reaction. The results were expressed either as absolute values of Pi produced.

Immunofluorescence.

Cells were fixed at room temperature with 3% paraformaldehyde for 20-25 min, permeabilized (0.2% Triton X-100) for 45 min and incubated for 1 h each with primary and then secondary antibodies as described previously (Ghosh et al., J. Cell Biol. 182:381-93, 2008). Antibody dilutions were as follows: mAb GFP, 1:500; secondary goat anti-rabbit (594) and goat anti-mouse (488) Alexa-conjugated antibodies, 1:500, and DAPI, 1:2000 (Molecular Probes). Samples were examined with a Zeiss Axiophot microscope (Carl Zeiss Inc., Thornwood, N.Y.) using a 63× aperture (Zeiss Plan Neofluar, 1.30 NA), and images were collected with the ORCA-ER camera Hamamatsu, Bridgewater, N.J.), and Volocity Software. All individual images were processed using Image J software (NIH) and assembled for presentation using Photoshop and Illustrator software (Adobe).

GST-Pulldown and Immunoprecipitation Assays.

These assays were carried out as previously described (Pauptit et al., Acta Crys D 57:1397-04, 2001) with minor modifications. Purified GST-fused proteins (15-20 μg) or GST alone (30 μg) were immobilized on glutathione S-sepharose beads (GE healthcare) and incubated for 4 h at 4° C. in binding buffer (50 mM Tris-HCl, pH 7.4, 100 mM NaCl, 0.4% (v:v) NP-40, 10 mM $MgCl_2$, 5 mM EDTA, 2 mM DTT, and 2 mM Sodium Orthovanadate) containing sham-treated or in vitro phosphorylated His-GIV CT. After 4 h incubation at 4° C. and the beads were washed (4.3 mM $Na_2HPO_4$, 1.4 mM $KH_2PO_4$, pH 7.4, 137 mM NaCl, 2.7 mM KCl, 0.1% (v:v) Tween 20, 10 mM $MgCl_2$, 5 mM EDTA, 2 mM DTT, and 30 and 2 mM Sodium Orthovanadate), and bound proteins eluted in sample buffer for SDS-PAGE. When GST-Gαi3 was used in these assays, both binding and wash buffers were supplemented with 30 μM GDP. Where indicated, His-GIV CT was phosphorylated in vitro using recombinant EGFR kinase (Invitrogen) prior to its use in pulldown assays.

For immunoprecipitations, cell lysates (~1-2 mg protein) were incubated for 4 h at 4° C. with either 2 μg anti-FLAG mAb for immunoprecipitation of GIV-FLAG, anti-GIV-CT (Girdin-T13 Ab, Santa Cruz Biotechnology) for endogenous GIV, anti-HA mAb (Covance) for immunoprecipitation of HA-tagged insulin receptor, anti-EGFR #225 mAb (Ghosh et al., Mol. Biol. Cell, 21:2338-54, 2010) for immunoprecipitation of endogenous EGFR, and their respective pre-immune control IgGs where indicated. Protein A (for GIV-CT Ab) or G (for all other mAbs) agarose beads (GE healthcare) were added and incubated at 4° C. for an additional 60 min. Beads were washed then resuspended and boiled in SDS sample buffer. Buffers were supplemented with 1 mM sodium orthovanadate for all steps of the assay.

Molecular Modeling of the GIV-p85 Interface.

The initial coordinates for C-terminal and N-terminal SH2-domains of p85α were taken from their crystal structures bound to the PDGFRβ peptide, pY$^{751}$VPML and c-Kit phosphotyrosyl peptide (Cuevas et al., J. Biol. Chem. 274:27583-89, 1999; Whitman et al., Nature 332:644-46, 1988; Fry et al., EMBO J. 4:3173-78, 1985; Wang et al., Biochem. J. 408:221-30, 2007; and Zhang et al., Am. J. Physiol. 278, F155-64, 2000), respectively. Structural models of GIV's phosphotyrosine peptides, EDTpY$^{1764}$FISS and SNPpY$^{1798}$ATLP were generated ab initio with ideal covalent geometry. Backbone atoms of the peptides and heavy atoms of the phosphorylated tyrosine side-chain were tethered to their respective counterparts in the PDGFRβ or cKit peptide templates using soft harmonic restraints and subjected to several rounds of Monte Carlo optimization with decreasing tether weight. During the optimization, the backbone conformation of the SH2 domain was held constant while torsional angles controlling the side-chains of both molecules and the backbone of the GIV phosphotyrosine peptide were fully sampled.

PI3-Kinase Assay.

The method used was adapted from the published protocols (Cuevas et al., J. Biol. Chem. 274:27583-89, 1999; Whitman et al., Nature 332:644-46, 1988; Fry et al., EMBO J. 4:3173-78, 1985; Wang et al., Biochem. J. 408:221-30, 2007; and Zhang et al., Am. J. Physiol. 278:F155-64, 2000) with minor modifications. Cos7 cells plated at 80-85% confluency were co-transfected with p85α-HA and either wild-type (WT) or YF mutant of GIV-FLAG. Vector-transfected Cos7 cells were used as controls. 48 h after transfection, cells were lysed in the lysis buffer [20 mM HEPES, pH 7.2, 5 mM Mg-acetate, 125 mM K-acetate, 0.4% Triton X-100, 1 mM DTT, supplemented with sodium orthovanadate (500 μM), phosphatase (Sigma) and protease (Roche) inhibitor cocktails], and equal aliquots of lysates were treated with 2 μg of anti-HA mAb (Covance) for 3 h and protein G agarose beads for 45 min to immunoprecipitate p85α (PI3K). The bead-bound immune complexes (i.e., the immuno-isolated PI3-kinase heterodimers) were subsequently washed two times using each of the four different wash buffers, in the following order: (a) Phosphate-buffered saline, 100 mM Sodium Orthovanadate, 1% Triton X-100; (b) 100 mM Tris/HCl, pH 7.4, 5 mM LiCl and 0.1 mM Sodium Orthovanadate, (c) THE buffer [10 mM Tris/HCl, pH 7.4, 150 mM NaCl, 5 mM EDTA and 0.1 mM Sodium Orthovanadate], and, (d) 20 mM HEPES, pH 7.5, 50 mM NaCl, 5 mM EDTA, 30 mM Sodium Pyrophosphate, 200 mM Sodium Orthovanadate, protease inhibitors, 0.03% Triton X-100. The washed beads were resuspended in 70 μl of buffer (d) and the reaction started by the simultaneous addition of 10 μl of 10×ATP stock solution (65 mM HEPES, pH 7.0, 100 mM $MgCl_2$, 500 μM ATP and 10 μCi [γ-$^{32}$P] ATP (specific activity >5,000 Ci/mmol) and 20 μl of freshly reconstituted 1 mg/ml L-α-Phosphatidylinositol (from bovine liver, Sigma) in 20 mM HEPES pH 7.0, 1 mM EDTA. After incubation for 10 min at room temperature the reactions were terminated by adding 25 μl of 5M HCl and vortexing. Lipids were extracted by addition of 160 μl of a 1:1 mix of methanol:chloroform and vortexing. Organic and water soluble phases were separated by centrifugation for 2 min at room temperature in a microfuge. Equal aliquots of the lower organic phase were loaded immediately onto TLC plates (previously heat activated at 100° C. for 45 min), which were run in a tank equilibrated with the a solvent mixture of chloroform:methanol:water:ammonium hydroxide (60:47:11.3:2) and subsequently analyzed by autoradiography.

Statistical Analysis.

Each experiment presented in the figures is representative of at least three independent experiments. Statistical significance (p value) between various conditions was assessed with the Student's t-test. All graphical data presented was prepared using GraphPad Software, Inc., San Diego, Calif.

Results

GIV is Phosphorylated by Receptor and Non-Receptor Tyrosine Kinases.

Figure 2A:
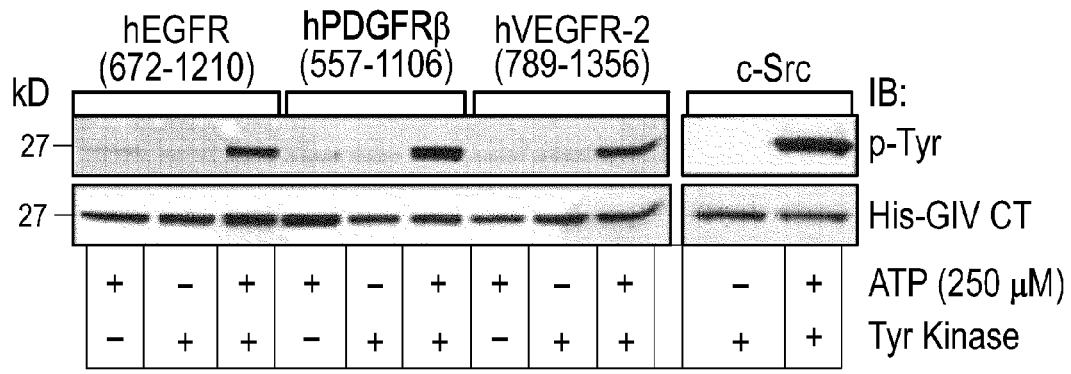
FIG. 2A illustrates that recombinant EGF, VEGF, PDGF receptor and Src tyrosine kinases phosphorylate GIV in vitro. In vitro kinase assays were carried out on equal aliquots of purified His-GIV CT (aa 1660-1870) in the presence or absence of ATP and recombinant tyrosine kinases as indicated. Entire reactions were separated by SDS-PAGE and analyzed for the extent of tyrosine phosphorylation using anti-phosphotyrosine (pTyr) mAb by immunoblotting (IB).
Figure 2B:
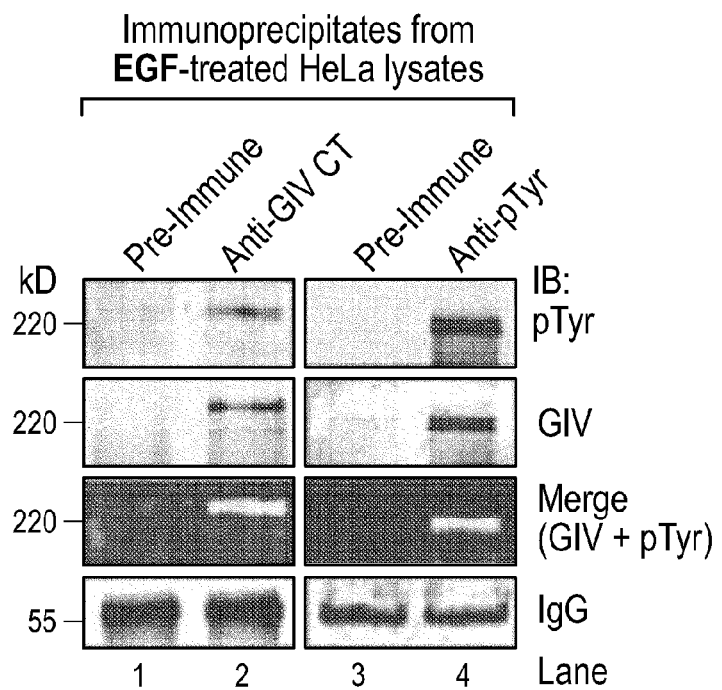
FIG. 2B illustrates that EGF stimulates tyrosine phosphorylation of endogenous GIV. Immunoprecipitation was carried out on lysates from EGF-treated HeLa cells with affinity purified anti-GIV CT Ab (lane 2), anti-phosphotyrosine (pTyr) mAb (lane 4), and their respective preimmune IgGs (lanes 1 and 3). The immune complexes were analyzed by two-color immunoblotting (IB) for GIV (cc Ab) and pTyr using the LICOR Odyssey Infrared Western Blot Imaging System. Single channel images for GIV and pTyr are displayed in grayscale which show that immunoprecipitated GIV is phosphorylated on tyrosine(s) (lane 2) and that GIV is present among pTyr immunoprecipitates (lane 4). Yellow pixels in the overlay of GIV and pTyr (green) images (Merge panels) confirm that GIV is phosphorylated on tyrosine(s) after EGF treatment.
Figures 10A, 10B:
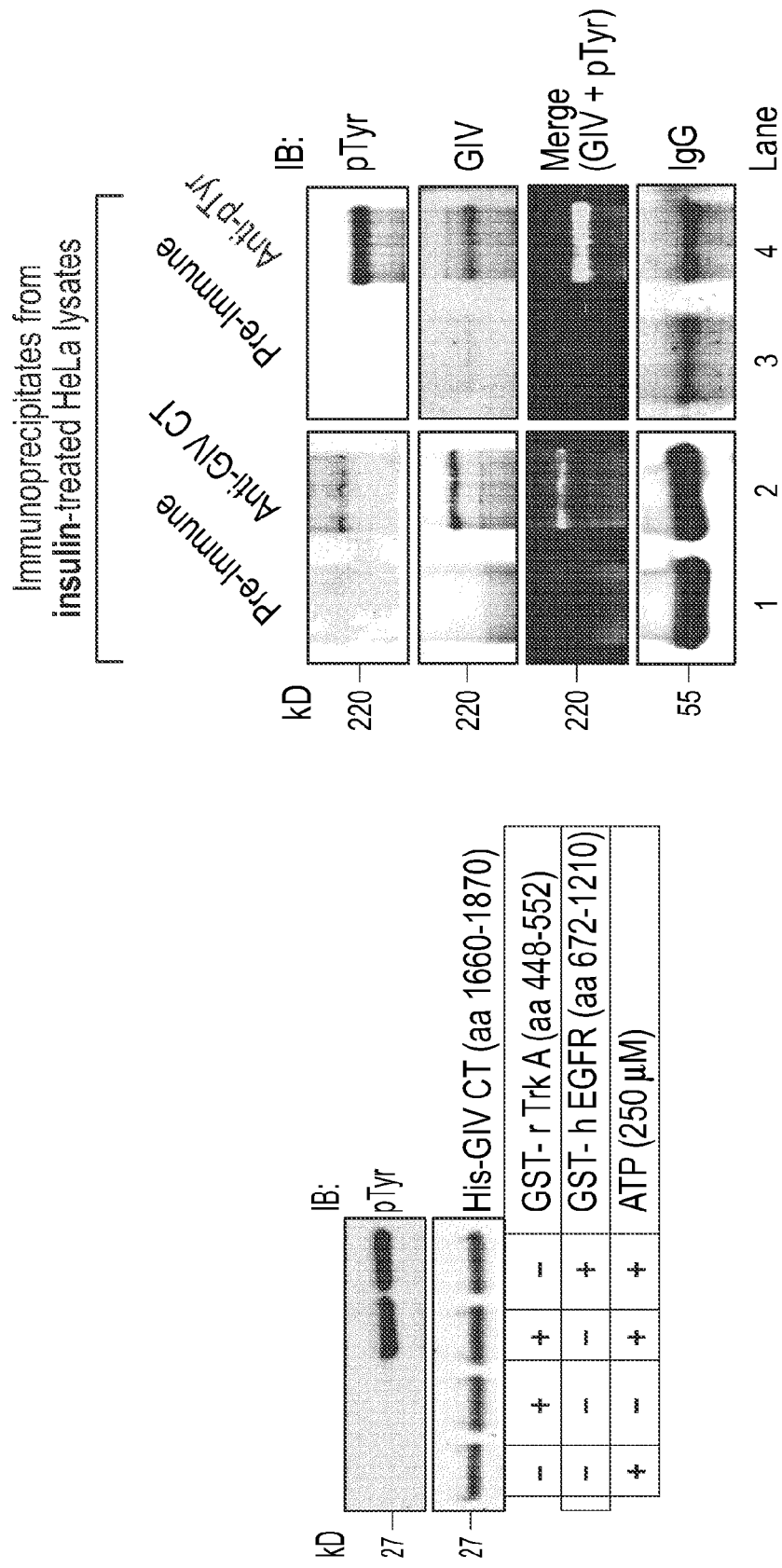
FIG. 10A shows that GIV is phosphorylated in vitro by recombinant TrkA, a NGF (nerve growth factor) receptor tyrosine kinase. Equal aliquots of purified His-GIV CT (aa 1660-1870) were subjected to in vitro kinase assays in the presence or absence of ATP and recombinant, GST-fused EGF and TrkA receptor tyrosine kinases as indicated. Entire reactions were subjected to SDS PAGE and analyzed for the extent of tyrosine phosphorylation using anti-phosphotyrosine (pTyr) mAb by immunoblotting (IB). GIV is phosphorylated on tyrosine(s) by both EGFR and TrkA kinases with equal efficacy.
FIG. 10B shows that insulin stimulates tyrosine phosphorylation of endogenous GIV. Using lysates of insulin-treated HeLa cells as source of GIV, immunoprecipitation was carried out with affinity purified anti-GIV CT rabbit pAb (lane 2), anti-phosphotyrosine (pTyr, lane 4) mAb, and their respective preimmune IgGs (lanes 1 and 3). The immune complexes were subjected to quantitative, two-color, immunoblotting (IB) for GIV (cc Ab) and pTyr using the LI-COR Odyssey Infrared Western Blot Imaging System. Single colored images for GIV and pTyr are displayed in grayscale which show that immunoprecipitated GIV is phosphorylated on tyrosine(s) (lane 2) and GIV is immunoprecipitated by pTyr mAb (lane 4) and that). Yellow pixels in the overlaid images (Merge panels) confirm that GIV is indeed phosphorylated on tyrosine(s) after insulin treatment.

To investigate whether GIV is phosphorylated by tyrosine kinases in vitro, kinase assays were performed using recombinant growth factor RTKs (EGFR, PDGFR, and VEGFR) and His-GIV CT (aa 1660-1870) and the extent of GIV phosphorylation was determined by immunoblotting for phosphotyrosine (pTyr). Specifically GIV's C-terminus was examined because GIV directly binds EGFR tyrosine kinase via this domain (Ghosh et al., Mol Biol Cell 21:2338-54, 2010). All three RTKs robustly phosphorylated GIV to a similar extent (FIG. 2A), as did TrkA, the receptor for nerve growth factor (FIG. 10A). Virtually identical results were obtained when His-GIV CT was subjected to kinase assays with recombinant c-Src, a non-receptor tyrosine kinase (FIG. 2A). To investigate if GIV is tyrosine phosphorylated in cells, endogenous GIV was immunoprecipitated from EGF-treated HeLa cells and immunoblotted for pTyr and GIV. GIV was indeed phosphorylated on tyrosine(s) in cells responding to EGF (FIG. 2B, lanes 1-2). When tyrosine phosphoproteins were immunoprecipitated from HeLa cells using pTyr mAb, GIV was detected in the immunoprecipitates (FIG. 2B, lanes 3-4). Thus, GIV was shown to be a prominent tyrosine phosphoprotein in cells treated with EGF. Identical results were observed in HeLa cells also after insulin stimulation (FIG. 10B). Consequently, GIV is a bona fide tyrosine phosphoprotein, which is a common target of receptor and non-receptor TKs.

Figure 2C:
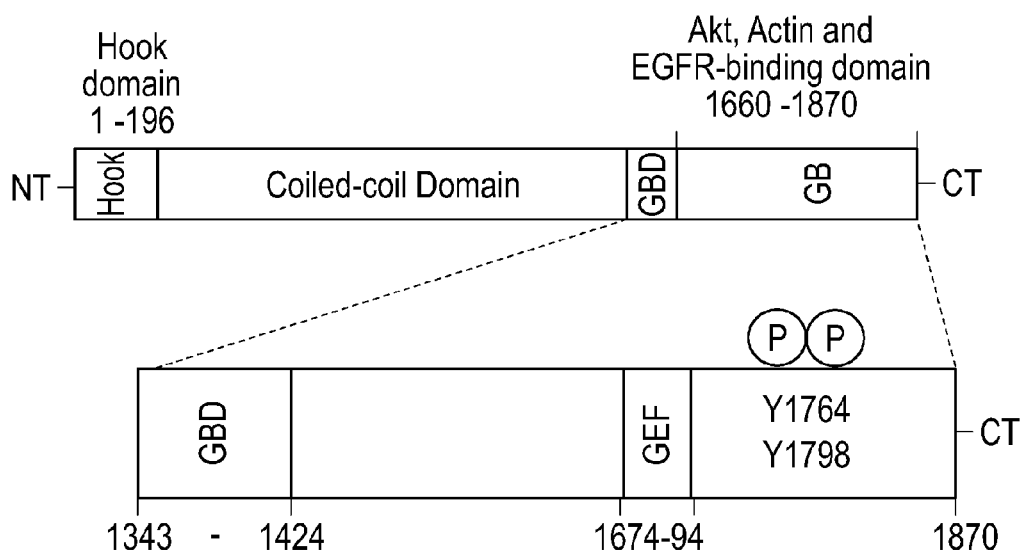
FIG. 2C provides a schematic representation of GIV showing the location of the phosphotyrosines 1764 and 1798. These tyrosines are located in the C-terminus ~70 aa downstream of the GEF motif, within the EGFR, Akt and Actin-binding domains. Other domains include a microtubule-binding hook domain, a coiled-coil homodimerization domain, and a Gα-binding domain (GBD).
Figure 8:
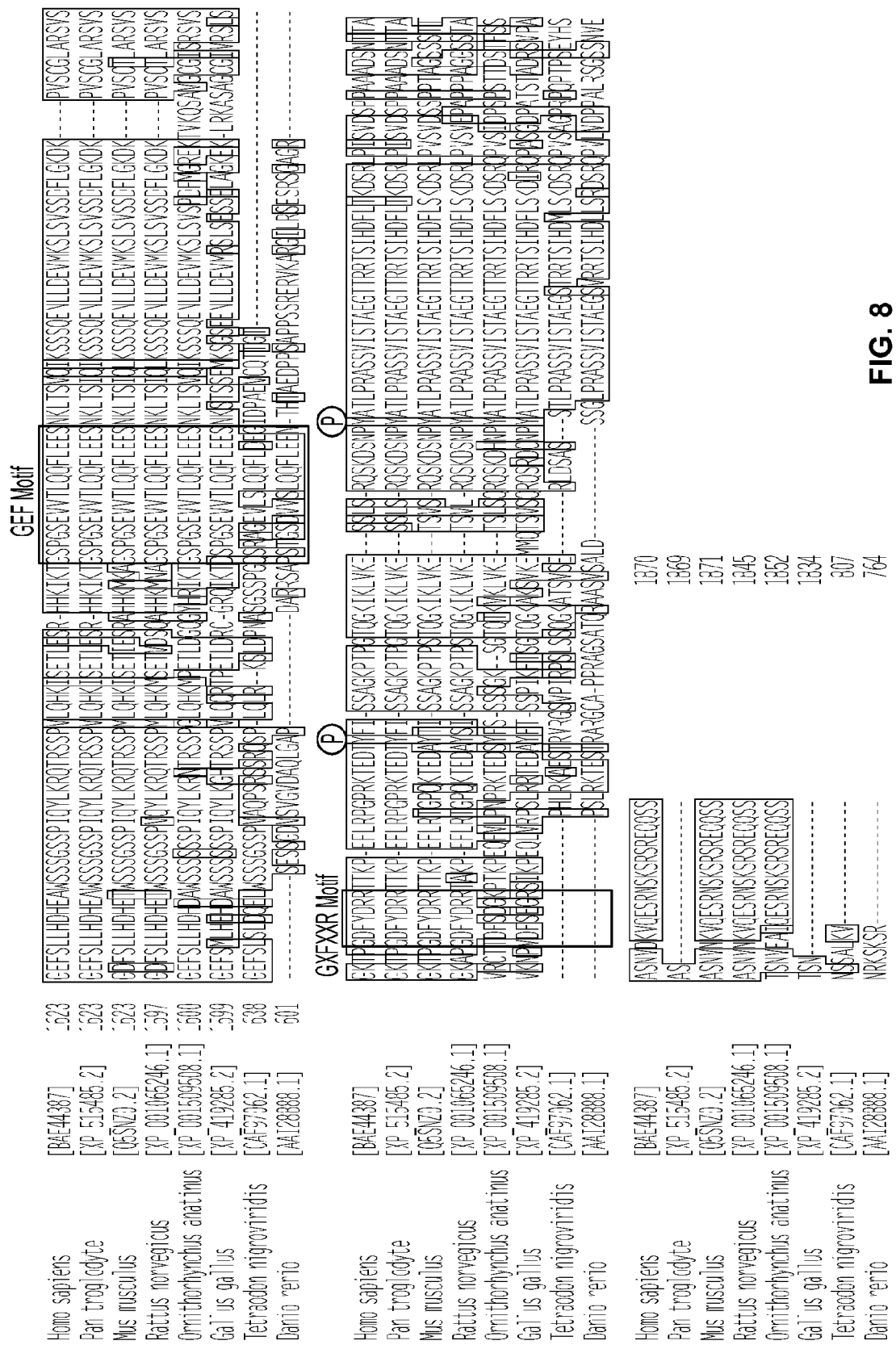
FIG. 8 provides an alignment of amino acid sequences of GIV homologues (SEQ ID NOs:22-29). The alignment demonstrates that the putative SH2-like domain is evolutionarily young, in that it is present only in higher mammals. The sequence corresponding to the C-terminal domain of human GIV (BAE44387, aa1623-1870) was used to identify homologues by BLAST search. The identified homologues with higher identity scores were aligned using CLUSTAL W. Conserved residues are shaded in black; similar residues in gray. The accession number for each species is indicated in brackets. The previously identified, evolutionarily conserved GEF motif is boxed, whereas the recently identified conserved sites of tyrosine phosphorylation are indicated with circles. The core GXFXXR motif (SEQ ID NO:30) within SH2 domain, which is implicated in phosphotyrosine recognition is also boxed. The alignment reveals that unlike the GEF motif, which is conserved in fish, birds and mammals alike, the GXFXXR motif which is a key feature of SH2-like domains, is absent in fish, birds and egg-laying mammals, but highly conserved in higher mammals.
Figure 9A:
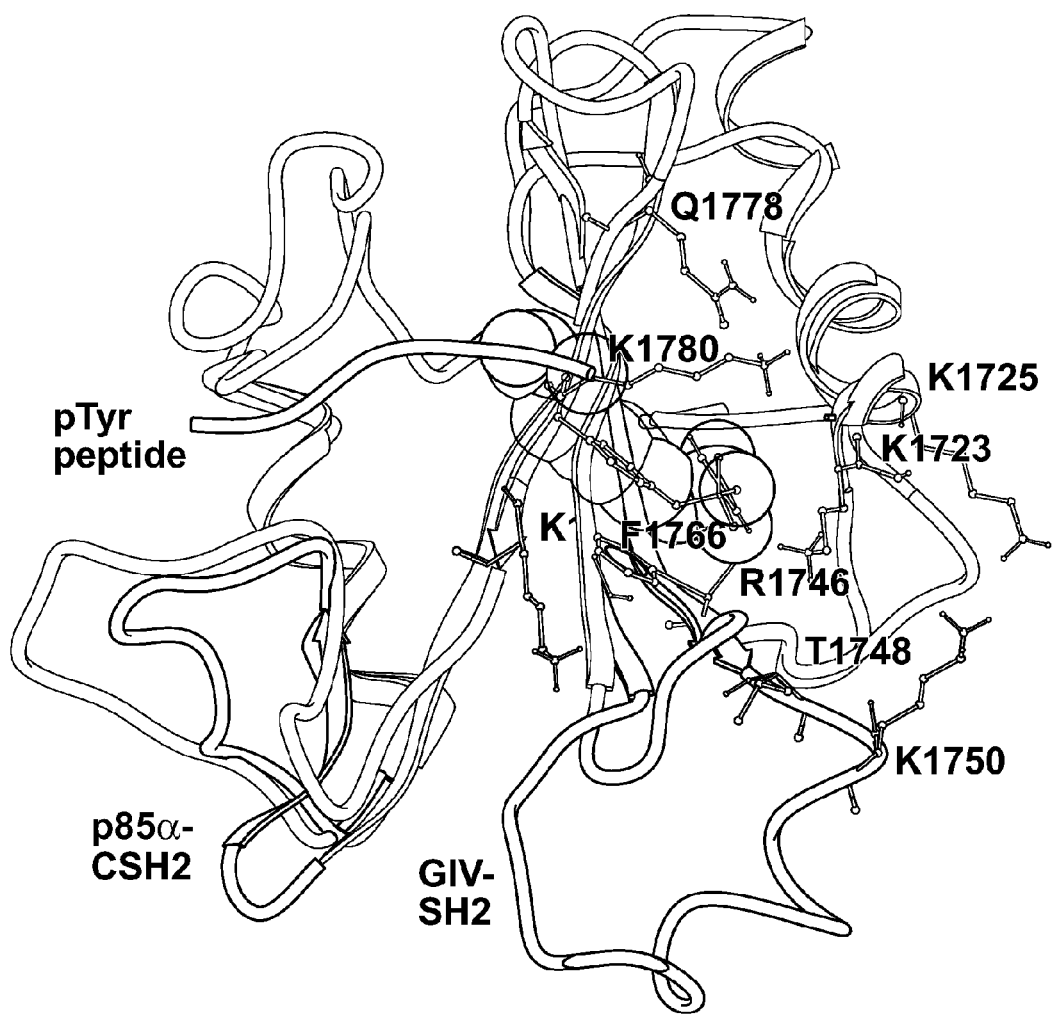
FIG. 9A is a structural model of GIV's C-terminal sequence (aa 1713-1825), which was built based on the alignment with 88 known SH2 templates using ICM software (MolSoft), and superimposed on the established structure (PDB: 1H90) of the C-terminal SH2 domain of p85α (orange) complexed with a phosphopeptide derived from PDGFR. The key residues responsible for engaging the phosphotyrosine ligand are highlighted.
Figure 9B:
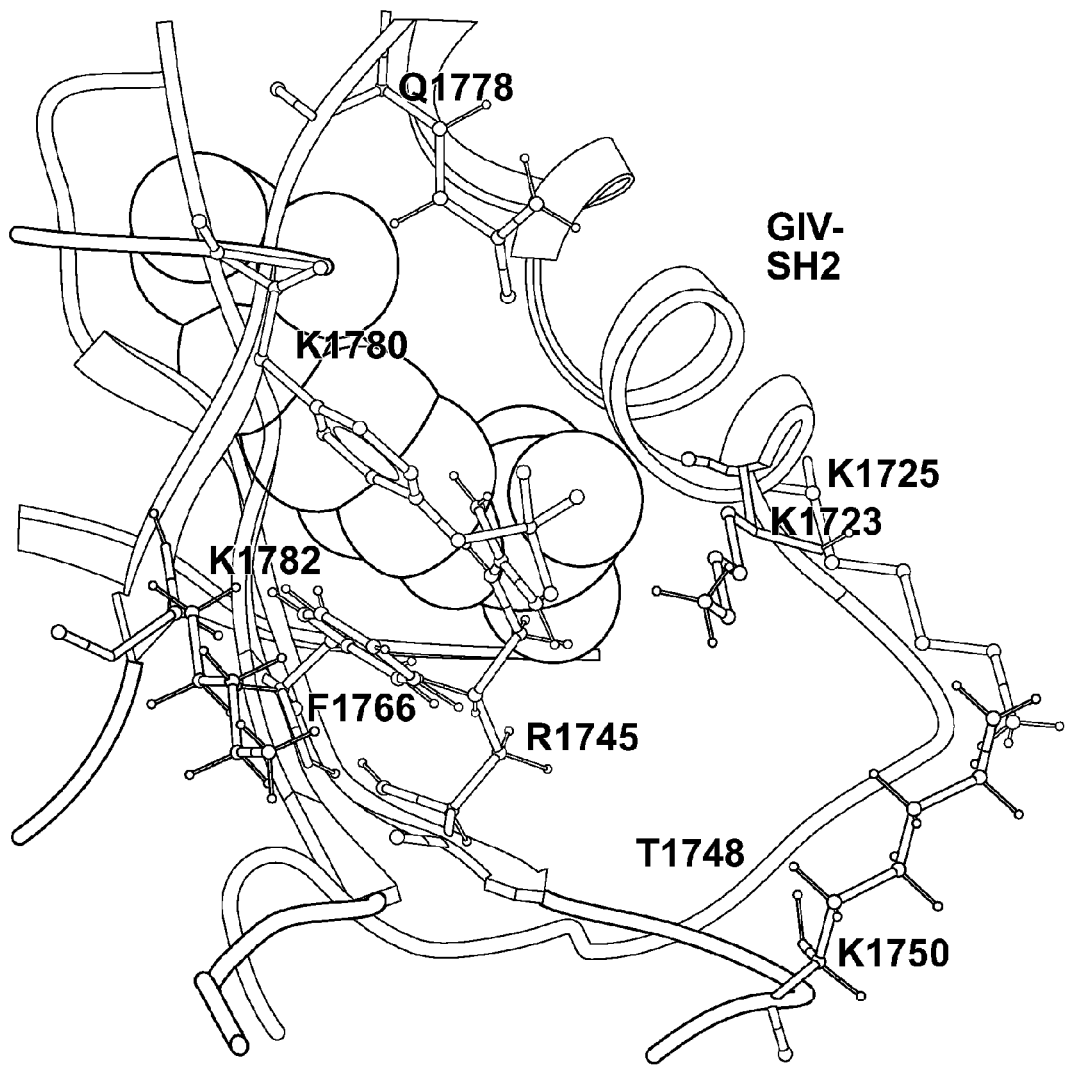
FIG. 9B shows that R1745 of GIV corresponds to the invariant arginine residue in βB5 position within the conserved GXFXXR motif, which is characteristic of the entire SH2 family of adaptors.

Mass spectrometry was performed on in vitro EGFR-phosphorylated His-GIV CT and tyrosines 1764 and 1798 were identified as the sites of phosphorylation within GIV's C-terminus (FIG. 2C). A phylogenetic analysis of GIV revealed that these two tyrosines are conserved in birds and mammals, whereas both are absent in fish or lower animals (FIG. 8). These two tyrosines were previously identified as major phosphosites in vivo (www.phosphosite.org) based on the curated information from several independently-conducted, high-throughput phosphoproteomic studies (Rush et al., Nature Biotechnology, 23:94-101, 2005; Moritz et al., Science Signaling, 3:ra64, 2010; Guo et al., Proc Natl Acad Sci USA, 105:692-697, 2008; Jorgensen et al., Science, 326:1502-1509, 2009; and St-Germain et al., Proc Natl Acad Sci USA, 106:20127-20132, 2008). In addition as summarized in Table 1-1, several kinase prediction programs identified the sequences flanking these tyrosines as suitable substrates for both RTKs and non-RTKs. Specifically, while the sequence flanking Y1764 was predicted to make that site favorable for EGFR, the sequence flanking Y1798 was predicted to make that site favorable for Src.

TABLE 1-1

| GIV Phosphosites* | | |
|---|---|---|
| Phosphosite | Prediction Program | Predicted Kinases |
| Y1764-p | Scansite Motif scan (MIT) | PDGFRbeta, Itk, FGR, EGFR, Abl, InsR, Src |
| Y1764-p | NetPhos (Technical University, Denmark) | Src, EGFR, InsR |
| Y1764-p | KinasePhos (IBSB, NCTU, Taiwan) | InsR, Jak |
| Y1764-p | PhosphoMotif Finder (HPRD) | Alk |
| Y1798-p | Scansite Motif scan (MIT) | Fgr, PDGFRbeta, Lck |
| Y1798-p | NetPhos (Technical University, Denmark) | Src, EGFR, InsR |
| Y1798-p | KinasePhos (IBSB, NCTU, Taiwan) | InsR, Syk, Jak |
| Y1798-p | PhosphoMotif Finder (HPRD) | Src, Jak |

*The sequences of the two phosphosites in human GIV are as follows:
Y1764-p: GPRKTEDT pY FISSAGKP (SEQ ID NO: 2); and
Y1798-P: RQSKDSNP pY ATLPRASS (SEQ ID NO: 3).

Figure 2D:
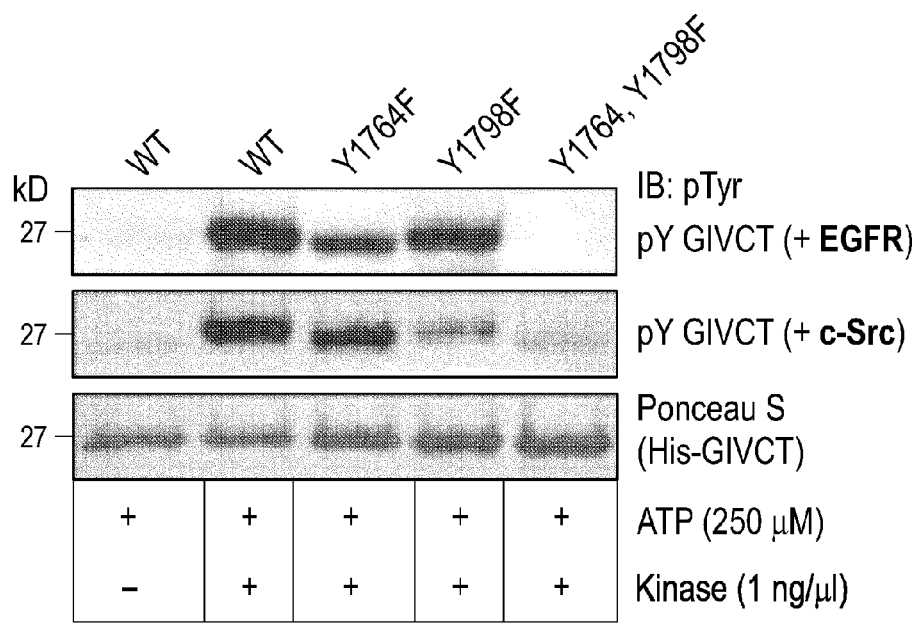
FIG. 2D illustrates the differential GIV phosphorylation by EGF receptor and c-Src. Both EGF receptor and c-Src kinases phosphorylate GIV on Y1764 and Y1798, but EGFR prefers Y1764 whereas c-Src prefers Y1798. In vitro kinase assays were carried out on equal aliquots of wild-type (WT), Y1764F, Y1798F, and Y1764, Y1798F mutants of His-GIV CT (Ponceau S, bottom panel) using recombinant EGFR (top panel) and c-Src (middle panel) kinases and analyzed for tyrosine phosphorylation. GIV WT is phosphorylated by both kinases, whereas the Y1764, Y1798F double mutant is phosphorylated by neither. In the case of Y1764F and Y1798F mutants, EGFR preferentially phosphorylates the Y1798F mutant in which Y1764 is intact and Src phosphorylates the Y1764F mutant in which Y1798 is intact.

By using phosphotyrosine mutants of His-GIV CT, in which each tyrosine was either separately or simultaneously mutated to phenylalanine, both Y1764 and Y1798 were confirmed as substrates for EGFR and Src kinases (FIG. 2D). The His-GIV CT-Y1798F mutant, in which Y1764 is intact, is a better substrate for EGFR kinase, whereas the Y1764F mutant, in which Y1798 is intact, is a better substrate for Src kinase. Both kinases failed to phosphorylate the GIV mutant lacking both tyrosines (His-GIV-CT-Y1764,Y1798F), therefore these two tyrosines account for the observed in vitro phosphorylation of GIV. To discern if these two C-terminal tyrosines also account for the phosphorylation on full length GIV observed in vivo, GIV was immunoprecipitated from starved and EGF-treated Cos7 cells expressing either FLAG-tagged wild-type GIV or a GIV mutant in which both tyrosines are replaced by phenylalanines (henceforth referred to as GIV-WT and GIV-YF, respectively) and tyrosine phosphorylation was determined by immunoblotting. Upon EGF stimulation, GIV-WT, but not GIV-YF underwent tyrosine phosphorylation (FIG. 2E), indicating that tyrosines 1764 and 1798 are indeed the major, and likely the only sites of tyrosine phosphorylation on GIV. Taken together, these results demonstrate that both EGFR and Src can phosphorylate GIV at two C-terminally located tyrosines in vitro, and that these tyrosines are phosphorylated after ligand stimulation in vivo.

Receptor and Non-Receptor TKs Cooperatively Phosphorylate GIV after Stimulation of RTKs and GPCRs.

Figure 11:
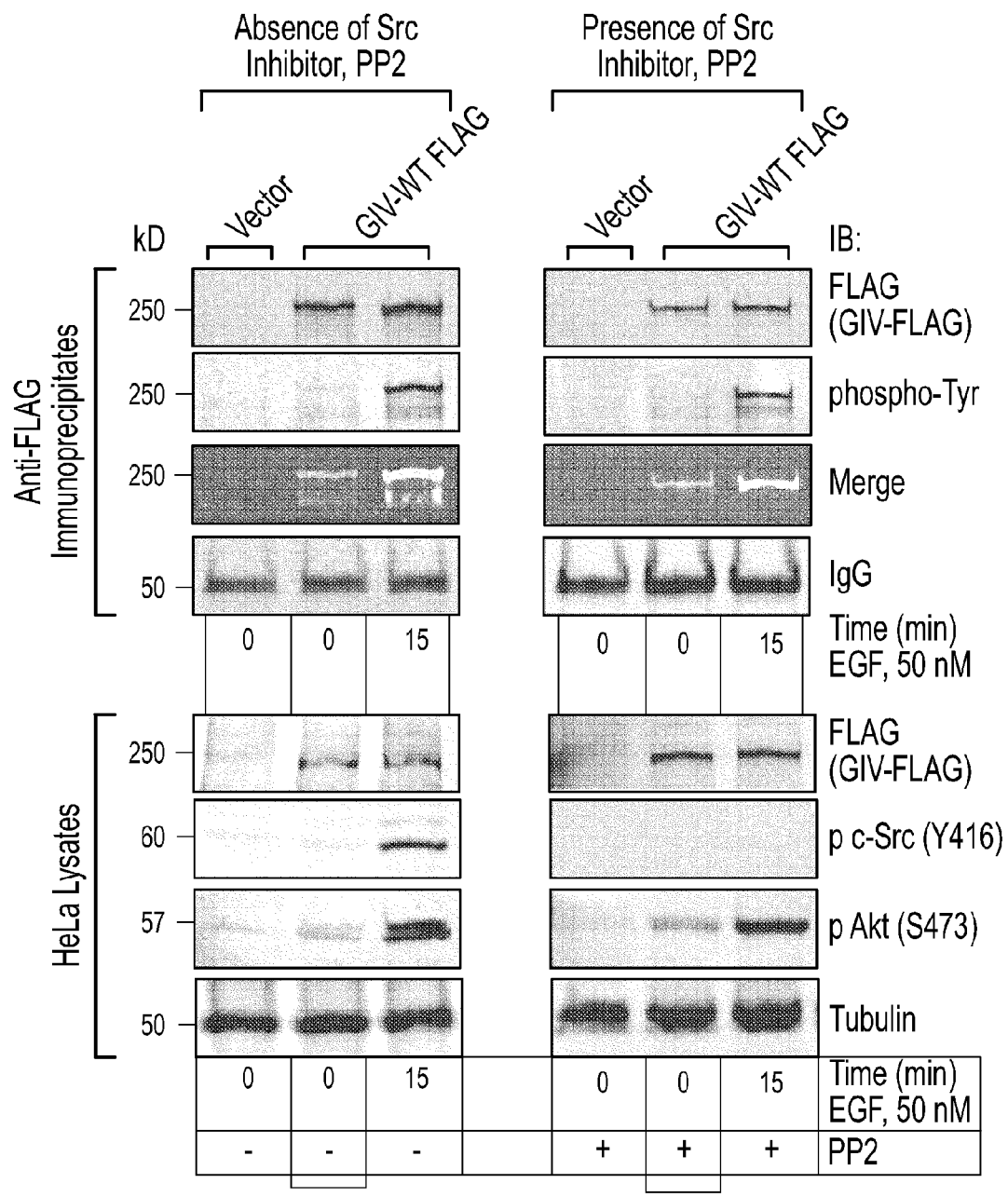
FIG. 11 shows that both EGFR and Src kinases can phosphorylate GIV after EGF stimulation. HeLa cells transiently transfected with FLAG-tagged wild-type (GIV-WT-FLAG) or vector control were starved for 16 h and then incubated for 1 h in the presence or absence of 250 nM PP2 (a specific inhibitor for Src-family of kinases). Cells were subsequently stimulated with 50 nM EGF for 15 min prior to lysis. Equal aliquots of lysates (bottom panels) were subjected to SDS PAGE and immunoblotted to confirm effective inhibition of Src kinase, as determined by suppressed levels Src phosphorylation at Y416 in the presence of PP2. Equal aliquots of these lysates were incubated with anti-FLAG mAb and the immune complexes (top panels) were subjected to two-color immunoblotting (IB) for GIV and pTyr using the LI-COR Odyssey Infrared Western Blot Imaging System. Single colored image for GIV-FLAG (topmost panel) is displayed in grayscale which shows that GIV is immunoprecipitated only from GIV-FLAG transfected cells, but not in vector controls. pTyr panel shows that tyrosine phosphorylation was incurred exclusively upon ligand stimulation. Yellow pixels of the overlaid GIV-FLAG (Red) and pTyr (Green) images (Merge panel) confirm that in the absence of PP2, when EGFR and Src kinases are active, GIV-WT is phosphorylated on tyrosines. Similarly, in the presence of PP2, despite Src inhibition, GIV-WT is phosphorylated on tyrosines after EGF treatment. This indicates that tyrosine phosphorylation of GIV-WT after EGF stimulation could be interchangeably or cooperatively mediated by both EGFR and Src kinases in vivo.

EGF stimulation results in activation of both EGFR and Src kinases (Osherov and Levitzki, Eur. J. Biochem. 225: 1047-53, 1994). Whether ligand-dependent tyrosine phosphorylation of GIV is mediated by both receptor and non-receptor kinases was assessed. To investigate this, PP2, a selective inhibitor for Src family kinases (Hanke et al., J. Biol. Chem, 271:695-01, 1996) was used in in vivo phosphorylation assays. Upon EGF stimulation GIV-WT is phosphorylated in the presence and absence of PP2 (FIG. 11), indicating that GIV is tyrosine phosphorylated despite inhibition of Sric-family of kinases, likely by EGFR kinase. Ligand-stimulation of GPCRs is known to activate Src kinase (Andreev et al., J. Biol. Chem., 276:20130-35, 2001). Therefore, whether activation of lysophosphatidic acid (LPA) receptors (a prototype member of the GPCR family) also triggers tyrosine phosphorylation of GIV was assessed. Indeed, LPA stimulation resulted in the phosphorylation of GIV-WT, but not GIV-YF (FIG. 2F), showing that Y1764 and Y1798 account for the observed tyrosine phosphorylation of GIV after LPA treatment. Phosphorylation of GIV-WT was virtually abolished when cells were incubated with the Src inhibitor PP2 prior to LPA stimulation, demonstrating that ligand-stimulation of LPAR triggers tyrosine phosphorylation of GIV via Src family kinases. Collectively, these results demonstrate that both EGF and LPA trigger tyrosine phosphorylation of GIV. EGF triggers phosphorylation via EGFR, whereas LPA primarily utilizes non-receptor TKs, like the Src-family of kinases, to phosphorylate GIV. Thus, both receptor and non-receptor Src-like kinases interchangeably or cooperatively phosphorylate GIV in vivo after ligand stimulation.

Tyrosine Phosphorylation of GIV is Required for Enhancement of Akt Phosphorylation, Actin Remodeling and for Cell Migration.

Figure 3A:
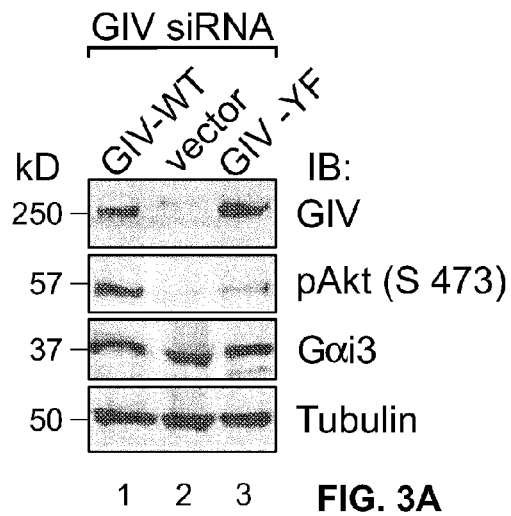
FIG. 3A shows that HeLa-GIV-WT, but not Hela-GIV-YF cells enhance Akt phosphorylation. HeLa cells stably expressing control vector, siRNA resistant GIV-WT or GIV-YF plasmids were treated with GIV siRNA. 36 h post-transfection, cells were split and re-seeded in 10% FBS for 12 h prior to lysis. Equal aliquots of whole-cell lysates were analyzed for GIV, phospho-Akt (pAkt), Gαi3, and tubulin by immunoblotting (IB). Phosphorylation of Akt (pAkt) is significantly reduced in GIV-depleted control cells (lane 2) and GIV-YF cells (lane 3) compared to GIV-WT cells (lane 1). $p<0.01$ for both comparisons; N=3.
Figure 3B:
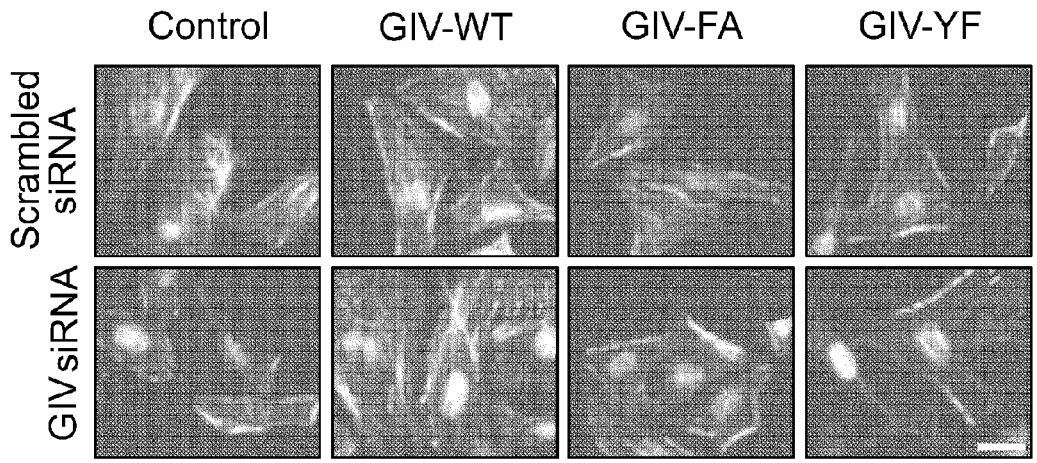
FIG. 3B shows that HeLa-GIV-YF cells show absence of actin stress fibers compared to HeLa-GIV WT cells. HeLa cells stably expressing vector (control), siRNA resistant GIV-WT, GIV-FA (the GEF-deficient mutant), or GIV-YF plasmids were treated with scrambled or GIV siRNA as indicated. Cells were co-stained with phalliodin-Texas red (F-actin, red) and DAPI (DNA, blue) and visualized by fluorescence. Depletion of GIV in control cells resulted in loss of stress fibers (compare a and b). Expression of siRNA resistant GIV-WT (d) restored formation of actin stress fibers, whereas GIV-FA (f) or GIV-YF (h) did not. Both GIV-FA and GIV-YF cells show a paucity of stress fibers even without depletion of endogenous GIV (e and g), indicating that these GIV mutants have a dominant negative effect on actin remodeling. Bar=10 μM.
Figure 3C:
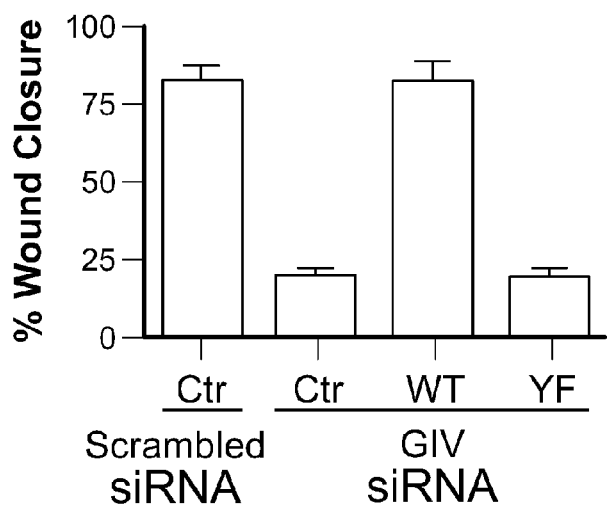
FIG. 3C shows that HeLa-GIV-WT, but not HeLa-GIV-YF cells migrate efficiently in scratch-wound assays. Untransfected HeLa cells (Ctr, control), HeLa-GIV-WT, HeLa-GIV-FA, and HeLa-GIV-YF cells were treated with scrambled or GIV siRNA as in 2A. Cell migration was determined as described in Methods. Depletion of GIV from control (Ctr) cells inhibits migration, which is reversed in GIV-WT cells, but not in GIV-YF cells. Results are shown as mean±S.D. of 8-12 randomly chosen fields from 3 independent experiments. $p<0.0001$ for comparisons between Ctr and GIV-depleted cells, and between GIV-WT and GIV-YF cells.
Figure 3D:
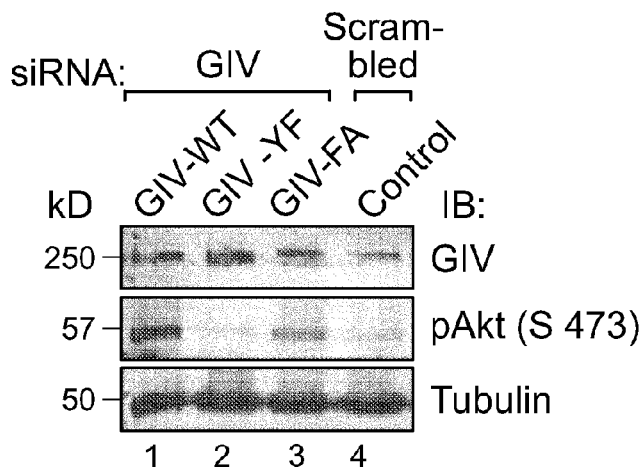
FIG. 3D shows a comparison of Akt phosphorylation between HeLa-GIV-WT, Hela-GIV-FA, and HeLa-GIV-YF cells. Control HeLa cells and HeLa cells stably expressing siRNA resistant GIV-WT, GIV-YF, and GIV-FA plasmids were treated with scrambled and GIV siRNA and analyzed for GIV, phospho-Akt (pAkt), and tubulin by immunoblotting (IB). Extent of Akt phosphorylation (pAkt) is highest in GIV-WT (lane 1), lowest in GIV-YF and control cells (lanes 2, 4), and intermediate in GIV-FA (lane 3). p-values for paired comparisons between GIV-WT and GIV-FA is <0.01, and for GIV-WT and GIV-YF is <0.001; N=3.

To investigate whether tyrosine phosphorylation is required for GIV's functions (i.e., Akt enhancement, actin remodeling and cell migration, see e.g., Enomoto et al., Annals NY Acad Sci, 1086:169-184, 2006), HeLa cell lines were created that stably express the siRNA-resistant, FLAG-tagged GIV wild-type (HeLa-GIV-WT) or mutant GIV Y1764,Y1798F (HeLa-GIV-YF) at abundance ~1.5-2 fold above endogenous GIV. Endogenous GIV was depleted in both cell lines and in control HeLa cells using previously validated siRNA oligonucleotides (Garcia-Marcos et al., Proc. Natl. Acad. Sci. USA 106:3178-83, 2009). Analysis of these cells revealed that phosphorylation of Akt in HeLa-GIV-YF and in GIV-depleted controls was severely reduced compared to that in HeLa-GIV-WT cells (FIG. 3A). Formation of actin stress fibers was impaired in HeLa-GIV-YF cells but present in GIV-WT cells (FIG. 3B). In addition, HeLa-GIV-YF cells did not migrate as efficiently as HeLa-GIV-WT cells in scratch-wound assays (FIG. 3C). Next, HeLa-GIV-YF cells were compared with HeLa cells expressing FLAG-tagged, GEF-deficient GIV-F1685A mutant (HeLa-GIV-FA), which is incapable of interacting with or activating Gαi (Garcia-Marcos et al., supra, 2009). In the absence of a functional GEF motif, GIV-FA cells fail to remodel actin, or enhance Akt phosphorylation, or migrate after scratch-wounding compared to GIV-WT cells (Cantley, Science, 296:1655-57, 2002). The side-by-side comparison of Akt phosphorylation in GIV-FA and GIV-YF cells demonstrated that the loss of phosphotyrosines in GIV-YF cells had a greater impact on Akt phosphorylation (FIG. 3D) than the loss of the GEF motif in GIV-FA cells. Regardless, both HeLa-GIV-YF and HeLa-GIV-FA cells failed to rescue GIV's functions when endogenous GIV was depleted (FIG. 3A-D), indicating that both tyrosine phosphorylation of GIV and its GEF function are required for regulating Akt signaling and actin remodeling during cell migration.

GIV's Phosphotyrosines Function Independently of its GEF Motif.

Figure 3E:
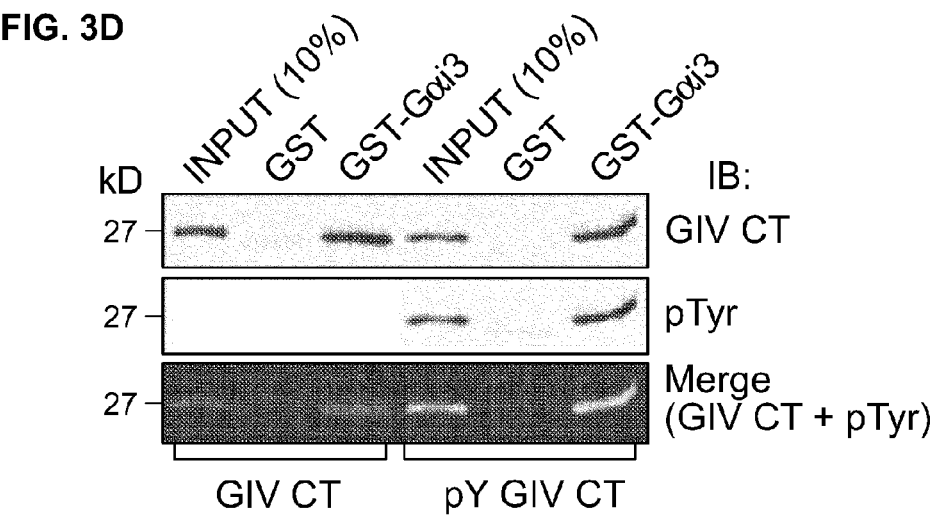
FIG. 3E-F shows that phosphorylation of His-GIV-CT by EGFR kinase does not alter its ability to bind and activate Gαi3.
Figure 3F:
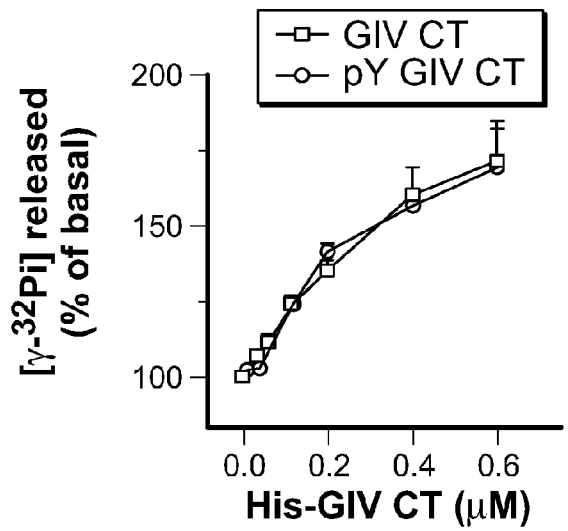

To investigate whether tyrosine phosphorylation affects GIV's ability to bind and activate Gαi3, mock-treated and in vitro phosphorylated His-GIV CT were prepared and both proteins were affinity purified on cobalt beads. Both mock-treated and phosphorylated GIV-CT bound Gαi3 equally in pulldown assays (FIG. 3E). A comparison was conducted with respect to the ability of sham-treated and phosphorylated His-GIV CT to activate Gαi3. The measurement of steady-state GTPase activity of the G protein demonstrated that both proteins increased the GTPase activity of His-Gαi3 in a dose-dependent manner and with equal potency (FIG. 3F). Regardless of its phosphorylation status both His-GIV CT proteins increased the GTPase activity of Gαi3 by ~1.7-fold over the basal activity at 0.6 μM, the maximal concentration tested. These results demonstrate that tyrosine phosphorylation of GIV has no effect on the Gαi3-GIV interaction and on GIV's GEF activity towards Gαi3.

Figure 12A:
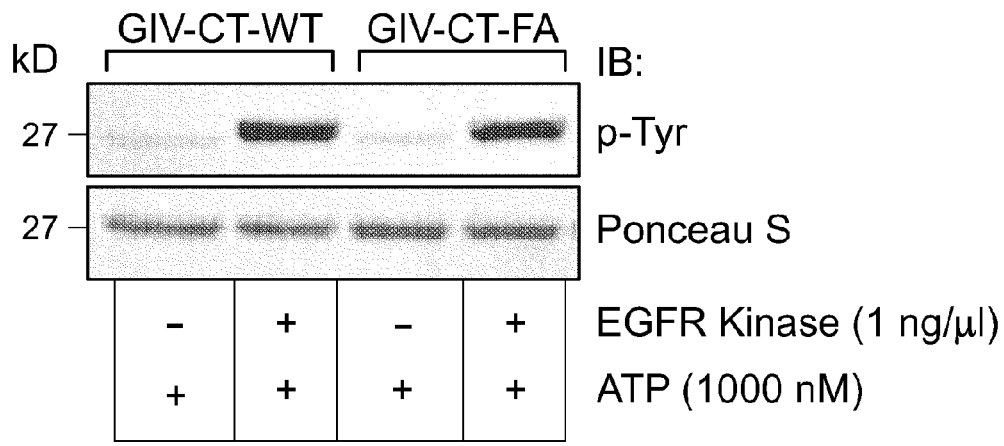
FIG. 12A shows that wild-type (GIV CT-WT) and a GEF-deficient F1685A (GIV CT-FA) GIV mutant are equally phosphorylated in vitro by recombinant EGFR kinase. Equal aliquots (~5 µg) of His-tagged GIV CT-WT and GIV CT-FA were subjected to in vitro kinase assays in the presence or absence of ATP and recombinant receptor tyrosine kinases. Entire reactions were subjected to SDS PAGE and analyzed for the extent of tyrosine phosphorylation using anti-phosphotyrosine (pTyr) mAb by immunoblotting (IB).
Figure 12B:
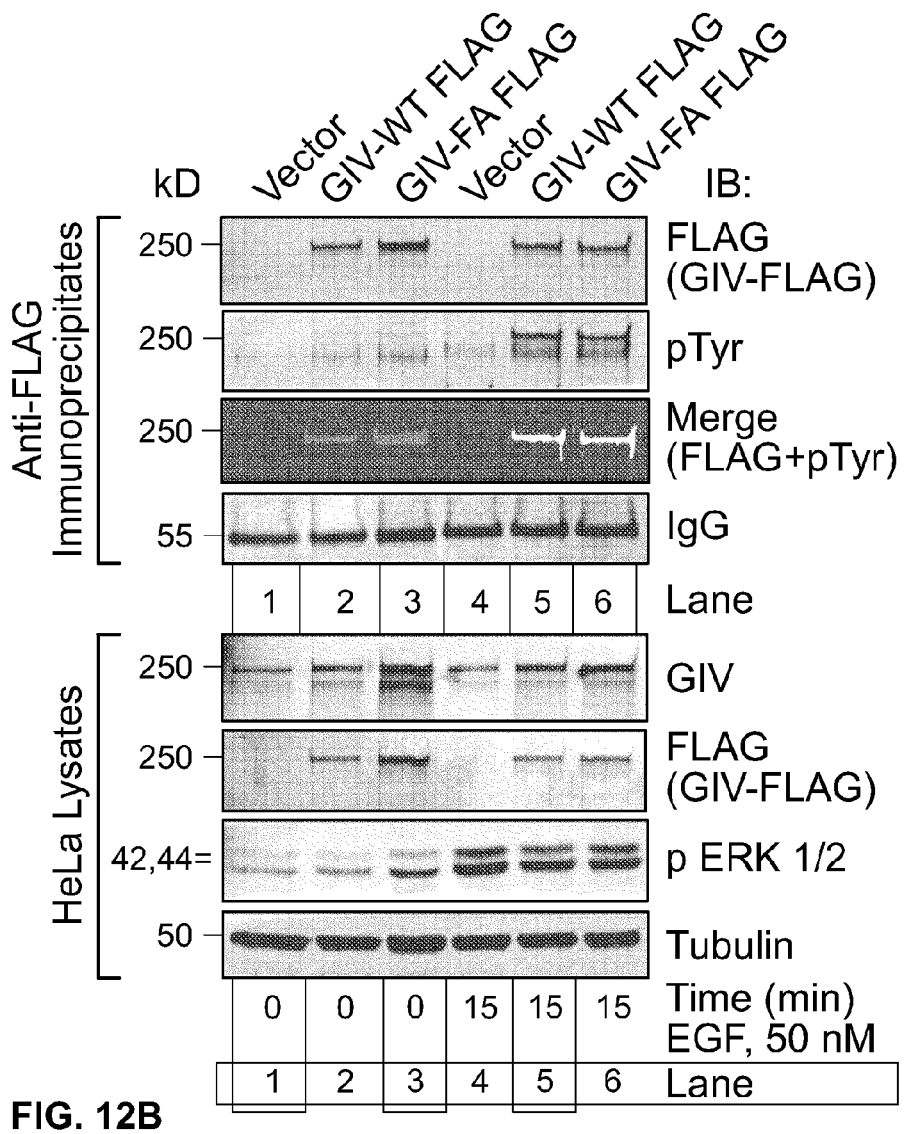
FIG. 12B shows that GIV-FA is efficiently tyrosine phosphorylated in vivo after EGF-stimulation. HeLa cells transiently transfected with FLAG-tagged wild-type (GIV-WT-FLAG), or GIV-FA-FLAG, or vector control were starved and stimulated with 50 nM EGF for 15 min prior to lysis. Equal aliquots of lysates (bottom panels) were incubated with anti-FLAG mAb Immunoprecipitated complexes (top panels) were subjected to two-color immunoblotting (IB) for GIV and pTyr using the LI-COR Odyssey Infrared Western Blot Imaging System. Single colored image for GIV-FLAG (top panel) is displayed in grayscale which shows that GIV is immunoprecipitated from GIV-FLAG transfected cells (lanes 2, 3, 5, 6), but not from vector transfected controls (lanes 1, 4). pTyr panel shows that tyrosine phosphorylation was incurred robustly after EGF stimulation (lanes 5, 6). Yellow pixels of the overlaid GIV (red) and pTyr (green) images (Merge panel) confirm that both GIV-WT (lane 5) and GIV-FA mutant (lane 6) are phosphorylated on tyrosine(s) after EGF treatment, indicating that the GEF domain is not required for tyrosine phosphorylation of GIV. The ~180 kD band detected by anti-pTyr antibody (in lanes 5, 6) was determined to be the GIV-associated pool of ligand-activated EGF receptor.

To determine whether GIV's GEF function is required for tyrosine phosphorylation of GIV, an in vitro kinase assays was conducted on His-GIV-CT-WT and His-GIV-CT FA (F1685A) proteins using recombinant EGFR kinase. In this assay, GIV-CT FA was phosphorylated as efficiently as GIV-CT WT (FIG. 12A) Immunoprecipitation of FLAG-tagged GIV-WT and GIV-FA from EGF-treated HeLa cells revealed that both proteins were equally phosphorylated (FIG. 12B), indicating that the GEF function was also not required for tyrosine phosphorylation of GIV in vivo. Collectively, these results demonstrate that tyrosine phosphorylation and GIV's GEF motif function independently of each other during cell migration.

Tyrosine Phosphorylated GIV Binds SH2 Domains of the p85α-Regulatory Subunit of PI3K.

Figure 4A:
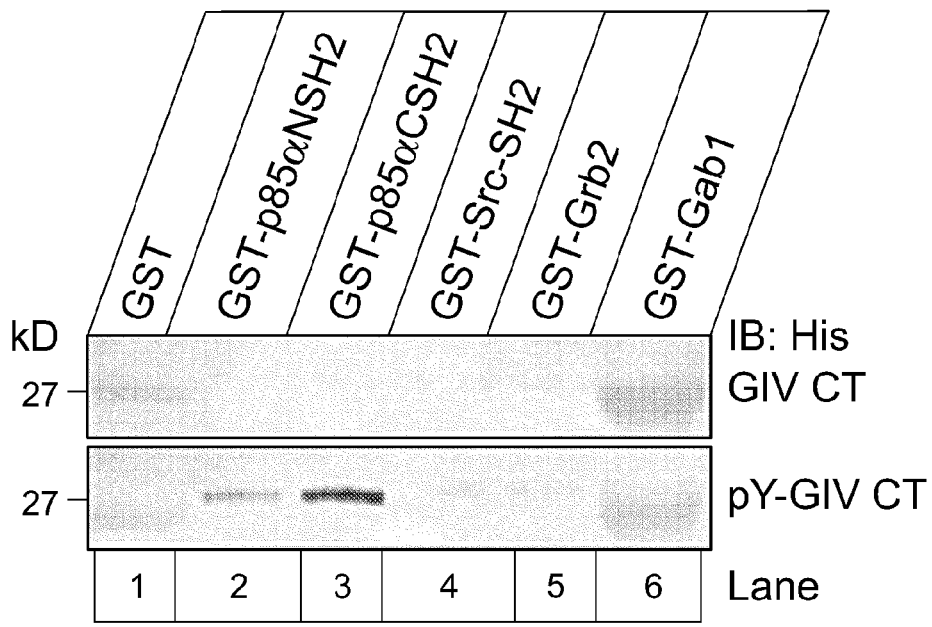
FIG. 4A shows that phosphorylated GIV-CT directly and specifically binds to the C-terminal SH2 domain of p85α (p85α-CSH2). Mock-treated GIV-CT and in vitro EGFR-phosphorylated pY GIV-CT were incubated with ~35 μg of the indicated GST-SH2 adaptors or GST immobilized on glutathione beads. Bound His-GIV-CT was analyzed by immunoblotting (IB) with anti-His mAb. pY GIV-CT, but not GIV-CT specifically bound the C-terminal SH2 domain of p85α (lane 3), and weakly to the N-terminal SH2 domain of p85α (lane 2).
Figure 4B:
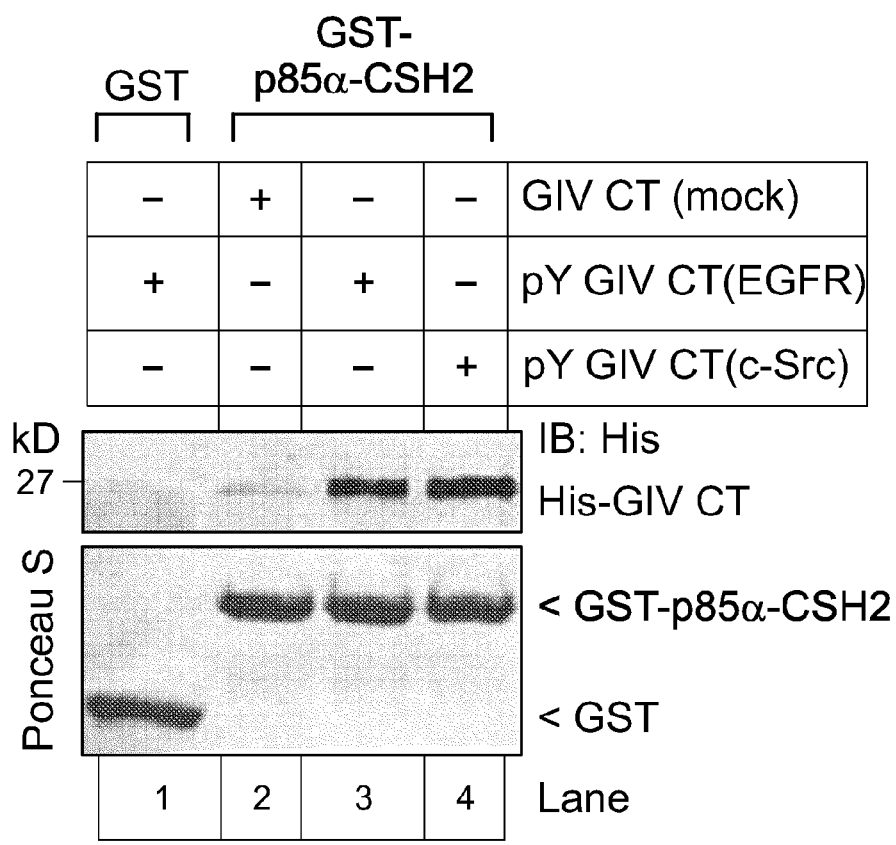
FIG. 4B shows that both EGFR and Src-phosphorylated GIVCT (pY GIV-CT) bind p85α-CSH2. Mock-treated GIV-CT and in vitro EGFR or Src-phosphorylated (pY GIV-CT) His-GIV-CT were incubated with ~35 μg of GST-p85α-CSH2 adaptor or GST immobilized on glutathione beads. Bound His-GIV CT was analyzed by immunoblotting (IB) with anti-His mAb. GIV CT bound p85α-CSH2 exclusively after phosphorylation by EGFR and Src-kinases (lanes 3, 4), but not when sham-treated (lane 2).
Figure 4C:
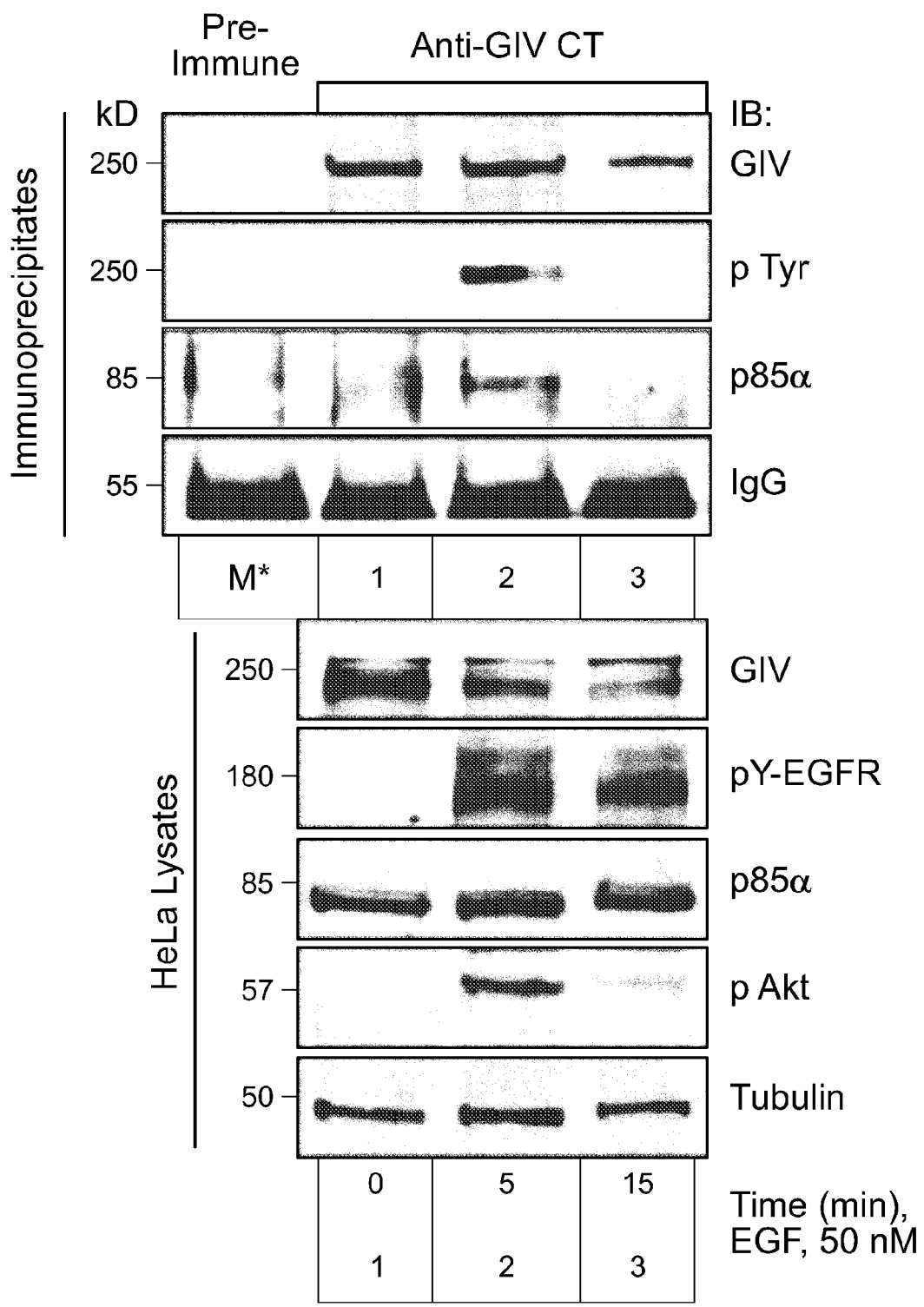
FIG. 4C shows that tyrosine phosphorylation of endogenous GIV peaks at 5 min after EGF stimulation, and temporally coincides with its interaction with p85α(PI3K) and enhancement of Akt phosphorylation. HeLa cells were starved (0 min), and subsequently stimulated with EGF for indicated time periods prior to lysis. Equal aliquots of lysates (bottom) were incubated with anti-GIV (CT Ab; lanes 1-3) or a mix (M) of them was incubated with pre-immune IgG Immune complexes (top) were analyzed for the presence of endogenous GIV, phosphotyrosine (pTyr) and p85α by immunoblotting (IB). GIV is tyrosine phosphorylated and is maximally associated with p85α at 5 min after EGF stimulation (lane 2; top), which coincides with peak phosphorylation of Akt (pAkt, lane 2; bottom).
Figures 4D, 4E:
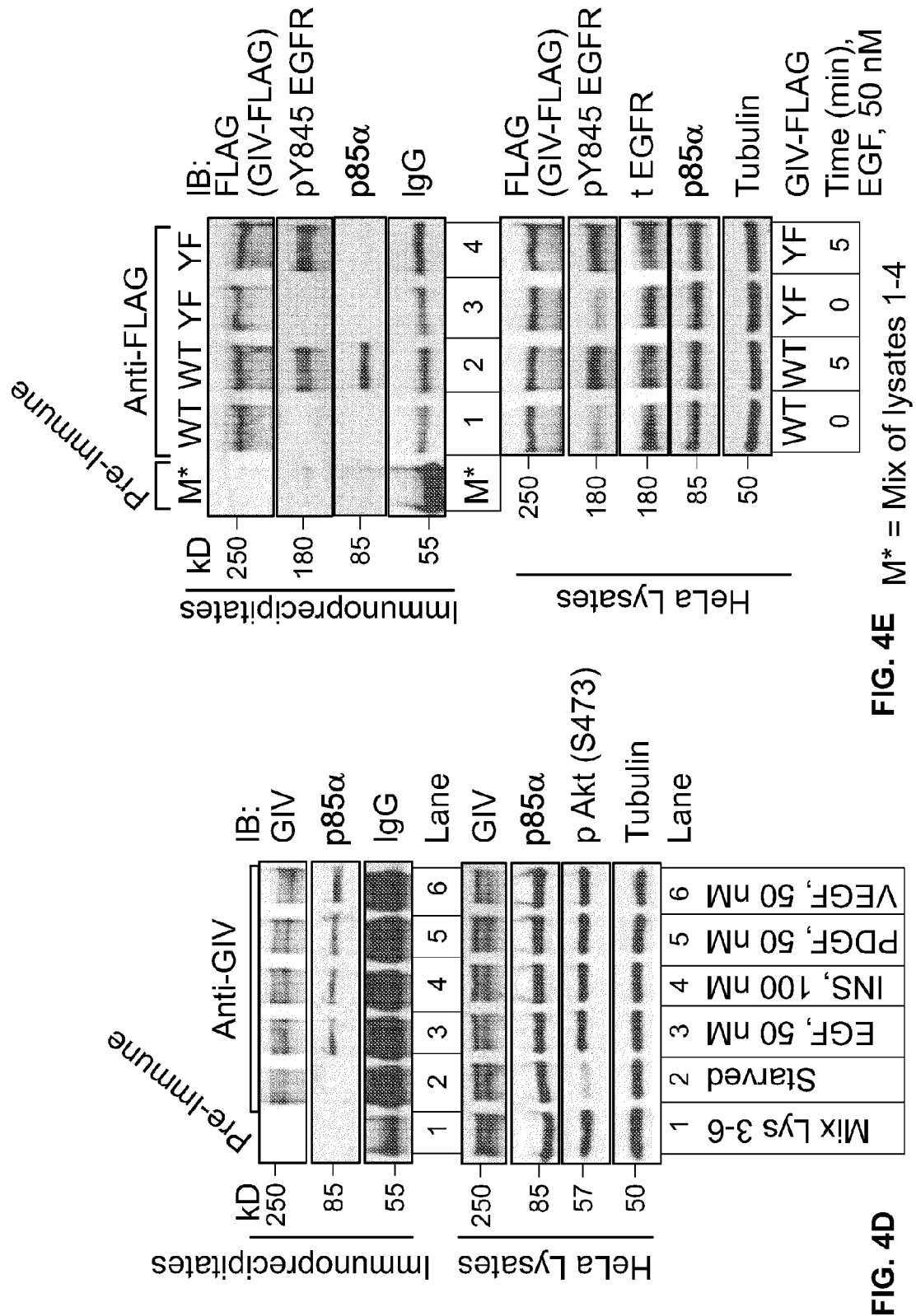
FIG. 4D shows that endogenous GIV and p85α co-immunoprecipitate upon stimulation with a variety of growth factors. HeLa cells were serum starved (0.2% FBS, 16 h) and then treated with the indicated growth factors prior to lysis. Equal aliquots of lysates (bottom) were treated with anti-GIVCT Ab or preimmune IgG Immunoprecipitated complexes (top) were analyzed for GIV and p85α by immunoblotting (IB). GIV coimmunoprecipitates with p85α exclusively after growth factor stimulation (compare lane 2 with lanes 3-5), and multiple growth factors can trigger such association.
FIG. 4E shows that GIV-WT, but not GIV-YF co-immunoprecipitates with p85α upon EGF stimulation, whereas both can bind ligand-activated EGFR. Cos7 cells transfected with either FLAG tagged-wild-type (WT, lanes 1 and 2) or phosphotyrosine Y1764,Y1798F mutant (YF, lane 3) were starved, and subsequently stimulated with EGF prior to lysis. Equal aliquots of lysates (bottom) were incubated with anti-FLAG mAb or pre-immune IgG. Immune complexes (top) were analyzed for the presence of GIV-FLAG, ligand-activated EGFR (pY845 EGFR) and p85α by immunoblotting (IB). Phospho-EGFR coimmunoprecipitates with both GIV-WT (lane 2) and GIV-YF (lane 4) exclusively after EGF stimulation, whereas p85α coimmunoprecipitates with GIV-WT (lane 2), but not GIV-YF (lane 3).
Figure 13A:
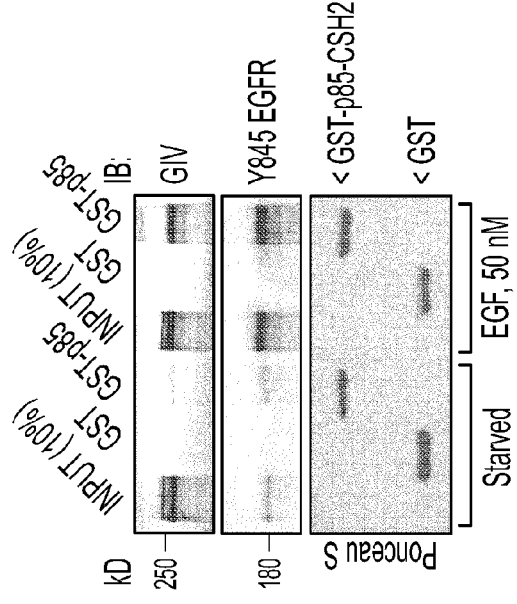
FIG. 13A shows that endogenous GIV binds GST-C-SH2 p85α exclusively upon EGF stimulation. Equal aliquots (15 µg) of GST or GST-p85α-CSH2 were used in pull-down assays with lysates of Cos7 cells which were starved in 0.2% FBS for 16 h and then stimulated with 50 nM EGF. Bound proteins were visualized by immunoblotting (IB) for GIV and ligand-activated EGFR (pY845 EGFR). Both GIV and EGFR bind GST-p85α-CSH2 exclusively after EGF stimulation.
Figure 13B:
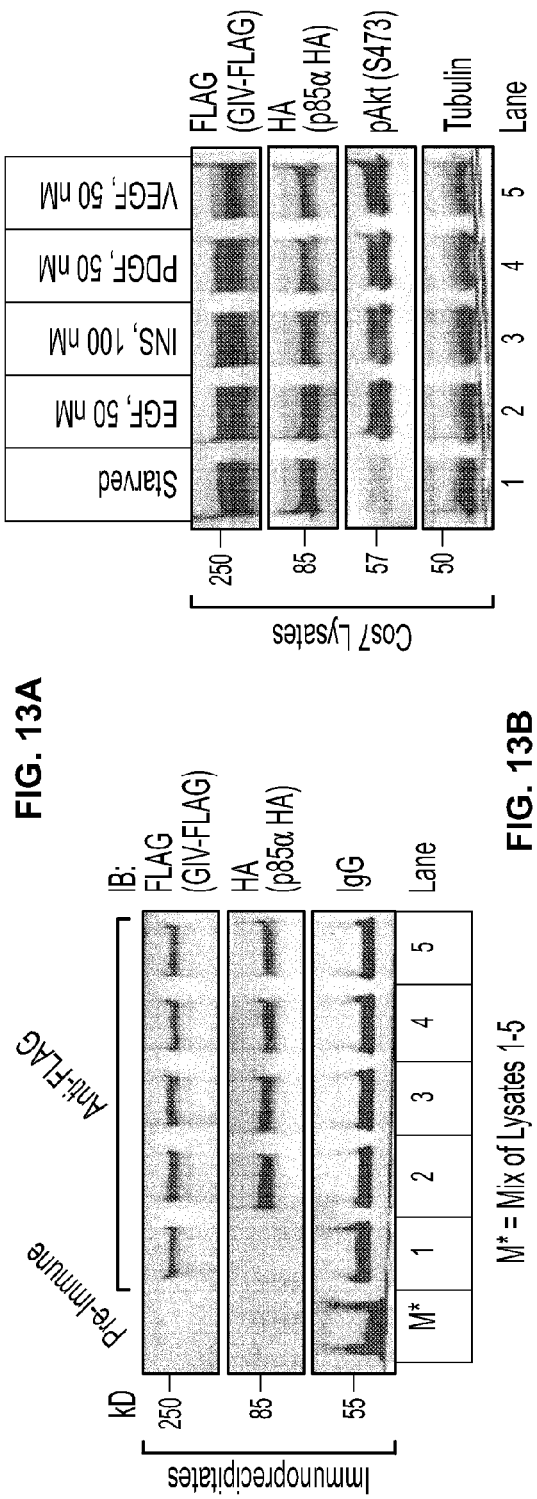
FIG. 13B shows that exogenously expressed GIV-FLAG and p85α-HA co-immunoprecipitate upon growth factor stimulation. Cos7 cells transiently co-transfected with GIV-FLAG and p85α-HA were serum starved and then treated with the indicated growth factors prior to lysis. Equal aliquots of lysates (right) were treated with anti-FLAG mAb or preimmune IgG Immunoprecipitated complexes (left) were analyzed for GIV (GIV-FLAG) and p85α (p85α-HA) by immunoblotting (IB). GIV coimmunoprecipitates with p85α exclusively after growth factor stimulation (compare lane 1 with lanes 2-5), and multiple growth factors can trigger such association. M=mix of lysates 1-5.
Figure 13C:
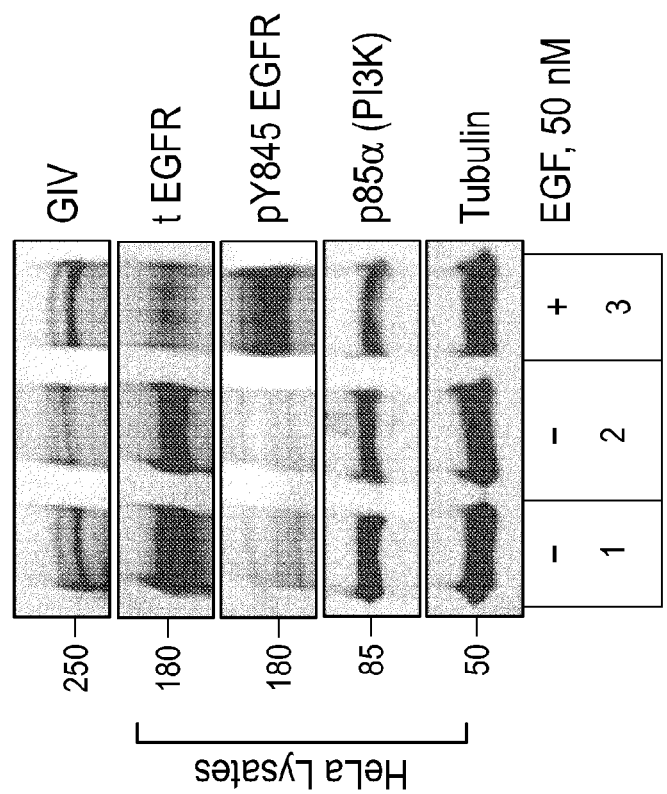
FIG. 13C shows that endogenous GIV, p85α(PI3K) and EGFR form a ternary complex in HeLa epithelial cells after ligand stimulation. HeLa cells were serum starved (−) and then treated with 50 nM EGF (+) prior to lysis. Equal aliquots of lysates (right) were treated with anti-GIV-CT rabbit pcAb or preimmune control IgG. Lysates and immunoprecipitated complexes (left) were analyzed for GIV, total (t EGFR), ligand-activated EGFR (pY845 EGFR), and p85α (PI3K) by immunoblotting (IB). GIV coimmunoprecipitates with ligand-activated EGFR and p85α exclusively after EGF stimulation (compare lanes 2 and 3).
Figure 13C:
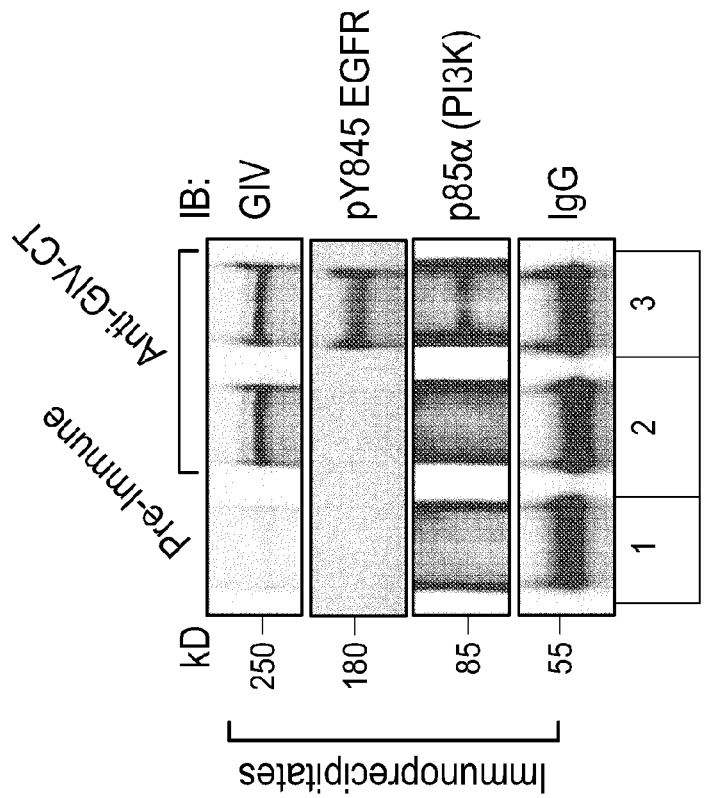
Figure 14A:
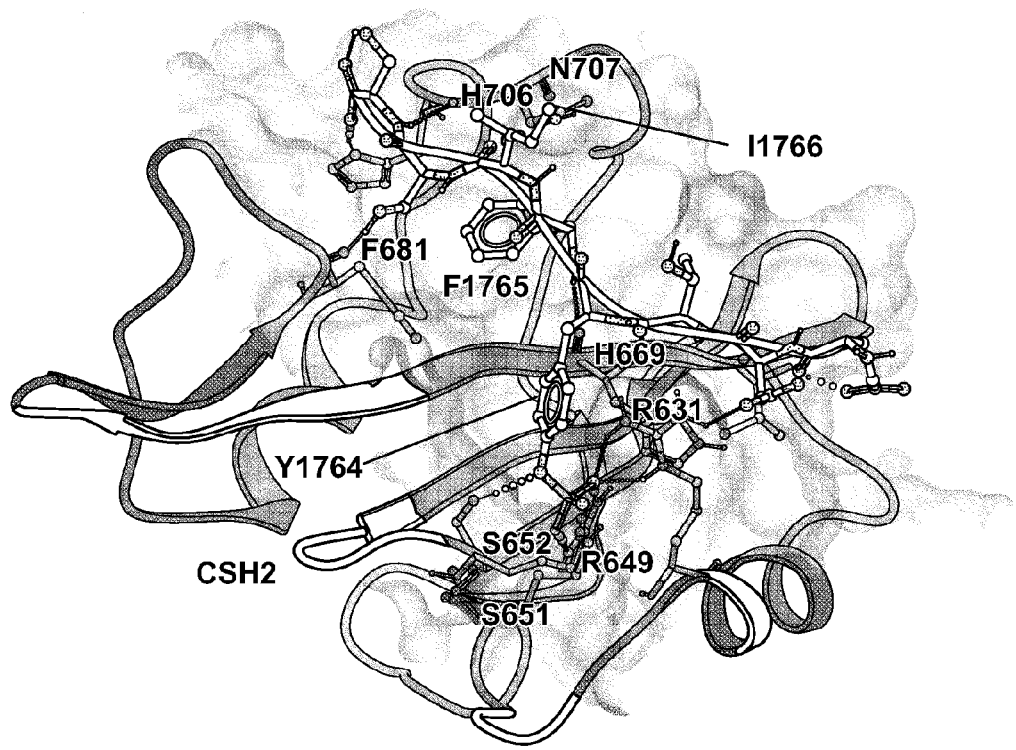
FIG. 14A shows the proposed structure of a complex between p85α-CSH2 and the GIV-derived phosphopeptide pY1764FISS (SEQ ID NO:5). The electrostatic potential of the phosphotyrosine-binding surface of p85α is colored according to solvation properties of the residues in the original figure (white, hydrophobic; green, polar; blue, basic; red, acidic). In this conformation 12 favorable hydrogen-bonding interactions are seen in this conformation, without any steric clashes. S1767 hydrogen-bonds with the backbone oxygen of F681 on p85α-CSH2, S1768 does not hydrogen-bond, F1765 occupies a shallow hydrophobic pocket, I1766 orients outwards, and the backbone hydrogen bonding is strong. In the predicted binding mode, R631, R649, S651, and S652 of p85α-CSH2 make hydrogen bonds with the pY1764 of GIV in the manner similar to the established crystal structure of p85α-CSH2 bound to pY751 of PDGFRβ. In addition, the backbone atoms of H669, F681, and H706 and side chains of H706 and N707 make multiple hydrogen bonds with the backbone and side-chain atoms of GIV's pY1764FISS peptide.
Figure 14B:
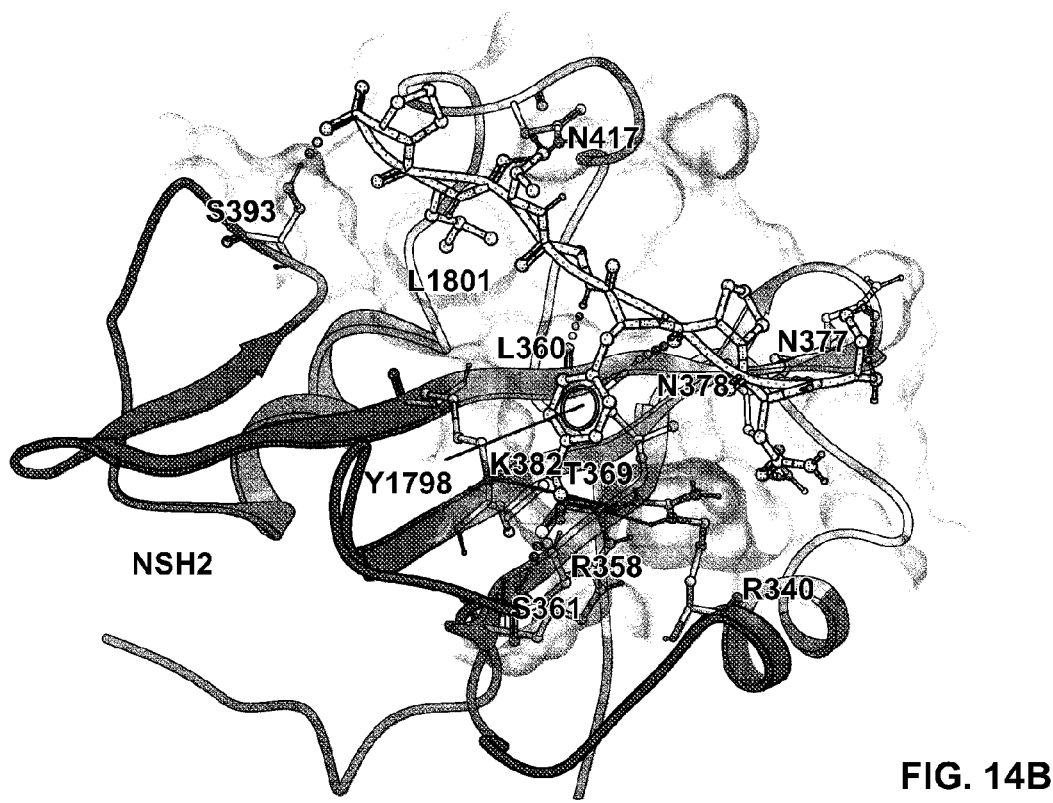
FIG. 14B shows the proposed structure of a complex between p85α-NSH2 and the GIV-derived phosphopeptide pY1798ATLP (SEQ ID NO:6). In the predicted binding mode, 8340, 8358, S361, T369, and K382 of p85α-NSH2 make hydrogen bonds with the pY1798 of GIV in the manner similar to the established crystal structure of p85α-NSH2 bound to pY721 of c-Kit. In addition, the backbone atoms of N378, L380, and N417 and side chains of N377 and N378 make additional hydrogen bonds with the backbone and side-chain atoms of GIV's pY1798ATLP peptide.
Figure 14C:
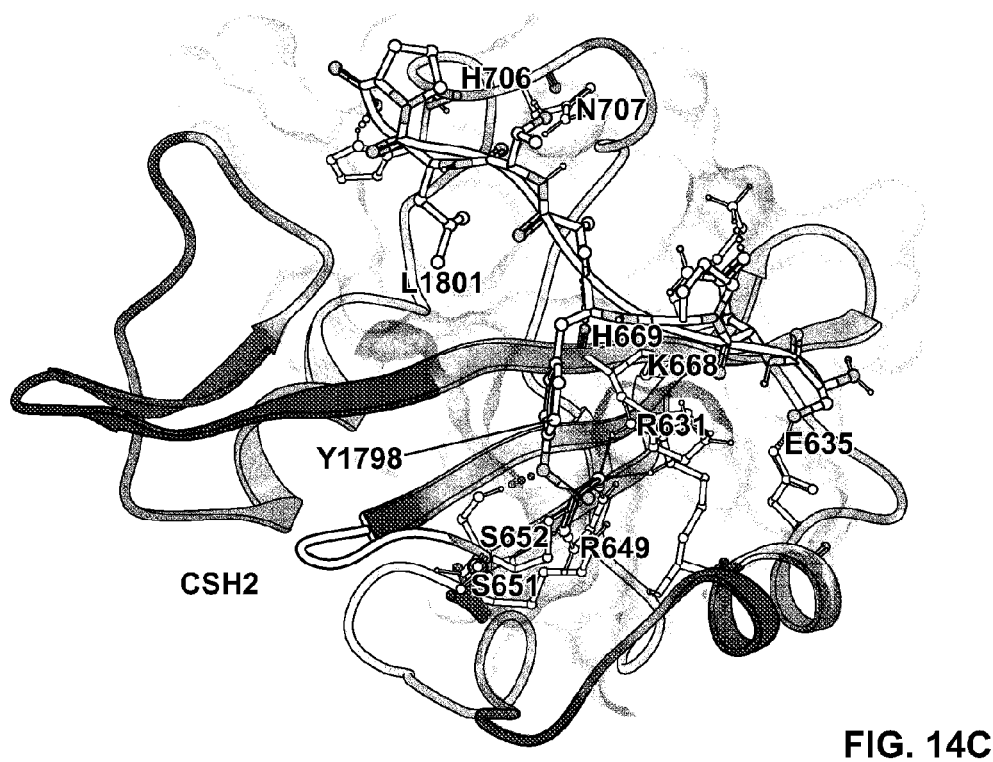
FIG. 14C shows the proposed structure of a complex between p85α-CSH2 and the GIV-derived pY1798ATLP phosphopeptide (SEQ ID NO:6). In the predicted binding mode, R631, R649, S651, and S652 of p85α-CSH2 make hydrogen bonds with the pY1798 of GIV in the manner identical to that predicted for pY1764 (A), and similar to the established crystal structure of p85α-CSH2 bound to pY751 of PDGFRβ. L1801 in position +3 of GIV-pY1798ATLP peptide is buried in the hydrophobic pocket of p85α-CSH2 typically occupied by the methionine in the YXXMX consensus (SEQ ID NO:18). The overall hydrogen bonding is similar to that observed in the case of PDGFRβ-pY751 peptide and no steric clashes are observed. D. Proposed structure of a complex between p85α-NSH2 and the GIV-derived pY1764FISS phosphopeptide (SEQ ID NO:5). In the predicted binding mode, 8340, R358, S361, T369, and K382 of p85α-NSH2 make hydrogen bonds with the pY1764 of GIV in the manner identical to that predicted for pY1798, and similar to the established crystal structure of p85α-NSH2 bound to pY721 of c-Kit. In addition, the backbone atoms of N378, L380, and N417 and side chains of N377 and N378 make additional hydrogen bonds with the backbone and side-chain atoms of GIV's pY1764FISS peptide.
Figure 14D:
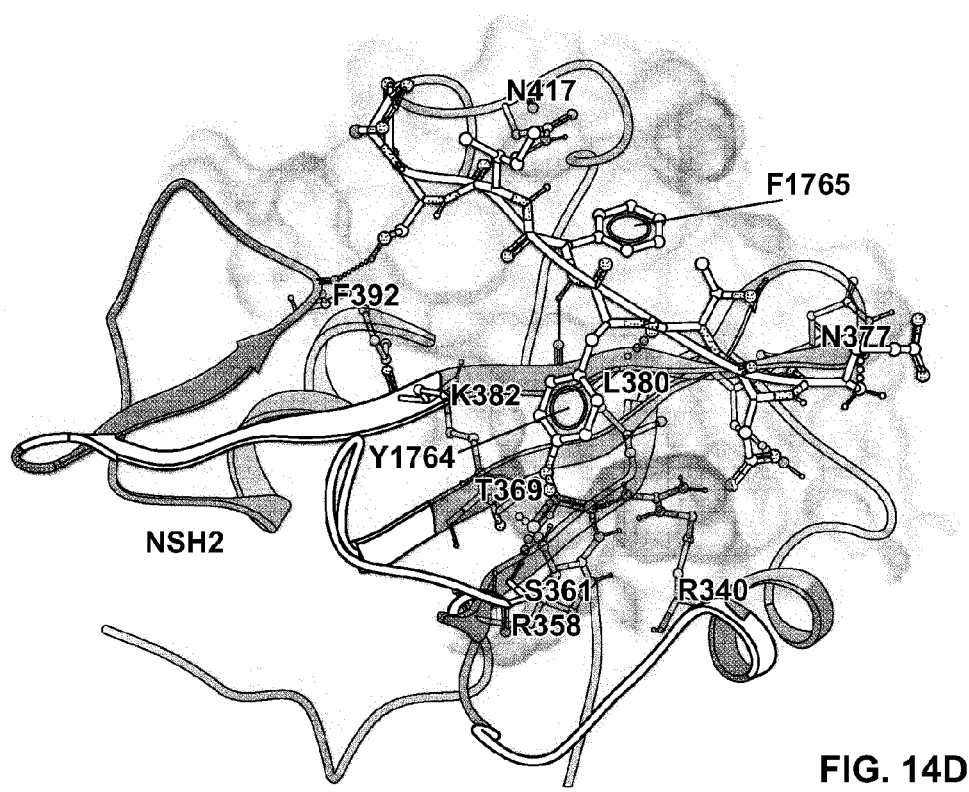
FIG. 14 provides molecular models of the interfaces between SH2 domains of p85α and the GIV-derived phosphopeptides.

Tyrosine signaling pathways have been implicated in the activation of class I PI3Ks via direct binding to the SH2 domains of the p85α regulatory subunit of PI3Ks or indirect binding to other SH2 domain-containing proteins/adaptors (Piccione et al., Biochemistry 32:3197-02, 1993). To investigate whether tyrosine phosphorylated GIV binds to the SH2 domain containing proteins, pull-down assays were performed using sham-treated or in vitro EGFR-phosphorylated His-GIV CT with a panel of GST-tagged SH2 adaptors immobilized on glutathione beads. Generally, essential features of specific phosphoprotein/SH2 protein interactions can be reconstituted using a phosphopeptide (derived from the phosphoprotein) and the SH2 domain(s) fragment of the SH2 protein (Songyang et al., Cell 72:767-78, 1993). Here, phosphorylated, but not sham-treated His-GIV CT bound to the C-terminal SH2 domain of p85α (p85α-CSH2) and to a lesser extent to the N-terminal SH2 domain of p85α (p85α-NSH2) (FIG. 4A). These interactions were specific because no binding was detected with GST or other SH2 domains (c-Src, Gab1, Grb2). Phosphorylation of His-GIV CT by both EGFR and Src kinase triggered binding to GST-p85α-CSH2 (FIG. 4B) and GST-p85α-NSH2 (FIG. 5B), indicating that both receptor and non-receptor tyrosine kinases can generate phosphotyrosines on GIV's C-terminus that are recognized by SH2 domains of p85α. In addition, GST-p85α-CSH2 also bound endogenous GIV from lysates of EGF-stimulated Cos7 cells, but not from serum starved cells (FIG. 13A), demonstrating that p85α can bind full length GIV. To confirm whether the GIV-p85α interaction occurs in vivo, endogenous (FIG. 4C-D) and exogenously expressed (FIG. 13B) FLAG-tagged GIV were immunoprecipitated from HeLa and Cos7 cells, respectively and immunoblotted for p85α. Both endogenous (FIG. 4C-D) and exogenously expressed (FIG. 13B) GIV co-immunoprecipitated with p85α consistently and exclusively after ligand stimulation of starved cells. The formation of endogenous GIV-p85α complexes coincided with the timing of peak tyrosine phosphorylation of GIV and peak Akt activation, all occurring at ~5 min after ligand stimulation (FIG. 4C). Furthermore, such GIV-p85α association occurred regardless of the ligand used to stimulate the cells (FIG. 4D), demonstrating that assembly of GIV-p85α complexes in cells can be triggered by multiple growth factors. While both endogenous GIV (FIG. 13C) and FLAG-tagged GIV-WT (FIG. 4E) co-immunoprecipitated with endogenous ligand-activated EGFR and p85α, the FLAG-tagged GIV-YF mutant in which tyrosines 1764 and 1798 are mutated to phenylalanines co-immunoprecipitated only with ligand-activated EGFR, but not with p85α (FIG. 4E), thereby demonstrating that these phosphotyrosines are required for the formation of GIV-p85α complexes in vivo, but not for the GIV-EGFR interaction. These results show that upon ligand stimulation GIV directly binds ligand-activated EGFR and enhances the recruitment of p85α (PI3Ks) to the activated receptor via its C-terminally located phosphotyrosines, which serve as binding sites for the SH2 domains of p85α.

Homology Models of the GIV-p85α Interface(s) Resemble Canonical Phosphotyrosine-SH2 Interactions.

To determine the relative contribution of tyrosines 1764 and 1798 towards the observed interaction between GIV's C-terminus and the SH2 domains of p85α, pull-down assays were carried out on in vitro phosphorylated His-GIV-CT WT and single tyrosine mutant proteins (His-GIV CT Y1764F, and His-GIV CT-Y1798F) with GST-p85α-CSH2. When EGFR kinase was used to phosphorylate these His-GIV CT proteins, WT and Y1798F mutant proteins bound p85α-CSH2, whereas the Y1764F mutant did not (FIG. 5A). By contrast, when Src kinase was used to phosphorylate the His-GIV CT proteins, WT and the Y1764F mutant bound p85α-CSH2, whereas the Y1798F mutant did not (FIG. 5A). Thus, EGFR kinase triggers GIV-p85α binding largely via phospho-Y1764 and Src kinase triggers GIV-p85α binding largely via phospho-Y1798 (FIG. 2D). These results demonstrate that EGFR and Src kinases create two distinct phosphotyrosine-binding sites on GIV for p85α-CSH2. Similarly, both phosphotyrosines are able to directly bind GST-p85α-NSH2 (FIG. 5B), demonstrating that both N- and C-terminal SH2 domains of p85α have the ability to bind either of the two phosphotyrosines on GIV.

Figure 5D:
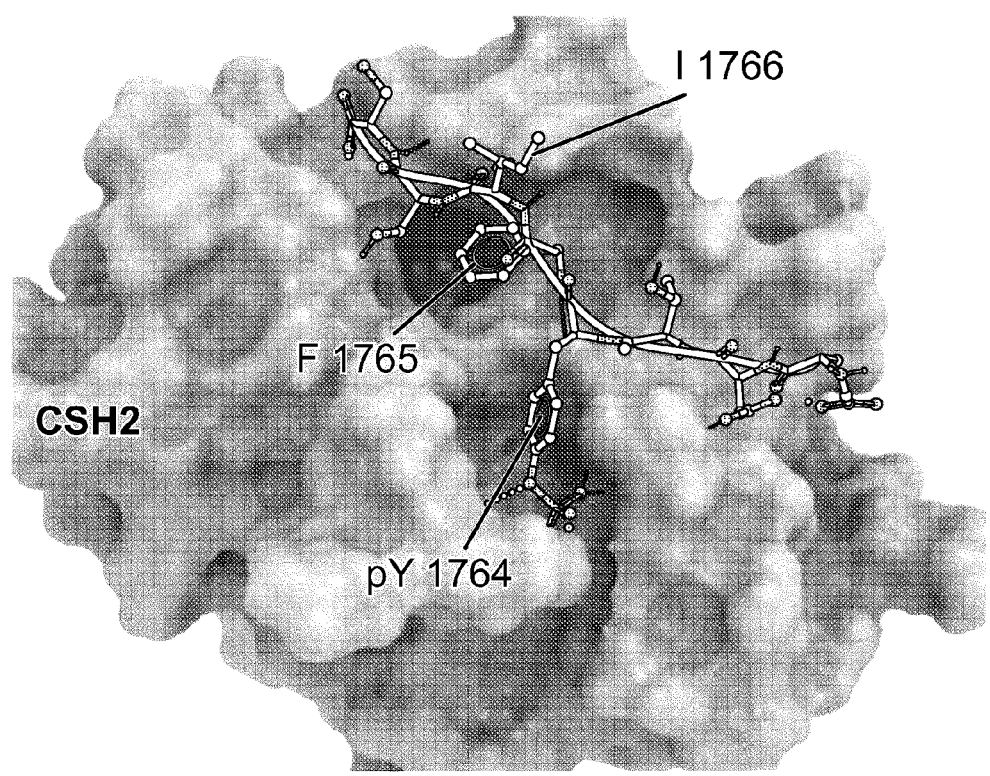
FIG. 5D-E shows molecular models of the interfaces between SH2 domains of p85α and the GIV-derived phosphopeptides.
Figure 5E:
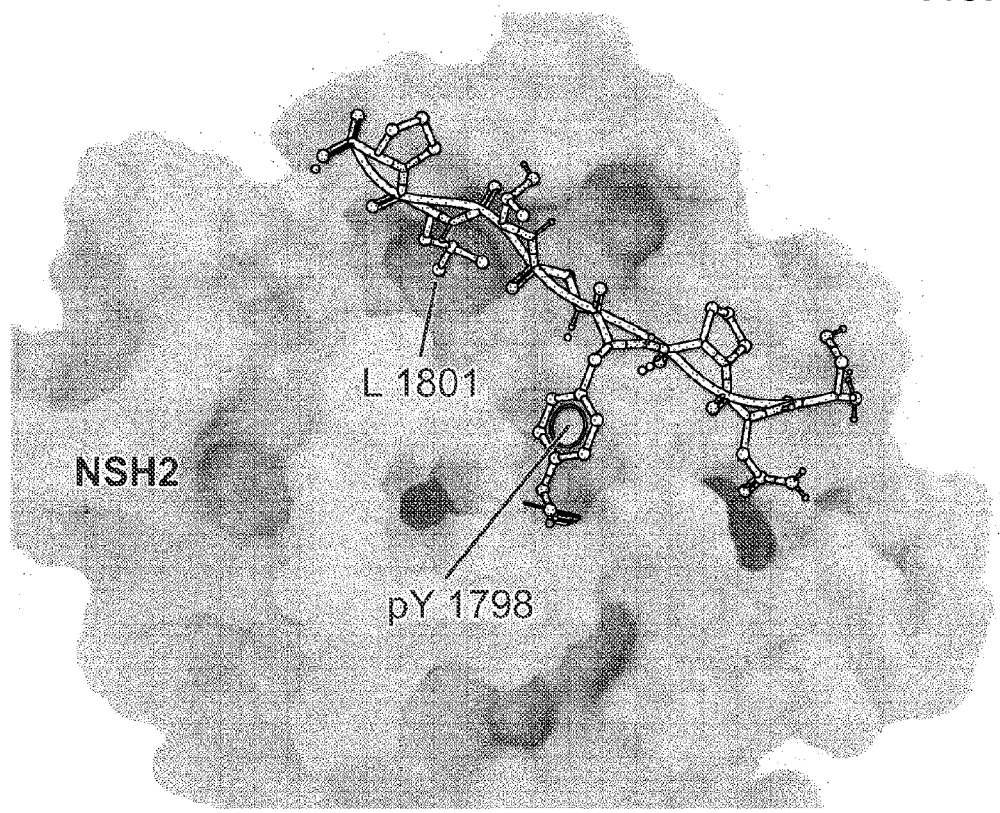

GIV's phosphopeptides (pY$^{1764}$FISS and pY$^{1798}$ATLP) were aligned with phospho-tyrosine peptides from other proteins that are known to bind p85α-CSH2 (FIG. 5C). This alignment demonstrates that GIV's phosphopeptides do not resemble the canonical consensus sequence for p85α-C/NSH2 binding peptides, pY[VMLI]XM (SEQ ID NO:4) (Abagyan et al., J. Mol. Biol. 235:983-02, 1994; and Abgayen et al., J. Comp. Chem. 15:488-06, 1994). Homology modeling was used to gain insights into how these non-canonical phosphopeptides of GIV interact with the C- or N-terminal SH2 domains of p85α. Models (FIG. 5D-E and FIG. 14) were created with the Internal Coordinate Mechanics (ICM) software (Pauptit et al., Acta Crystallographica Section D, 57:1397-1404, 2001) using the crystal structures of p85-CSH2 in complex with pY751 peptide from PDGFRβ (Nolte et al., Nature Structural Biol, 3:364-374, 1996) or p85-NSH2 bound to c-Kit phosphotyrosyl peptide (Ghosh et al., Mol. Cell Biol. 21:2338-54, 2010) as templates. The side chains of both phosphotyrosines of GIV make multiple hydrogen bonds with R631, R649, S651, and S652 in the case of p85α-CSH2 and with 8340, 8358, 5361, T369, and K382 in case of p85α-NSH2, whereas the backbones of both GIV's phosphopeptides form hydrogen bonds with H669, H706, N707 in the case of p85α-CSH2 and N378, L380, N417 in the case of p85α-NSH2 (FIG. 5D-E, FIG. 14A-D). Multiple polar and non-polar contacts also exist between the phosphotyrosine peptides of GIV and the SH2 domains of p85α (e.g., F1765 of GIV-pY$^{1764}$FISS bound a shallow hydrophobic pocket occupied by V752 of PDGFRβ and M724 of c-Kit in their respective complex structures with p85α-CSH2 and p85α-NSH2, whereas L1801 of GIV-pY$^{1798}$ATLP occupies the deep cavity which binds M754 of PDGFRβ and M724 of c-Kit in their respective complex structures with p85α-CSH2 and p85α-NSH2). These analyses demonstrate that the sequences flanking both phosphotyrosine peptides of GIV are equally compatible with direct and specific binding to either SH2 domains of p85α and provide a structural basis for our findings in GST pull-down assays (FIG. 5A-B).

GIV's Phosphotyrosines Couple PI3K to Ligand-Activated RTKs.

Figure 6A:
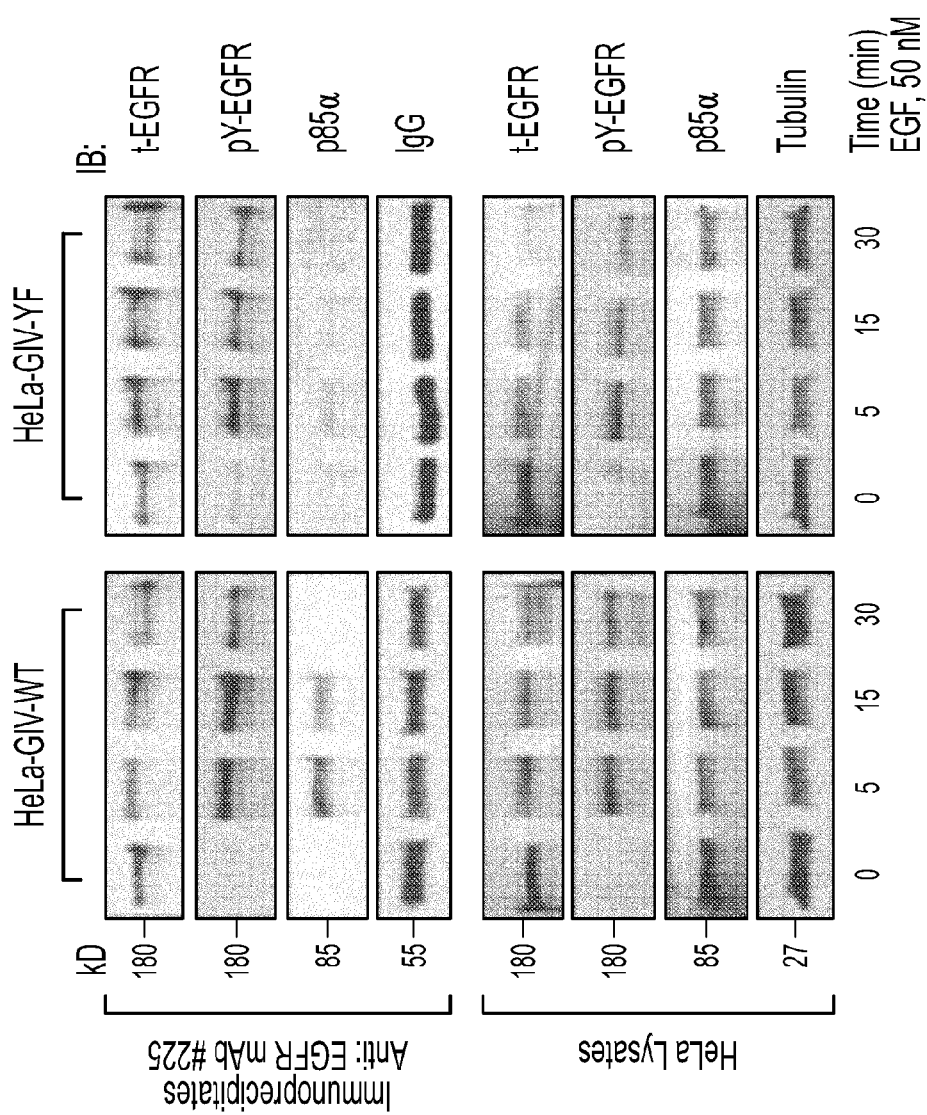
FIG. 6A shows that p85α is recruited to ligand-activated EGFR in HeLa-GIV-WT, but not in HeLa-GIV-YF cells. Lysates (bottom panels) prepared from starved and EGF-stimulated HeLa-GIV-WT and HeLa-GIV-YF (GIV-Y1764, Y1798F) cells were incubated with anti-EGFR (#225) IgG. Immune complexes (top panels) were analyzed for total (t-EGFR) and activated (pY-EGFR) EGFR and p85α by immunoblotting (IB). p85α coimmunoprecipitated with EGFR in GIV-WT cells at 5 and 15 min, but was poorly detected in EGFR-bound complexes from GIV-YF cells at corresponding times.
Figure 6B:
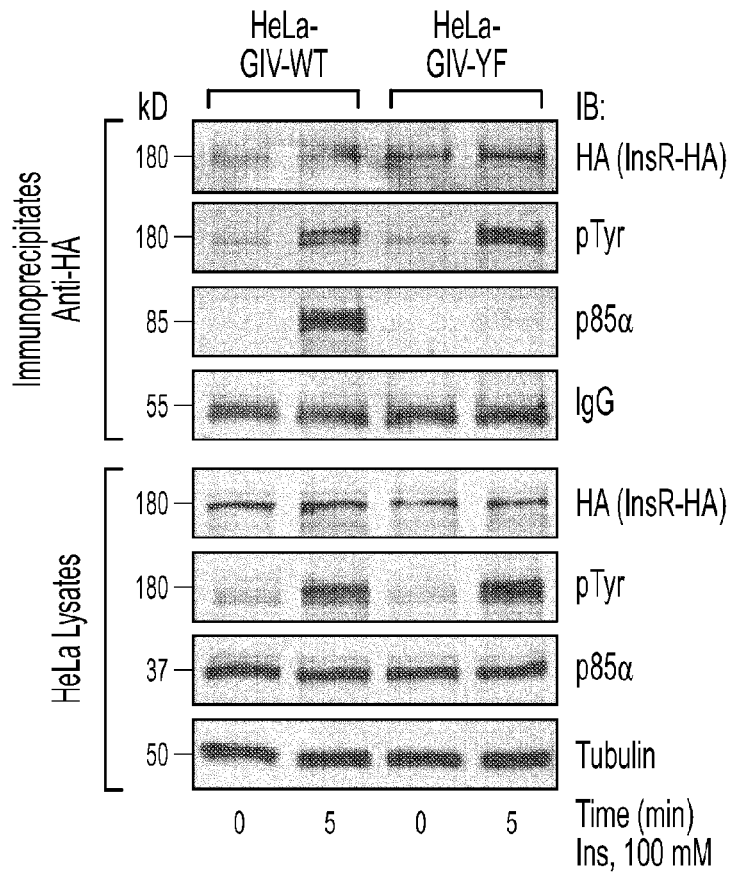
FIG. 6B shows that p85α is recruited to ligand-activated insulin receptor (InsR) in HeLa-GIV-WT, but not in HeLa-GIV-YF cells. Lysates (bottom panel) of starved (0.2% FBS, 16 h) and insulin-treated HeLa-GIV-WT and HeLa-GIV-YF (GIV Y1764, 1798F) cells transiently expressing HA-tagged insulin receptor (InsR-HA) were incubated with Anti-HA mAb Immune complexes (top panel) were analyzed for InsR (HA), pTyr, and p85α by immunoblotting (IB). p85α coimmunoprecipitated with InsR at 5 min in GIV-WT cells, but not in GIV-YF cells.

Because GIV directly binds ligand-activated EGFR (Holt et al., Mol. Cell Biol. 14:42-49, 1994; and Rordorf-Nikolic, J. Biol. Chem. 270:3662-66, 1995) and p85α, whether GIV (or more specifically its phosphotyrosines) facilitates the recruitment of PI3K to activated EGFR was assessed. EGFR was immunoprecipitated from HeLa-GIV-WT and HeLa-GIV-YF cells and the receptor-bound proteins were analyzed for p85α by immunoblotting. In HeLa-GIV-WT cells EGFR transiently and maximally associated with p85α at 5 min after ligand stimulation, whereas in HeLa-GIV-YF cells p85α recruitment was dramatically reduced (FIG. 6A). Thus, tyrosine phosphorylation of GIV is critical for effective formation and/or stabilization of p85α-EGFR signaling complex. Identical results were obtained when insulin receptor was immunoprecipitated from HeLa-GIV-WT and HeLa-GIV-YF cells expressing HA-tagged insulin receptor (FIG. 6B), indicating that tyrosine phosphorylation of GIV is also critical for effective formation and/or stabilization of a p85α-InsR signaling complex. These results demonstrate that interactions between RTKs and p85α in vivo are enhanced by GIV via its C-terminal phosphotyrosines.

Tyrosine Phosphorylated GIV Activates PI3K at the Plasma Membrane.

Figure 6C:
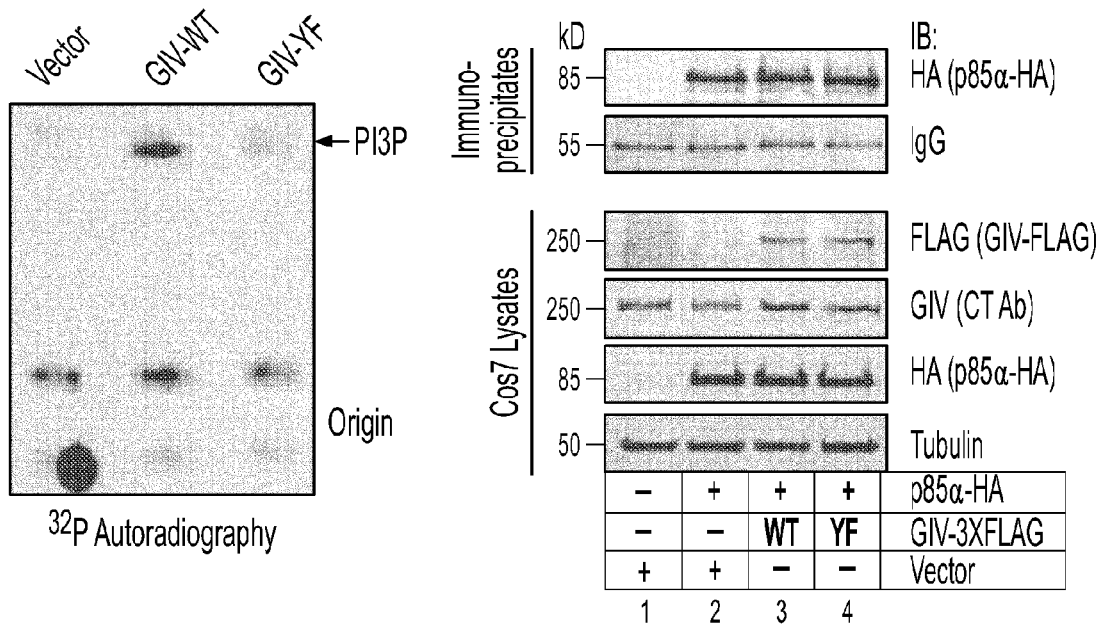
FIG. 6C shows that GIV-WT, but not GIV-YF enhances PI3K activity in cells. Cos7 cells were co-transfected with p85α-HA and either wild-type (WT) or phosphotyrosine-mutant (YF) of GIV-FLAG and maintained in the presence of 2% FBS for 24 hours prior to lysis. Equal aliquots of lysates (right, bottom) were incubated with HA mAb and protein G beads to immunoisolate p85α-HA (PI3K) (right, top). PI3-kinase assays (left) were carried out using equal aliquots of immunoisolated p85α-HA(PI3K), phosphatidylinositol, and [γ-$^{32}$P] ATP. Lipid end products were extracted in organic solvents, resolved by thin layer chromatography and imaged by autoradiography. PI3K is activated and PI3P is produced in cells expressing GIV-WT, but not in those expressing vector control or GIV-YF (compare expression of FLAG-tagged GIV in lysates; bottom-right).
Figure 6D:
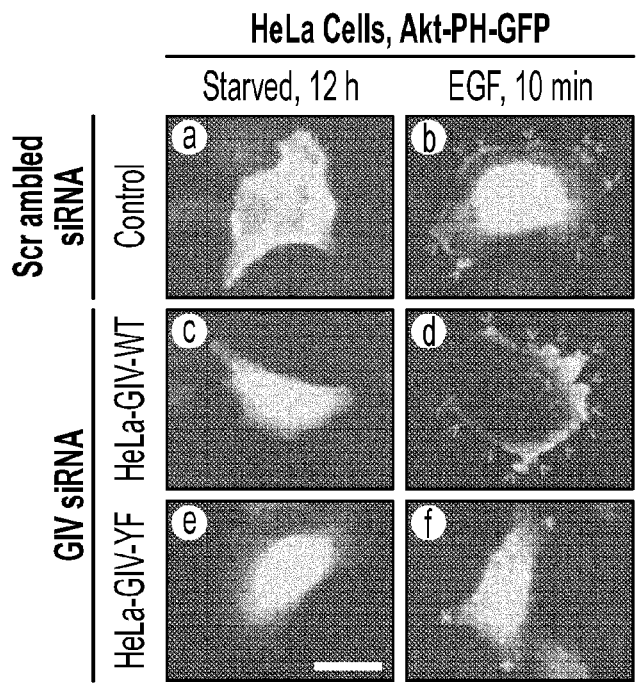
FIG. 6D shows that EGF triggers membrane translocation of GFP-fused PH domain of Akt kinase in control HeLa and HeLa-GIV-WT cells, but not in HeLa-GIV-YF cells. HeLa cells stably expressing either siRNA-resistant wild-type GIV (GIV-WT), or phosphotyrosine-mutant GIV (GIV-YF), or vector control were first treated with scrambled or GIV siRNA as indicated followed by transient transfection with Akt-PH-GFP plasmid. Cells were subsequently starved (0.2% FBS, 16 h) or treated with EGF for 10 min and then fixed and stained for GFP (yellow) and nucleus/DAPI (blue), and analyzed by confocal microscopy. In starved cells, both Akt-PH and Btk-PH probes show predominant cytosolic localization (a, c, and e). Upon EGF stimulation, both PH-domain probes shift from cytosol to the PM within 10 min in control and GIV-WT cells (b and d). EGF triggered cytosol-to-PM re-distribution of both Akt-PH domain was abolished when cells were pre-incubated with the PI3K inhibitor LY294000, indicating that recruitment of GFP-tagged PH probes to the PM is dependent on PIP3 production by activated PI3K. In the case of GIV-YF cells Akt-PH probe remained cytosolic after EGF treatment (panel f). Identical results were observed when Btk-PH domain was used instead of Akt-PH domain. Bar=10 μM. E) Tyrosine phosphorylation of GIV and its association with p85α-subunit of PI3K increase during metastatic progression in 21T-series of breast carcinoma cell lines. Equal aliquots of lysates (left) from 21 T series of cells (16N, NT, and MT2) were separated by SDS-PAGE and analyzed for GIV, p85α, phospho-Akt (pAkt), Gαi3, and tubulin by immunoblotting (IB). Aliquots of these lysates (normalized to equal abundance of GIV protein) were incubated with anti-GIV (Girdin CTAb) or preimmune IgG Immune complexes (right) were analyzed by two-color immunoblotting (IB) for GIV, p85α, and pTyr using LI-COR Odyssey. The abundance of GIV in the immunoprecipitates were equal among 21T cell lines (top panel), but the intensity of pTyr signals was strongest in MT2, undetectable in 16N, and intermediate in NT. Yellow pixels in the overlay of GIV and pTyr (Green) images (Merge panel) confirm that tyrosine phosphorylation of GIV increases during metastatic progression of breast carcinoma (compare lanes 1-3). Level of p85α in the immunoprecipitates was highest in MT2, virtually undetectable in 16N, and intermediate in NT cells.
Figure 15:
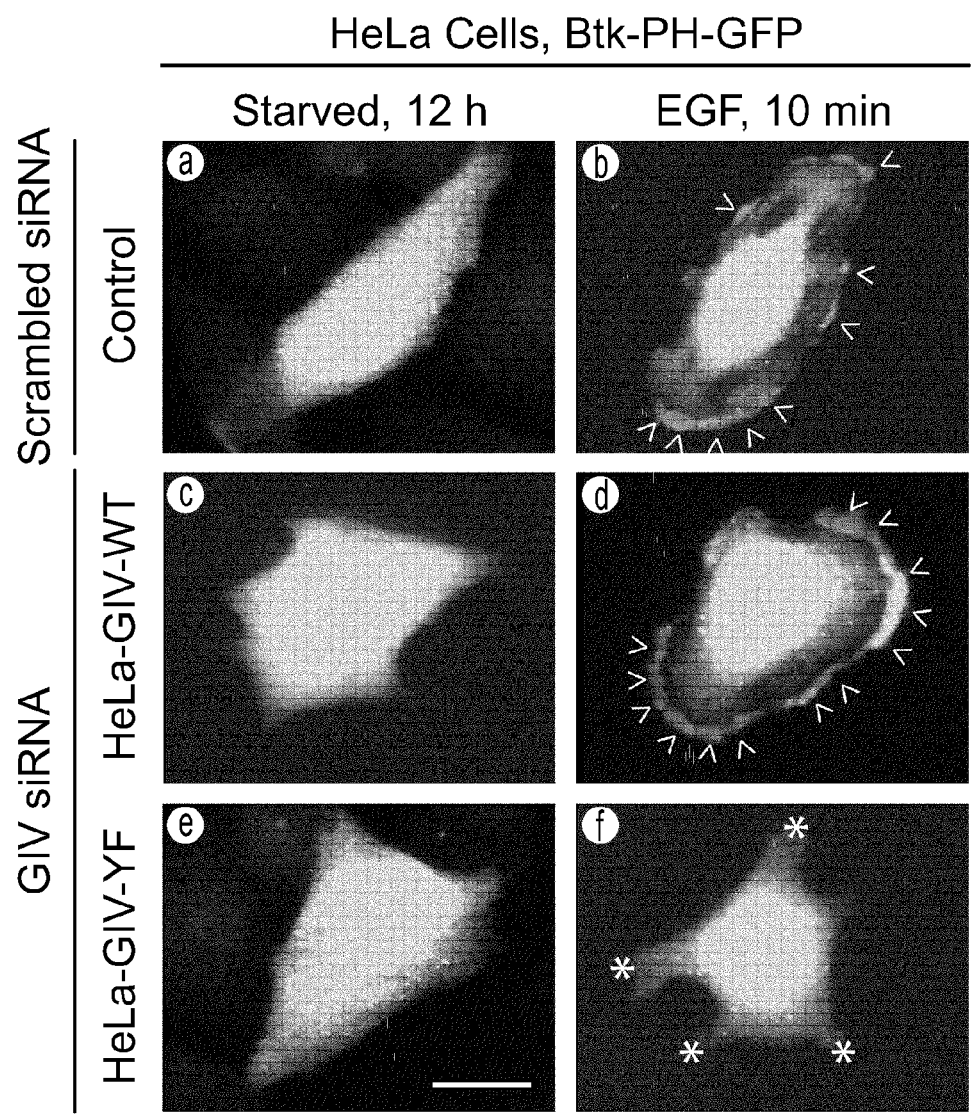
FIG. 15 shows that EGF triggers membrane translocation of GFP-fused PH domain of Btk kinase in control HeLa and HeLa-GIV-WT cells, but not in HeLa-GIV-YF cells. HeLa cells stably expressing either siRNA-resistant wild-type GIV (GIV-WT), or phosphotyrosine-mutant GIV (GIV-YF), or vector control were first treated with scrambled or GIV siRNA as indicated followed by transient transfection with Btk-PH-GFP plasmid. Cells were subsequently starved (0.2% FBS, 16 h) or treated with EGF for 10 min and then fixed and stained for GFP (yellow) and nucleus/DAPI (blue), and analyzed by confocal microscopy. In starved cells, Btk-PH probe showed predominant cytosolic localization (a, c, and e). Upon EGF stimulation, Btk-PH probe shifted from cytosol to the PM within 10 min in control and GIV-WT cells (b and d). In the case of GIV-YF cells both Akt and Btk PH probes remained cytosolic after EGF treatment (panel f). Bar=10 μM.

Binding of phosphotyrosines to both SH2 domains of the regulatory p85α-subunit is known to activate the catalytic p110-subunit of PI3K (Cantley, Science, 296:1655-57, 2002), which triggers the production of phosphatidylinositol-3,4,5-trisphosphate (PI-3,4,5P; PIP3) (Cuevas et al., J. Biol. Chem. 274:27583-89, 1999; Whitman et al., Nature 332:644-646, 1988; Fry et al., EMBO J. 4:3173-78, 1985; Wang et al., Biochem. J. 408:221-30, 2007; and Zhang et al., Am, J. Physiol. 278:F155-64, 2000). Because phosphotyrosines of GIV directly bind SH2 domains of p85α, this interaction activates PI3K. To demonstrate this, in vitro PI3-kinase assays were carried out (Kavran et al., J. Biol. Chem. 273:30497-08, 1998) using purified phosphoinositides and immunoisolated p85α(PI3K) from cells expressing vector, GIV-WT or GIV-YF. The activity of PI3K, as determined by the extent of production of PI3P, was low in cells expressing vector and GIV-YF, and increased exclusively and significantly in cells expressing GIV-WT (FIG. 6C), indicating that GIV's tyrosines are indeed required for enhancement of PI3K activity in cells. To determine if this activation of PI3K occurs at the plasma membrane (PM) and whether levels of second messenger, PIP3 are elevated, the GFP-tagged PH domain of Akt (Akt-PH-GFP, FIG. 6D), which recognizes PIP3 (Kontos et al., Mol. Cell. Biol. 18:4131-40, 1998; Servant et al., Science, 287:1037-40, 2000; and Watton et al., Curr Biol. 9:433-36, 1999), was expressed in control HeLa, HeLa-GIV-WT and HeLa-GIV-YF cells and its EGF-dependent recruitment to the PM was monitored by fluorescence confocal microscopy. In starved HeLa control cells Akt-PH-GFP was mostly cytosolic, but it was recruited to the PM within 10 min after EGF stimulation, indicating that PI3K was activated and PIP3 was generated at the PM after ligand stimulation, thereby making it favorable for the recruitment of the PH-domain of Akt. In HeLa-GIV-WT cells the pattern was identical with robust EGF-triggered PM-recruitment of Akt-PH-GFP. By contrast, in HeLa-GIV-YF cells Akt-PH-GFP remained cytosolic before and after EGF treatment, indicating that the abundance of PIP3 at the PM does not change in these cells after ligand stimulation and remains unfavorable for recruitment of the PH-domain of Akt. To circumvent the concerns that altered localization of Akt in HeLa-GIv-YF cells could be due to changes in the previously reported interaction between GIV and Akt (Enomoto et al., Dev. Cell 9:389-02, 2005; and Anai et al., J. Biol. Chem. 280:18525-35, 2005) similar assays were performed using GFP-tagged PH domain of Btk (Btk-PH-GFP, FIG. 15), another validated fluorescent reporter for PIP3 (Varnai et al., J. Biol. Chem. 274:10983-89, 1999). Findings with Btk-PH domain were identical to those with Akt-PH domain, demonstrating that EGF-triggered production of PIP3 is impaired in HeLa-GIV-YF cells. In conclusion, ligand-stimulated activation of PI3K and production of PIP3 at the PM requires tyrosine phosphorylation of GIV.

Tyrosine Phosphorylation of GIV and its Association with p85α Increases During Metastatic Progression of Breast Carcinoma.

Figure 6E:
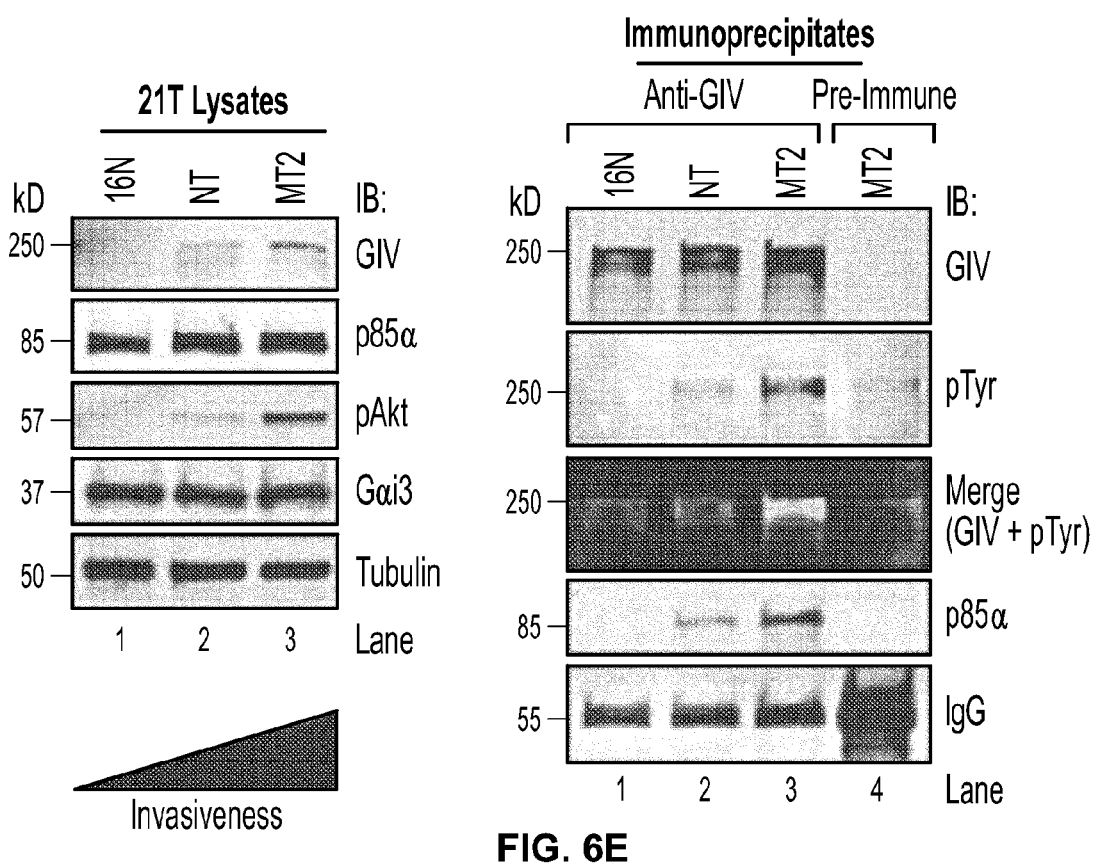
FIG. 6 illustrates that tyrosine phosphorylation of GIV stabilizes receptor-p85α(PI3K) complexes and augments PI3K activity.

The abundance of GIV protein and mRNA increases during metastatic progression in colorectal and breast carcinomas (Garcia-Marcos et al., FASEB J. 25:590-99, 2011). Moreover, this increase coincides with increased PI3K-Akt activity in tumor cells (Band et al., Cancer Res. 50:7351-57, 1990; and Qiao et al., Cancer Res. 67:5293-99, 2007). It was therefore investigated in 21T series of human mammary cells (16N, NT and MT2) (Garcia-Marcos J. Biol. Chem. 285:12765-77, 2010) whether tyrosine phosphorylation of GIV and its association with p85α increases during metastatic progression. The 21T cells were derived by successive biopsies from a single patient with breast cancer. 16N is from the normal breast, NT from the primary tumor (invasive ductal carcinoma), and MT2 from the metastatic pleural effusions. As shown in FIG. 6E, the abundance of full length GIV and extent of Akt phosphorylation were lowest in 16N, intermediate in NT and highest in MT2 (See also, Enomoto et al., Dev. Cell 9:389-02, 2005; Jiang et al., Cancer Res., 68:1310-18, 2008; Kitamura et al., Nat. Cell Biol. 10:329-337, 2008, Miyake et al., Circ Res, 108:1170-1179, 2011; Enomoto et al., Neuron 63:774-787, 2009; and Puseenam et al., Exp. Cell. Res. 315:3370-80, 2009) Immunoprecipitation of equal amounts of GIV from lysates of these 21T cell lines and immunoblotting for pTyr and p85α revealed that tyrosine phosphorylation of GIV and the amount of p85α co-immunoprecipitated were lowest in 16N, intermediate in NT, and highest in MT2 cells (FIG. 6E). These results demonstrate that tyrosine phosphorylation of GIV and its association with p85α increases during metastatic progression of breast carcinoma and indicates that GIV-dependent PI3K activation plays a role during tumor invasion.

Tyrosine Phosphorylation of GIV is Required for Akt-Dependent Phosphorylation of GIV at S1416.

Figures 7A, 7B:
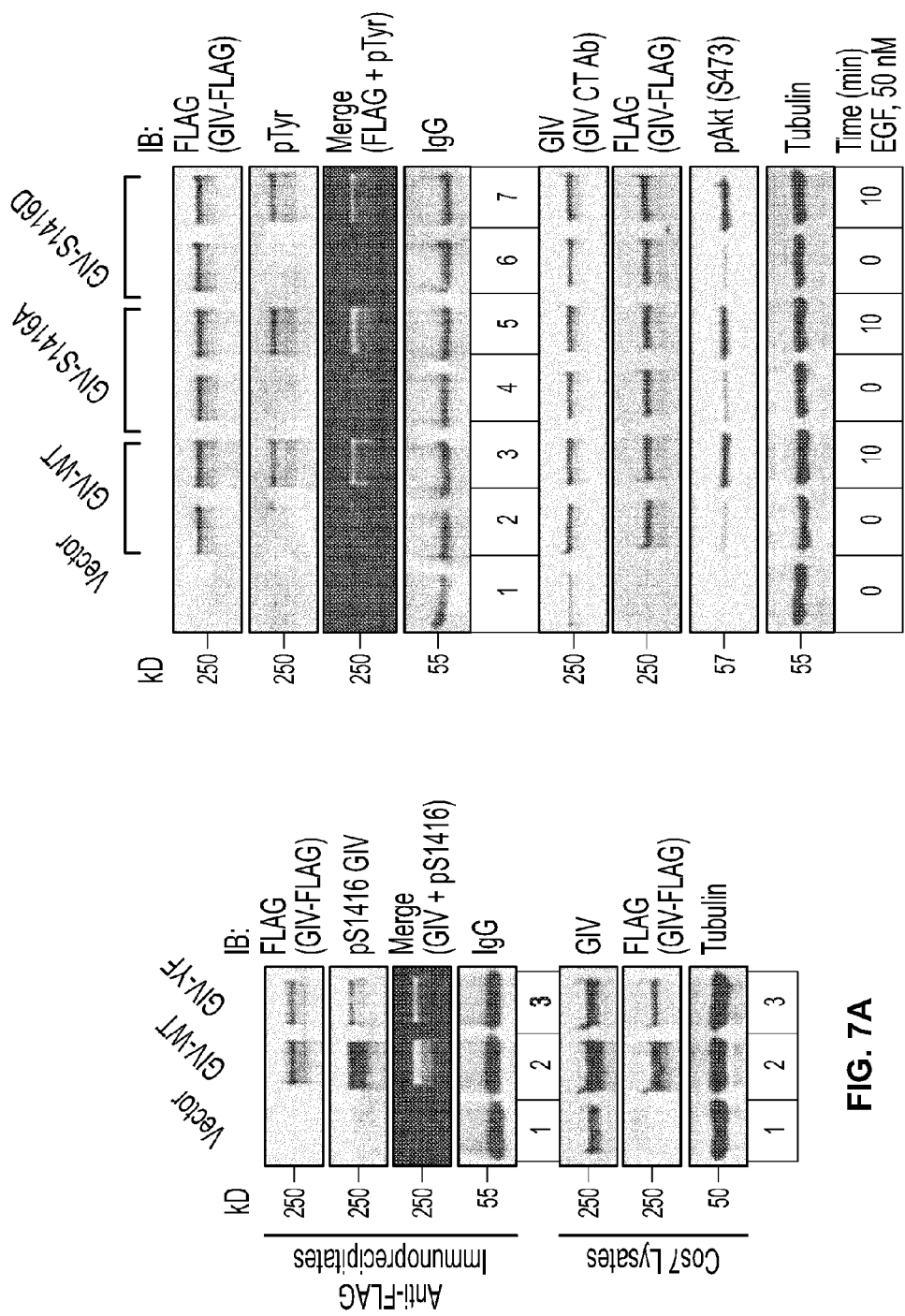
FIG. 7A shows that Akt efficiently phosphorylates GIV at Ser(pS) 1416 in cells expressing GIV-WT, but not GIV-YF. Cos7 cells expressing vector or FLAG-tagged GIV-WT or GIV-YF were maintained in the presence of 2% FBS prior to lysis. Equal aliquots of lysates (bottom) were incubated with FLAG mAb and protein G beads. Immune complexes (top) were analyzed by two-color immunoblotting (IB) for FLAG (GIV) and pS1416 GIV using Li-COR Odyssey. Yellow pixels in the overlay of GIV-FLAG (green) and pS1416 GIV (22) images (Merge panel) confirm that the extent of Akt-dependent phosphorylation of GIV at S1416 is enhanced in cells expressing GIV-WT (lane 2) as compared to those expressing GIV-YF (lane 3).
FIG. 7B shows that EGF stimulates tyrosine phosphorylation of both phosphorylation-deficient (S1416A) and phosphorylation-mimicking (S1416D) mutants of GIV, at levels similar to GIV-WT. Cos7 cells transiently transfected with FLAG-tagged wild-type (GIV-WT), or phosphoserine mutants of GIV (GIV-S1416A and GIV-S1416D), or vector control were starved (0 min) or stimulated with 50 nM EGF for 10 min prior to lysis. Equal aliquots of cell lysates (bottom) were incubated with anti-FLAG mAb. Immunoprecipitated complexes (top) were analyzed by two-color immunoblotting (IB) for GIV and pTyr using LI-COR Odyssey. Grayscale image for GIV (top panel) shows that GIV-FLAG is immunoprecipitated in lanes 2-7, but not in vector control (lane 1). pTyr panel shows that tyrosine phosphorylation occurred upon ligand stimulation (lanes 3, 5, 7). Yellow pixels of the overlaid GIV (22) and pTyr (green) images (Merge panel) confirm that the immunoprecipitated GIV-WT (lane 3) and both phosphoserine mutants of GIV (lanes 5, 7) were tyrosine phosphorylated equally efficiently after EGF treatment.

Multiple biological functions of GIV (e.g., cancer invasion and metastasis, neoangiogenesis, control of cell size during development, neuronal migration, and vascular repair after injury) have been attributed to another key phosphorylation event, i.e. phosphorylation of GIV by Akt at the critical serine, 51416 (Enomoto et al., Dev. Cell 9:389-02, 2005; Jiang et al., Cancer Res., 68:1310-18, 2008; Kitamura et al., Nat. Cell Biol. 10:329-337, 2008; and Miyake et al., Circ Res, 108:1170-1179, 2011). The relationship between tyrosine-phosphorylation and Akt-dependent serine phosphorylation of GIV was next investigated. GIV-FLAG WT, but not GIV-FLAG YF was efficiently phosphorylated at S1416 (FIG. 7A), indicating that tyrosine phosphorylation of GIV is a prerequisite for efficient Akt-dependent serine phosphorylation of GIV. The converse is not true in that phosphorylation at S1416 is not a prerequisite for tyrosine phosphorylation of GIV. Both the phosphorylation-deficient S1416A and the phosphorylation-mimicking S1416D mutants of GIV were tyrosine phosphorylated as efficiently as GIV-WT (FIG. 7B), demonstrating that phosphorylation at S1416 does not affect tyrosine phosphorylation of GIV. Taken together, these findings demonstrate that tyrosine phosphorylation of GIV occurs upstream of and regulates the subsequent step of Akt-dependent phosphorylation of GIV at S1416.

Figure 1A:
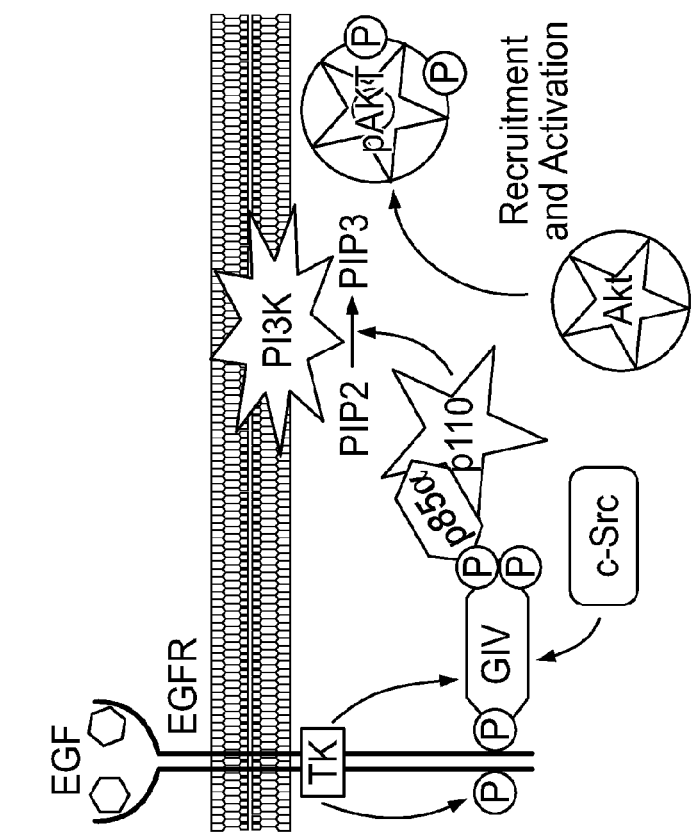
FIG. 1A shows a sequence of events at the plasma membrane (PM). Upon ligand stimulation, EGFR is activated and undergoes autophosphorylation. GIV is recruited to the autophosphorylated cytoplasmic tails of activated receptors. Subsequently activated receptor and non-receptor tyrosine kinases (like c-Src) phosphorylate GIV at two critical tyrosines. These phosphotyrosines serve as direct binding site for the SH2 domains of the regulatory p85α-subunit of PI3K. By being able to directly bind the ligand-activated receptor and p85α(PI3K), GIV stabilizes the receptor-p85α complexes, triggers the activation of PI3K, and augments the production of PtdIns-3,4,5-tri-phosphate (PIP3) at the PM. Thus, GIV works upstream of Akt and other such downstream signaling intermediates by providing PIP3 to their PH domains, which is critical for their recruitment and activation at the PM.

In summary, these results demonstrate that GIV is a substrate of multiple tyrosine kinases and that GIV's phosphotyrosines directly bind and activate PI3K-Akt at the plasma membrane (FIG. 1). Activated Akt subsequently phosphorylates GIV and triggers cell migration (Ghosh et al., J. Cell Biol. 182:381-93, 2008; Anai et al., J. Biol. Chem. 280:18525-35, 2005; and Garcia-Marcos et al., Proc. Natl. Acad. Sci. USA, 106:3178-83, 2009). Multiple receptors enhance PI3K activity and trigger cell migration via a common tyrosine phosphoprotein, GIV.

Example 2

Src Homology Domain 2-Containing Protein Tyrosine Phosphatase-1 (SHP-1) Binds and Dephosphorylates GIV/Girdin This example describes the identification of SHP-1 as the major and specific protein tyrosine phosphatase that catalyzes the dephosphorylation of tyrosine-phosphorylated GIV and that inhibits ligand-dependent tyrosine phosphorylation of GIV downstream of both growth factor receptors and GPCRs.

Materials and Methods

Reagents and Antibodies.

Unless otherwise indicated all reagents were of analytical grade and obtained from Sigma-Aldrich (St. Louis, Mo.). Cell culture media were purchased from Invitrogen (Carlsbad, Calif.). All restriction endonucleases and E. coli strain DH5α were purchased from New England Biolabs (Beverly, Mass.). E. coli strain BL21(DE3) was purchased from Invitrogen (Carlsbad, Calif.). Pfu ultra DNA polymerase was purchased from Stratagene (La Jolla, Calif.). Rabbit antisera against the coiled-coil region of GIV was raised as described (21). Mouse mAbs against hexahistidine (His), FLAG (M2) and α-tubulin were obtained from Sigma-Aldrich (St. Louis, Mo.) and against HA was purchased from Covance Inc. (Princeton, N.J.). Rabbit anti-Gαi3, anti-SHP-1, anti-SHP2, anti-total EGFR (cytoplasmic tail), anti-GIV/Girdin(T-13) IgGs were from Santa Cruz Biotechnology (Santa Cruz, Calif.), anti-p85α was from Millipore Inc, (CA), anti-phosphotyrosine was from BD Biosciences (MA), and anti-phospho-Akt (S473), anti-phospho-EGFR (Y1173) and anti-phospho-ERK1/2 IgGs were from Cell Signaling (Beverly, Mass.). Goat anti-rabbit and goat anti-mouse Alexa Fluor 680 or IRDye 800 F(ab')2 used for Odyssey Infrared Imaging were from Li-Cor Biosciences (Lincoln, Nebr.).

Plasmid Constructs and Mutagenesis.

Hexahistidine (6-His)- and GST-tagged human SHP-1 PTP (GENBANK accession number BC002523) cloned into pET28, and pET42 (Novagen) expression vectors, respectively, were generous gifts from Richard Anderson (University of Wisconsin, Madison) (22). For mammalian expression, human SHP-1 was cloned from pET28 and inserted between EcoR 1 and Xho 1 restriction sites of pcDNA 3. HA-tagged mouse SHP-1 (NM_013545.2) was cloned from pBS (Bluescript), a generous gift from Ulrike Lorenz (University of Virginia, Charlottesville, Va.) (23) and inserted between two EcoR1 restriction sites of pcDNA 3.1. To generate the GST-tagged ΔNSH2 (amino acids 166-end) and ΔN+CSH2 (amino acids 276-end) truncations of SHP-1 for use in in-vitro binding assays, corresponding fragments of human SHP-1 (NM_002831) were cloned from pcDNA3.1 and inserted between the Bam H1 and EcoR1 restriction sites of the pGEX 4T-1 vector. Cloning of His-GIV-CT (amino acids 1660-1870) into pET28b and GIV-FLAG into 3×FLAG-pCMV-14 were described previously (9). C-terminal HA-tagged c-Src (accession # NM_001025395) for mammalian expression was generated by cloning the entire coding sequence into pcDNA 3 between Xho1 and EcoR1 restriction site. GST-SHP-1 C453S, HA-SHP-1 C453S, His-GIV-CT Y1764F and Y1798F, c-Src-HA K295R (inactive) and Y527F (active) mutants were generated by site-directed mutagenesis (sequences of primers available upon request) using QuickChange kit (Stratagene, San Diego, Calif.) as per manufacturer's protocols. All constructs were checked by DNA sequencing.

Protein Expression and Purification.

GST, GST-SHP-1 (full length, wild-type and C453S mutant, and ΔNSH2 and ΔN+CSH2), His-SHP-1, and His-GIV-CT fusion constructs were expressed in E. coli strain BL21(DE3) (Invitrogen) and purified as described previously (7,9). Briefly, bacterial cultures were induced overnight at 25° C. with 1 mM isopropyl □-D-1-thiogalactopyranoside (IPTG). Pelleted bacteria from 1 L of culture were resuspended in 10 ml GST-lysis buffer [25 mM Tris-HCl, pH 7.5, 20 mM NaCl, 1 mM EDTA, 20% (v:v) glycerol, 1% (v:v) Triton X-100, 2× protease inhibitor cocktail (Complete EDTA-free, Roche Diagnostics)] or His-lysis buffer [50 mM NaH2PO4 pH 7.4, 300 mM NaCl, 10 mM imidazole, 1% (v:v) Triton X-100, 2× protease inhibitor cocktail (Complete EDTA-free, Roche Diagnostics)] for GST or His-fused proteins, respectively. After sonication (4×20 s, 1 min between cycles), lysates were centrifuged at 12,000 g at 4° C. for 20 min. Solubilized proteins were affinity purified on glutathione-Sepharose 4B beads (GE Healthcare) or HisPur Cobalt Resin (Pierce). Proteins were eluted, dialyzed overnight against PBS and stored at −80° C.

In Vitro Phosphorylation and Dephosphorylation Assays.

In-vitro kinase-phosphatase assays were carried out in tandem using the following protocol: First, the kinase assays were performed using purified His-GIV-CT (~3-5 µg per reaction) and commercially obtained recombinant tyrosine kinases (EGFR, Millipore Inc.; c-Src Cell Signaling) Reactions were started by addition of 1 mM ATP and carried out at 25° C. for 60 min in tyrosine kinase buffer [60 mM HEPES pH 7.5, 5 mM MgCl2, 5 mM MnCl2]. Phosphorylated His-GIV-CT was subsequently used as the substrate in in-vitro dephosphorylation assays using either purified His-SHP-1 (FIG. 1A), GST-SHP-1 WT, GST-SHP-1 C453S (FIG. 1C), HA-SHP-1 immunoisolated from COS7 cells (FIG. 1D), or lysates of COS7 cells immunodepleted of endogenous SHP-1 (FIG. 1F) as source for phosphatase. Phosphatase reactions were carried out at 30° C. for 60 min in phosphatase buffer [25 mM HEPES, 2.5 mM EDTA, 5 mM DTT, 50 mM NaCl, 65 ng/ul BSA at pH 7.4] and stopped by adding Laemmli's sample buffer and boiling at 100° C.

Cell Culture, Transfection and Lysis.

COS7 and HeLa cells were grown at 37° C. in DMEM supplemented with 10% FBS, 100 U/ml penicillin, 100 µg/ml streptomycin, 1% L-glutamine and 5% CO2. siRNA transfection of HeLa cells was carried out using Oligofectamine (Invitrogen) following the manufacturer's protocol. Oligos against human SHP-1 were from Santa Cruz Biotechnology. Briefly, HeLa cells at 70% confluence were transfected with 0.83 nM (final) of SHP-1 siRNA in Opti MEM. Transfection of COS7 cells with HA-SHP-1, GIV-3×FLAG, or c-Src-HA were carried out using GeneJuice (Novagen). Lysates used as a source for SHP-1 for in vitro dephosphorylation assays or as a source for GIV in immunoprecipitation assays were prepared by resuspending cells in lysis buffer [20 mM HEPES, pH 7.2, 5 mM Mg(CH3COO)2, 125 mM K(CH3COO), 0.4% Triton X-100, 1 mM DTT supplemented with sodium orthovanadate (500 µM), phosphatase (Sigma) and protease (Roche) inhibitor cocktails] and subsequently passing them through a 30 G needle at 4° C., and cleared (centrifuged at 14,000 g for 10 min) before use in subsequent experiments. Whole cell lysates used to study the extent of Akt and ERK phosphorylation were prepared by resuspending the entire cell pellet in Laemmli's sample buffer and boiling at 100° C.

In Vivo Phosphorylation Assays.

For in vivo phosphorylation assays on endogenous GIV, HeLa cells were serum starved for 12-16 h prior to stimulation with 50 nM of EGF (Invitrogen). For in vivo phosphorylation assays using overexpressed GIV, FLAG-tagged GIV was co-expressed with either EGFR, Src, or SHP-1 plasmids in COS7 cells in various assays. Approximately 30 h after transfection, cells were serum starved (0% FBS) for an additional 16-18 h followed by stimulation with 50 nM EGF or 10 µM LPA. Reactions were stopped using PBS chilled at 4° C., supplemented with 200 μM sodium orthovanadate, and immediately scraped and lysed for immunoprecipitation.

Immunoprecipitation and GST-Pulldown Assays.

These assays were carried out exactly as described previously (2,9). Briefly, cell lysates (~1-2 mg protein) were incubated for 4 h at 4° C. with 2 μg anti-HA mAb (Covance), anti-FLAG mAb (Sigma), 1.6 μg anti-SHP-1 PTP pAb or anti SHP-2 PTP pAb, or 1 μg of their respective pre-immune IgGs followed by incubation with protein G (for all mAbs) or A (for all pAbs) Sepharose beads (GE Healthcare) at 4° C. for an additional 60 min. Beads were washed in PBS-T wash buffer [4.3 mM Na2HPO4, 1.4 mM KH2PO4, pH 7.4, 137 mM NaCl, 2.7 mM KCl, 0.1% (v:v) Tween 20, 10 mM MgCl2, 5 mM EDTA, 2 mM DTT, and 0.5 mM sodium orthovanadate], and bound proteins were eluted by boiling in Laemmli's sample buffer. In vitro binding assays with GST-fused proteins were carried out exactly as previously described (7,9). Buffers were supplemented with 0.5 mM sodium orthovanadate for all steps of the assay.

Immunoblotting.

Protein samples were separated on 10% SDS-PAGE and transferred to PVDF membranes (Millipore, Billerica, Mass.). Membranes were blocked with PBS supplemented with 5% nonfat milk (or with 5% BSA whenever probing for phosphorylated proteins) before incubation with primary Abs Infrared imaging with two-color detection was performed using an Odyssey imaging system (Li-Cor Biosciences, Lincoln, Nebr.). Primary antibodies were diluted as follows: anti-pTyr 1:500, anti-HA 1:1000; anti-SHP-1 1:500, anti-SHP-2 1:500, anti-GIV/Girdin(CTAb) 1:500, anti-GIV ccAb (sera) 1:500, anti-EGFR 1:500, anti-pAkt (5473) 1:250; anti-pERK1/2 1:500, anti-pY1173(EGFR) 1:250, anti-Gαi3 1:300, and anti-FLAG 1:1000. All Odyssey images were processed using Image J software (NIH) and assembled for presentation using Photoshop and Illustrator software (both Adobe).

Statistical Analysis.

Each experiment presented in the figures is representative of at least three independent experiments. Statistical significance between various conditions was assessed with the Wilcoxon Signed-Rank test. Graphical data presented was prepared using GraphPad Software, Inc. (San Diego, Calif.).

Results

Protein Tyrosine Phosphatase SHP-1 Dephosphorylates GIV In Vitro.

Figure 16A:
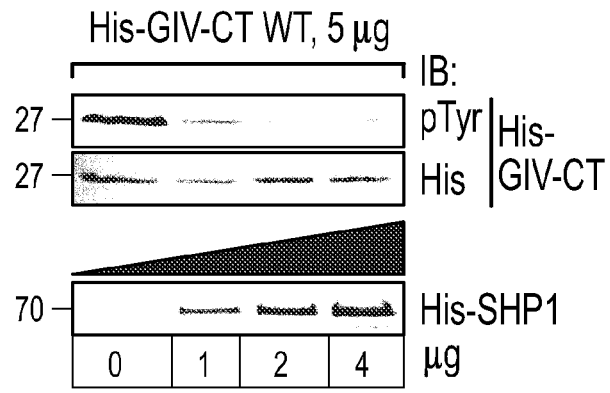
FIG. 16 illustrates that SHP-1 specifically dephosphorylates tyrosine phosphorylated GIV in vitro. (A) His-SHP-1 dephosphorylates tyrosine-phosphorylated His-GIV-CT. His-GIV-CT (1660-1870) was phosphorylated in vitro using recombinant EGFR kinase and was subsequently used as substrate in phosphatase assays using increasing (1, 2, and 4 μg) amounts of recombinant His-SHP-1. Residual tyrosine phosphorylation on His-GIV-CT was assessed by immunoblotting (IB) using phosphotyrosine (pTyr) and His mAbs. His-GIV-CT is efficiently dephosphorylated in the presence of 1 μg, and maximally in the presence of 2 μg His-SHP-1. (B) SHP-1 dephosphorlyates both phosphotyrosines (Y1764 and Y1798) in GIV's C-terminus. His-GIV-CT mutants with one intact tyrosine (Y1764F mutant, in which Y1798 is intact, and Y1798F mutant, in which Y1764 is intact) were phosphorylated in vitro using recombinant EGFR kinase as in 1A. Equal aliquots (5 μg) of these phosphorylated His-GIV-CT mutants were subsequently used in phosphatase assays in the presence (+) or absence (−) of 1 μg His-SHP-1 and analyzed for residual tyrosine phosphorylation by immunoblotting (IB). (C) Wild-type (WT), but not the catalytically inactive (C453S; CS) mutant of SHP-1 dephosphorylates tyrosine-phosphorylated His-GIV-CT in vitro. Equal aliquots of tyrosine phosphorylated His-GIV-CT (phosphorylated using recombinant EGFR kinase as in 1A) were used as substrates in phosphatase assays with indicated amounts of bacterially expressed, purified WT or C453S mutant of GST-SHP-1. Samples were subsequently analyzed for residual tyrosine phosphorylation by immunoblotting (IB). GST-SHP-1 WT efficiently dephosphorylated His-GIV-CT at 1 μg (lane 3) and maximally at 3 μg (lane 4), whereas GST-SHP-1 C453S (CS) failed to dephosphorylate His-GIV-CT at either dose (lanes 5, 6). (D) Wild-type (WT), but not the catalytically inactive C453S (CS) mutant of SHP-1 immunoisolated from COS7 cells dephosphorylates tyrosine-phosphorylated His-GIV-CT in vitro. Tyrosine-phosphorylated His-GIV-CT was generated by carrying out in vitro phosphorylation assays using recombinant EGFR (pY GIV-CT (EGFR); lanes 1-3) or Src (pY GIV-CT (Src); lanes 4-6) kinases. Lysates of COS7 cells transiently expressing WT or CS mutant of HA-SHP-1 were incubated sequentially with anti-HA mAb and protein G agarose beads to immunoisolate active (WT) and catalytically inactive (CS) phosphatase, respectively. In vitro phosphatase assays were subsequently carried out by incubating equal aliquots of pY GIV-CT with the bead-bound SHP-1 WT (lanes 2, 4), SHP-1 CS (lanes 3, 5), or control beads (lane 1). Both EGFR and Src-phosphorylated GIV-CT were efficiently dephosphorylated in the presence of HA-SHP-1 WT (lanes 2, 4), but not HA-SHP-1 CS (lanes 3, 5) or control beads (lane 1). (E, F) COS7 cell lysates immunodepleted of endogenous SHP-1 fail to dephosphorylate tyrosine-phosphorlyated His-GIV-CT in vitro. (E) Lysates of COS7 cells were immunodepleted of SHP-1 (lane 2) or mock-depleted (lane 1) using anti-SHP-1 or preimmune control IgGs, respectively. Equal aliquots of lysates were analyzed for GIV, SHP-1, SHP-2 and actin by immunoblotting (IB). The efficacy of SHP-1 immunodepletion was confirmed as ~>99% by optical densitometry. (F) Equal aliquots of tyrosine-phosphorylated His-GIV-CT (~5 μg) were used as substrates in in-vitro dephosphorylation assays with either buffer alone (lane 5) or equal aliquots (~75 μg) of mock-depleted (lanes 1, 2) or SHP-1-depleted (lanes 3, 4) lysates. Residual phosphorylation was assessed by immunoblotting (IB) for pTyr mAb. Tyrosine-phosphorylated His-GIV-CT is efficiently dephosphorylated in the presence of mock-depleted (lane 2) but not SHP-1-depleted lysate (lane 3). The phosphatase activity of SHP-1-depleted lysate is restored upon addition of bacterially expressed His-SHP-1 (lane 4).

To determine if GIV is a substrate of SHP-1, in vitro phosphatase assays were carried out using bacterially expressed, recombinant His-SHP-1 and tyrosine phosphorylated His-GIV-CT (aa 1660-1870) as substrate. GIV's C-terminus was examined because the only two sites of tyrosine phosphorylation in the entire protein are located within that region (14). To generate the phosphorylated GIV-CT substrate, in vitro kinase assays using His-GIV-CT and recombinant EGFR kinase (Millipore) were carried out as described previously (14). When phosphorylated His-GIV-CT was subsequently incubated with increasing quantities of His-SHP-1, SHP-1 efficiently dephosphorylated GIV in a dose-dependent manner (FIG. 16A) indicating that GIV is a substrate of SHP-1 in vitro.

Figure 16B:
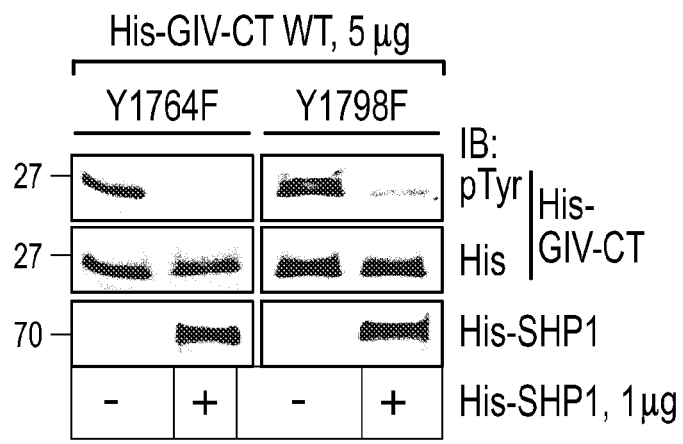

Because GIV is tyrosine phosphorylated at two sites—Y1764 and Y1798 (14), whether SHP-1 selectively dephosphorylates one or both of those phosphotyrosines was assessed. When phosphomutants of His-GIV-CT with either Y1764 or Y1798 mutated to phenylalanine (F) were phosphorylated in vitro by EGFR kinase and subsequently incubated with His-SHP-1, SHP-1 efficiently dephosphorylated both mutants (FIG. 16B). Thus, SHP-1 is capable of dephosphorylating both phosphotyrosines pY1764 and pY1798 in GIV's C-terminus.

To investigate if the catalytic activity of SHP-1 is required to dephosphorylate GIV, in vitro phosphatase assays were carried out using phosphorylated His-GIV-CT and GST-tagged SHP-1 WT or the constitutively inactive mutant in which the cysteine (C) 453 in the catalytic center is replaced with serine (SHP-1 C453S, hereby referred to as CS). The CS mutation selectively abolishes PTP activity while retaining the ability of SHP-1 to bind substrate proteins (24). SHP-1 WT, but not SHP-1 CS dephosphorylated tyrosine-phosphorylated His-GIV-CT in a dose-dependent manner (FIG. 16C). Identical results were obtained when SHP-1-HA immunoisolated from COS7 cells was used to dephosphorylate EGFR- or Src-phosphorylated His-GIV-CT in vitro (FIG. 16D). These results demonstrate that an intact catalytic domain is indeed required for the protein tyrosine phosphatase SHP-1 to dephosphorylate GIV-CT in vitro.

Figure 16F:
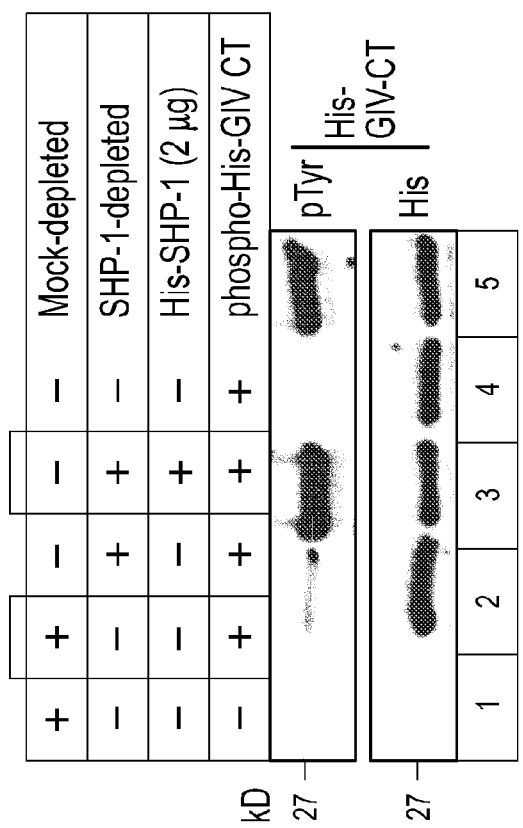

Next whether other tyrosine phosphatases, besides SHP-1 can dephosphorylate GIV was assessed. To this end, mock-depleted and SHP-1-depleted COS7 lysates were prepared (FIG. 16E) and used as sources of phosphatases in in vitro phosphatase assays with tyrosine-phosphorylated His-GIV-CT. While mock-depleted lysates efficiently dephosphorylated tyrosine-phosphorylated GIV-CT, lysates immunodepleted of SHP-1 (by >99%) failed to do so (FIG. 16F). Furthermore, addition of recombinant His-SHP-1 to SHP-1-depleted lysates restored the ability of this lysate to dephosphorylate tyrosine-phosphorylated GIV-CT (FIG. 16F). Thus, the key catalytic activity which is required for removal of GIV's phosphotyrosines was lost with depletion of SHP-1, and restored by adding back recombinant SHP-1. These results indicate that SHP-1 is the major cellular phosphatase that dephosphorylates GIV's tyrosines in vitro. Of note, SHP-2, the closest relative of SHP-1 was abundant in both mock- and SHP-1-depleted cytosols (FIG. 16E), but failed to dephosphorylate GIV-CT (FIG. 16F), highlighting the specificity of SHP-1 towards GIV-CT as its substrate.

SHP-1 Inhibits Tyrosine Phosphorylation of GIV after Activation of EGF Receptor or Src Kinases.

Figure 17A:
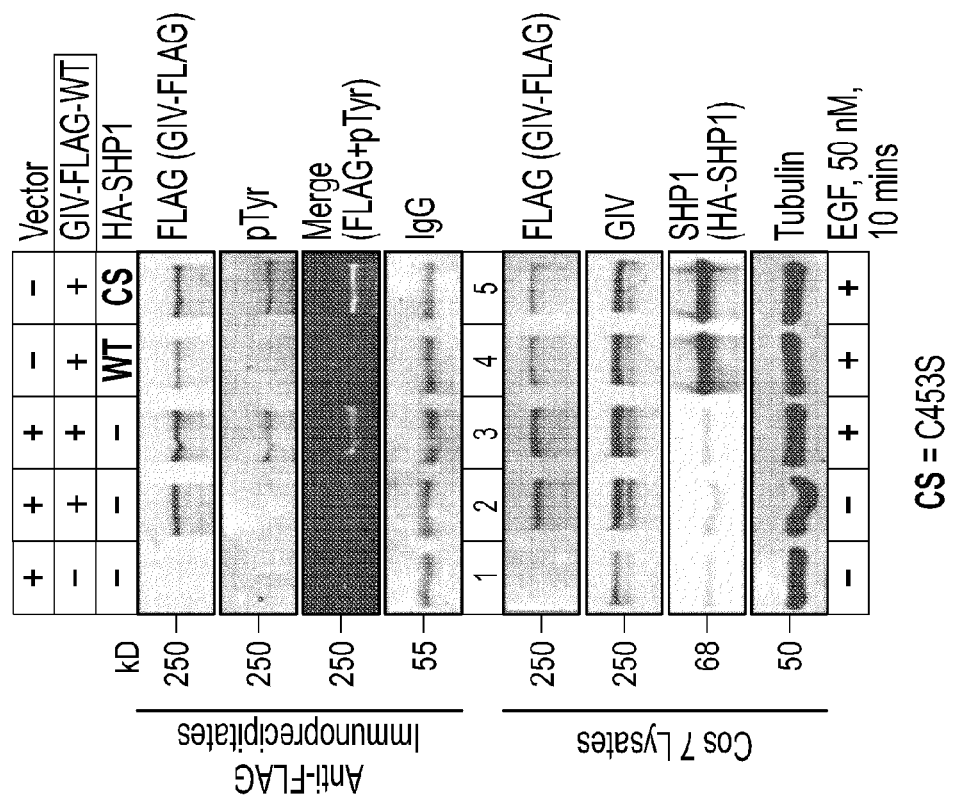
FIG. 17 illustrates that SHP-1 inhibits tyrosine phosphorylation of GIV by EGFR and Src. (A) Wild-type (WT), but not the catalytically inactive C453S (CS) mutant of SHP-1 dephosphorylates GIV after EGF stimulation. COS7 cells transfected with vector alone (lane 1), GIV-FLAG alone (lanes 2, 3), or GIV-FLAG and HA-SHP-1 WT (lane 4), or GIV-FLAG and HA-SHP-1 CS mutant (lane 5) were serum starved (−) and subsequently stimulated with EGF (50 nM, +) for 10 min. Equal aliquots of lysates (bottom) were incubated sequentially with anti-FLAG mAb and protein G agarose beads Immune complexes (top) were analyzed by two-color immunoblotting (IB) for GIV and pTyr using the Li-COR Odyssey Infrared Western Blot Imaging System. Single channel images for GIV and pTyr are displayed in grayscale which show that immunoprecipitated GIV is phosphorylated on tyrosine(s) exclusively after EGFR stimulation (compare lanes 2 and 3). Yellow pixels in the overlay of GIV (red) and pTyr (green) images (Merge panels) confirm that GIV was phosphorylated on tyrosine(s) after EGF treatment. EGF-dependent tyrosine phosphorylation of GIV was undetectable in cells co-transfected with HA-SHP-1 WT (lane 4), but robust in those expressing HA-SHP-1 CS (lane 5). Expression of GIV and SHP-1 in all lysates was analyzed by immunoblotting (IB) for FLAG, GIV, SHP-1 and tubulin (bottom). (B) Wild-type (WT), but not the catalytically inactive C453S (CS) mutant of SHP-1 dephosphorylates Src-phosphorylated GIV. COS7 cells were transfected with vector alone (lane 1), or GIV-FLAG alone (lane 2), or GIV-FLAG and Src-HA K295R inactive mutant (In, lane 3), or GIV-FLAG and Src-HA Y527F active mutant (Ac, lanes 4-6). HA-SHP-1 WT and HA-SHP-1 CS were co-transfected with active Src Y527F in lanes 5 and 6, respectively. Equal aliquots of lysates (bottom) were incubated with anti-FLAG mAb and protein G agarose beads Immune complexes (top) were analyzed by immunoblotting (IB) for GIV and pTyr as in 2A. Tyrosine phosphorylation was detectable in GIV-FLAG immunoprecipitated from cells co-expressing the active Src-HA mutant (lane 4, pTyr panel), but not from cells expressing vector (lane 1), or GIV-FLAG alone (lane 2), or those expressing the inactive Src-HA mutant (lane 3). Src-induced tyrosine phosphorylation of GIV-FLAG was undetectable in cells co-expressing HA-SHP-1 WT (lane 5), but restored in cells co-expressing HA-SHP-1 CS (lane 6). Expression of GIV, Src and SHP-1 in all lysates was analyzed by immunoblotting (IB) for FLAG, GIV, HA (Src) and tubulin (bottom). (C) EGF-dependent tyrosine-phosphorylation of GIV is enhanced in cells depleted of endogenous SHP-1. HeLa cells treated with scrambled (Scr) or SHP-1 siRNA were serum starved (0 min) followed by stimulation with 50 nM EGF for 5 and 15 min. Equal aliquots of lysates (left) were incubated sequentially with anti-GIV (CTAb) and protein A agarose beads Immune complexes (right) were analyzed for GIV and pTyr by immunoblotting (IB). Tyrosine-phosphorylated GIV (pTyr) was undetectable in starved cells (lane 2), peaked at 5 min after EGF stimulation in both scrambled and SHP-1 siRNA-treated cells (lanes 3, 5), and decreased at 15 min (lanes 4, 6). Phosphorylation of GIV in the immunoprecipitates (right panel) is increased in SHP-1-depleted cells as compared to control by ~4.2 fold at 5 min (compare lanes 3 and 5) and by ~1.5 fold at 15 min (compare lanes 4 and 6). Activation of EGFR and depletion of SHP-1 (by ~70%) were confirmed by analyzing equal aliquots of lysates for GIV, total EGFR (tEGFR), phosphotyrosine 1173 EGFR (pYEGFR), SHP-1, Gαi3 and tubulin by immunoblotting (IB).

Both receptor (EGFR and InsulinR) and non-receptor (c-Src) tyrosine kinases can phosphorylate GIV's C-terminal tyrosines in vivo (14). To determine if SHP-1 can inhibit EGFR- or Src-induced tyrosine phosphorylation of GIV in cells, in vivo phosphorylation assays were carried out (14). GIV was immunoprecipitated from COS7 cells co-transfected with GIV-FLAG and HA-SHP-1, and the extent of tyrosine phosphorylation on GIV was assessed. Co-expression of SHP-1 virtually abolished the EGF-triggered tyrosine phosphorylation (FIG. 24). When the in vivo phosphorylation assay was performed in cells co-transfected with either HA-SHP-1-WT or HA-SHP-1-CS mutant, WT, but not the CS mutant was found to virtually abolished the EGF-triggered tyrosine-phosphorylation (FIG. 17A), thus confirming that the catalytic activity of SHP-1 is required for downregulation of tyrosine-phosphorylated GIV after EGF stimulation. Thus SHP-1 dephosphorylates tyrosine-phosphorylated GIV downstream of EGFR.

Figures 17B, 17C:
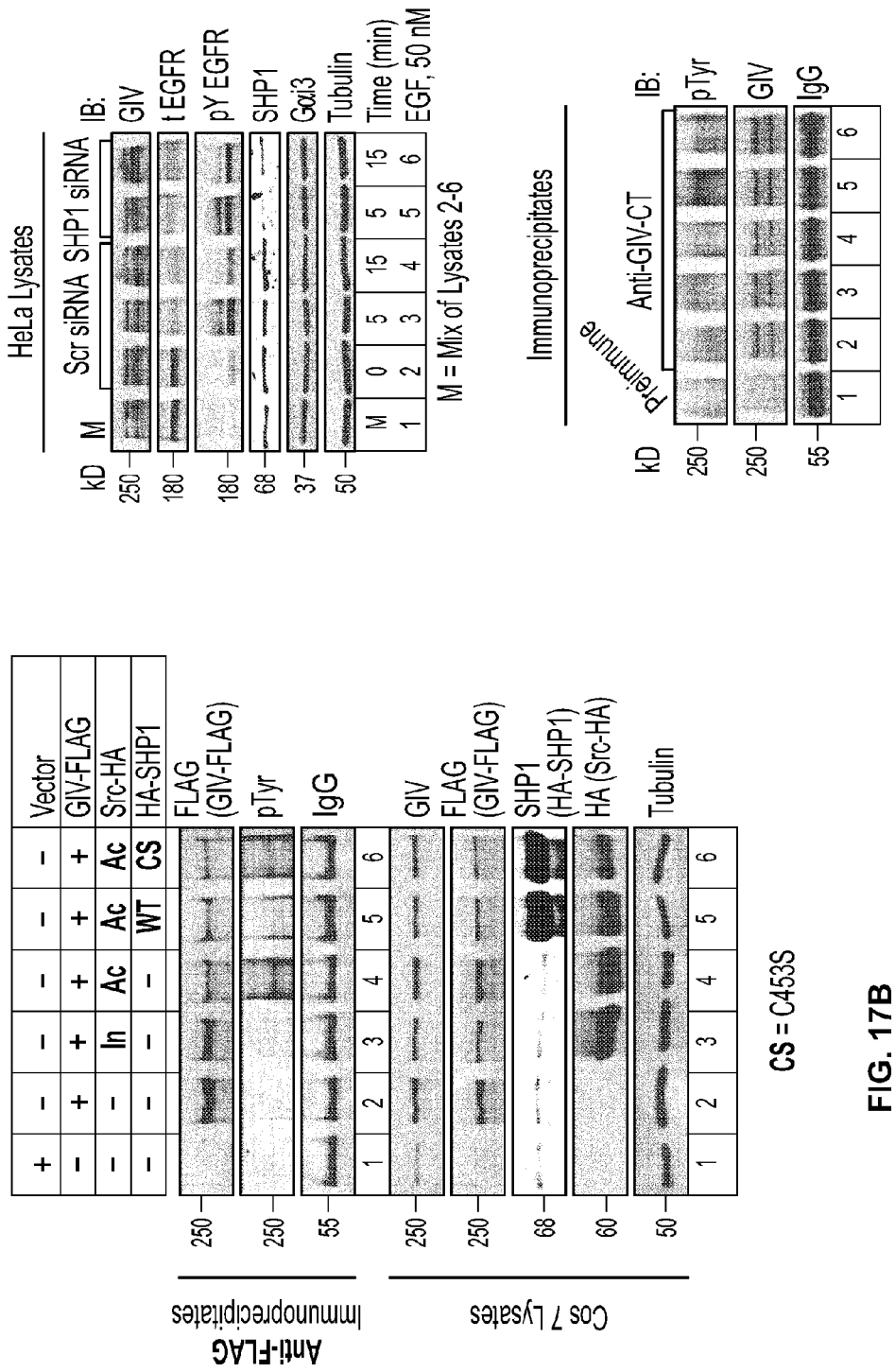

To discern if SHP-1 can also dephosphorylate GIV after activation of non-RTKs like Src, GIV was immunoprecipitated from COS7 cells co-expressing GIV-FLAG with constitutively active (Y527F (25)) or inactive (K295R (26)) mutants of Src-HA and the WT or the inactive CS mutant of HA-SHP-1. As shown previously by the inventors (14), GIV was tyrosine phosphorylated in a Src-activity dependent manner: co-transfection of GIV with active, but not inactive Src mutant resulted in increased tyrosine phosphorylation of GIV (FIG. 17B). Co-expression of SHP-1 WT, but not SHP-1 CS abolished Src-dependent tyrosine phosphorylation of GIV (FIG. 16B), demonstrating that the catalytic activity of SHP-1 is required for downregulation of Src-phosphorylated GIV. Therefore, SHP-1 antagonizes the action of Src kinase by dephosphorylating GIV once it is phosphorylated by Src.

To investigate how SHP-1 affects the timing and extent of tyrosine phosphorylation of endogenous GIV, HeLa cells were depleted of endogenous SHP-1 using target-specific or control siRNA, and subsequently immunoprecipitated GIV and assessed the extent of tyrosine phosphorylation at 5 or 15 min after EGF stimulation. In control siRNA-treated cells, tyrosine phosphorylation of GIV occurred exclusively after ligand stimulation, reached peak levels at 5 min, and was downregulated at 15 min (FIG. 17C). In cells depleted of SHP-1 (by ~70%), although the timing of phospho-dephosphorylation of GIV remained the same, the extent of peak phosphorylation was enhanced by ~4.2 fold at 5 min, and ~1.5 fold at 15 min compared to controls. Of note, levels of total EGFR, the peak extent of receptor autophosphorylation (pY EGFR), and the rate of receptor degradation were almost similar in both control and SHP-1-depleted cells at 5 min, and only slightly increased in SHP-1-depleted cells at 15 min, indicating that the tyrosine kinase activity of EGFR was similar under these conditions. This indicates that the observed increase in the abundance of tyrosine-phosphorylated GIV in cells depleted of SHP-1 at 5 min is unlikely to be due to hyperphosphorylation by EGFR, and instead a consequence of impaired dephosphorylation of GIV by SHP-1. Taken together, these results demonstrate that SHP-1 can dephosphorylate GIV in vivo after activation of both RTKs and non-RTKs.

SHP-1 Inhibits Tyrosine Phosphorylation of GIV Downstream of G Protein Coupled Receptors.

Figure 18:
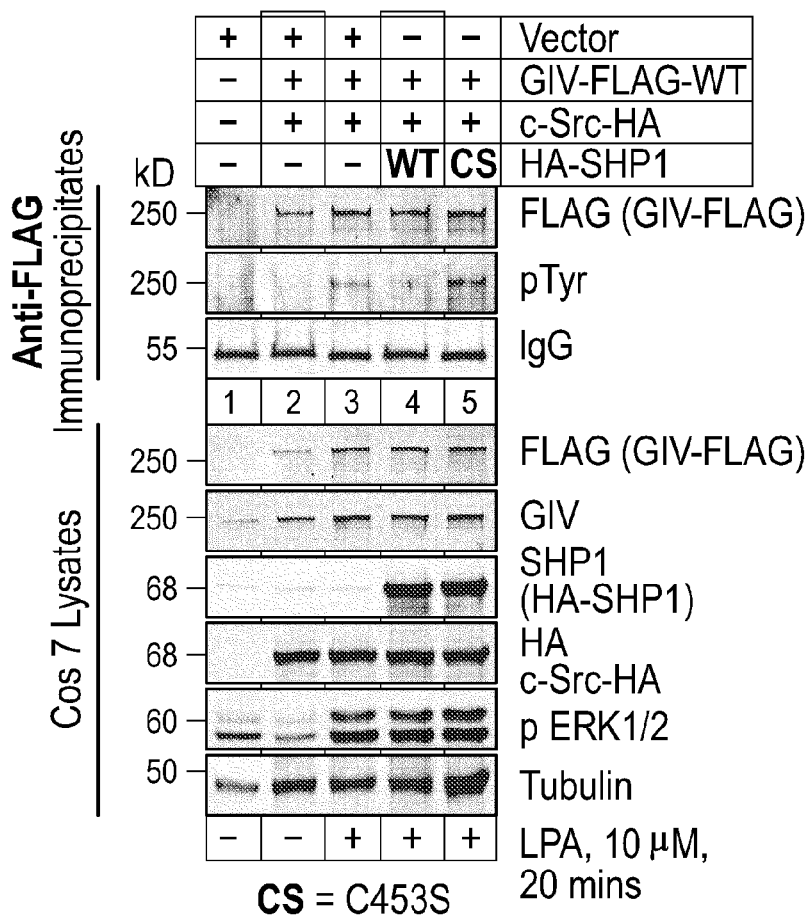
FIG. 18 illustrates that wild-type (WT), but not the catalytically inactive SHP-1C453S (CS) mutant inhibits tyrosine phosphorylation of GIV upon activation of LPAR. COS7 cells transfected with vector alone (lane 1), GIV-FLAG alone (lanes 2, 3), or GIV-FLAG and HA-SHP-1 WT (lane 4), or GIV-FLAG and HA-SHP-1 CS mutant (lane 5) were serum starved (−) and subsequently stimulated with LPA (10 μM, +) for 20 min. Equal aliquots of lysates (bottom) were incubated with anti-FLAG mAb and protein G agarose beads. Immune complexes (top) were analyzed for GIV and pTyr by immunoblotting (IB). Immunoprecipitated GIV was phosphorylated on tyrosine(s) exclusively after LPAR stimulation (compare lanes 2 and 3). LPA-dependent tyrosine phosphorylation of GIV was markedly reduced in cells co-transfected with HA-SHP-1 WT (lane 4), but robust in those expressing HA-SHP-1 CS (lane 5). Adequate stimulation of cells by LPA and expression of GIV, Src, and SHP-1 in all lysates was analyzed by immunoblotting (IB) for FLAG, GIV, SHP-1, HA (Src), phospho-ERK1/2 and tubulin (bottom).

Because activation of GPCRs is known to trigger tyrosine phosphorylation of GIV (via Src kinase) (14) and to activate SHP-1 (via Gαq) (27), whether SHP-1 can downregulate tyrosine-phosphorylation of GIV was assessed after activation of lysophosphatidic acid (LPA) receptor (a member of the GPCR family). Activation of LPA receptor triggered tyrosine phosphorylation of GIV (FIG. 25, FIG. 18). This LPA-triggered tyrosine phosphorylation was inhibited in cells co-expressing SHP-1 WT, but maintained in those co-expressing the inactive SHP-1 CS mutant (FIG. 18), indicating that the catalytic activity of SHP-1 is required for downregulation of tyrosine-phosphorylated GIV after LPA stimulation. Thus, SHP-1 also dephosphorylates GIV downstream of GPCRs.

SHP-1 Interacts Directly and Constitutively with GIV.

Figure 19A:
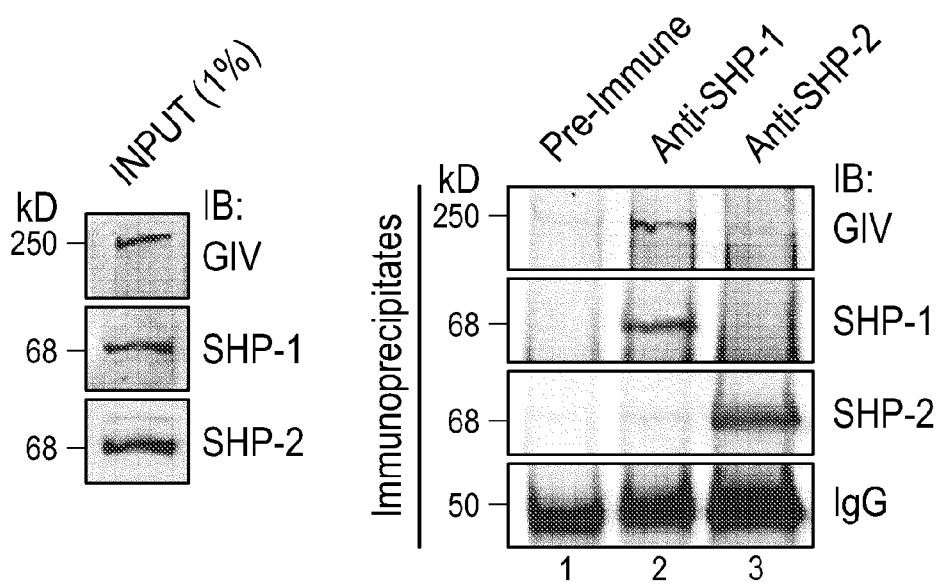
FIG. 19 shows that SHP-1 interacts with GIV in vivo. (A) GIV co-immunoprecipitates with SHP-1, but not SHP-2. Equal aliquots of COS7 lysates (left) were incubated with either rabbit preimmune (lane 1), or anti-SHP-1 (lane 2), or anti-SHP-2 (lane 3) IgGs and protein A agarose beads Immune complexes (25) were analyzed for GIV, SHP-1 and SHP-2 by immunoblotting. SHP-1 and SHP-2 were immunoprecipitated efficiently and specifically. GIV co-immunoprecipitated with SHP-1 (lane 2) but not SHP-2 (lane 3) or control IgG (lane 1). (B) GIV, but not Gαi3 interacts constitutively with SHP-1. COS7 cells were serum starved (−) and subsequently stimulated with 50 nM EGF for 10 min (+). Equal aliquots of lysates (bottom) were incubated with either rabbit preimmune (lane 1), or anti-SHP-1 (lanes 2, 3) IgGs and protein A agarose beads Immune complexes (top) were analyzed for GIV, SHP-1 and Gαi3 by immunoblotting (IB). SHP-1 was immunoprecipitated efficiently and specifically. GIV, but not Gαi3 co-immunoprecipitated with SHP-1 from both starved and EGF-stimulated cells (lanes 2, 3). (C) GIV's GEF motif is not required for the GIV-SHP-1 interaction. COS7 cells were transfected with vector alone (lane 1), or FLAG-tagged wild-type GIV (GIV-WT; lane 2), or the GEF-deficient F1685A (FA) mutant (GIV-FA; lane 3). Equal aliquots of lysates (bottom) were incubated with anti-SHP-1 IgGs and protein A agarose beads Immune complexes were analyzed for FLAG (GIV-FLAG) and SHP-1 by immunoblotting.

Most PTPs interact with their substrates prior to catalyzing the removal of phosphates on target tyrosines (28,29). To investigate whether endogenous SHP-1 and GIV interact in vivo, SHP-1 was immunoprecipitated from COS7 (FIG. 19A) or HEK (FIG. 26) cells and immunoblotted for GIV. GIV co-immunoprecipitated with SHP-1 in both cell lines, indicating that they interact at steady-state in vivo. Of note, this GIV-SHP-1 interaction is specific because GIV did not co-immunoprecipitate with the closely-related family member, SHP-2 (FIG. 19A). To assess if the GIV-SHP-1 interaction is ligand-dependent, SHP-1 was immunoprecipitated from serum-starved or EGF-stimulated COS7 cells, and the immune complexes were for analyzed for GIV. The ratio of GIV:SHP-1 in immune complexes remain unchanged before and after EGF stimulation, indicating that the interaction occurs constitutively, i.e., independent of receptor activation. The abundance of GIV-SHP-1 interaction also remained unchanged regardless of the activation status of Src. In contrast to GIV, Gαi3 did not interact with SHP-1 in either COS7 or HEK cell lines (FIG. 19B, 26). To determine if the GEF motif of GIV, via which GIV activates Gαi subunits (1-3) (7), is required for the GIV-SHP-1 interaction, SHP-1 was immunoprecipitated SHP-1 from COS7 cells expressing WT or the GEF-deficient F1685A (FA) mutant of GIV-FLAG, and the immune complexes were analyzed for GIV-FLAG. The relative abundance of GIV:SHP-1 complexes was similar between GIV-FA and GIV-WT (FIG. 19C), demonstrating that GIV's GEF motif and GIV-dependent activation of Gαi, are not required for GIV to interact with SHP-1 in cells. Taken together, GIV, but not Gαi3 interacts specifically with SHP-1 (and not SHP-2) in mammalian cells, and this interaction occurs constitutively; i.e., independent of both receptor and G protein activation.

Figure 20A:
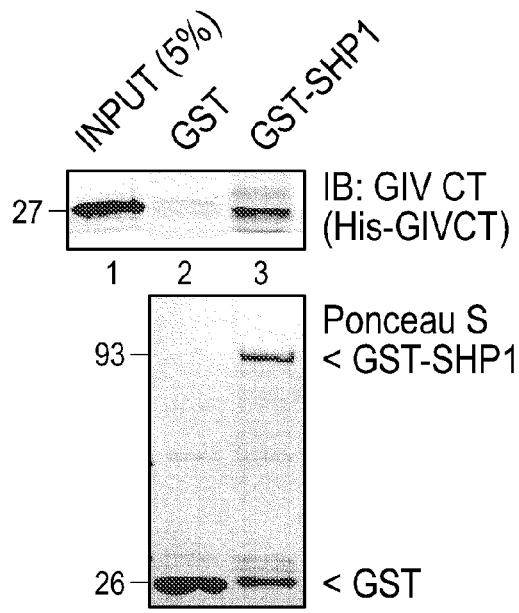
FIG. 20 shows that the C-terminus of GIV directly binds to SHP-1. (A) His-GIV-CT (aa 1660-1870) directly binds GST-SHP-1. Equal aliquots (~3 μg) of His-GIV-CT were incubated with ~30 ug of GST and ~25 μg GST-SHP-1 immobilized on glutathione beads. Bound His-GIV-CT was analyzed by immunoblotting (IB) with GIV-CT pAb. Relative amounts of bead-bound GST and GST-SHP-1 were confirmed by ponceau S staining. (B) His-GIV-CT preferentially binds the C-terminal SH2 domain of SHP-1. Equal aliquots (~3 μg) of His-GIV-CT were incubated with ~30 μg GST, wild-type GST-SHP-1, GST-SHP-1 lacking both SH2 domains (ΔN+CSH2), and GST-SHP-1 lacking only the N-terminal SH2 domain (ΔNSH2). Bound His-GIV-CT was analyzed by immunoblotting (IB) with GIV-CT pAb. His-GIV-CT specifically bound wild-type GST-SHP-1, but not GST alone (lanes 3, 4); binding was reduced in the absence of both SH2 domains (lane 5), but restored when the C-terminal SH2 domain was present (lane 6).
Figure 20B:
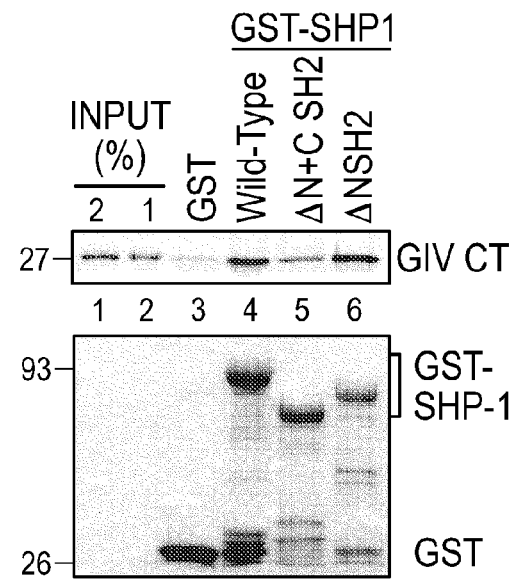

To determine if the GIV-SHP-1 interaction observed in vivo is direct, in vitro binding assays were carried out using recombinant His-GIV-CT and GST or GST-SHP-1 immobilized on glutathione beads. GST-SHP-1, but not GST alone bound His-GIV-CT (FIG. 20A), indicating that SHP-1 directly binds GIV and that the C-terminus of GIV is sufficient to mediate such an interaction. Because SHP-1 is recruited to its substrates by one or both of its in-tandem SH2 domains (30), whether the SH2 domains, and if so, which one (NSH2 or CSH2) is responsible for mediating the direct interaction of SHP-1 with GIV's C-terminus was assessed. For this, GST-tagged truncated versions of SHP-1 were generated lacking either both SH2 domains (ΔN+C SH2) or just the NSH2 domain (ΔNSH2, in which the CSH2 is intact). The truncated versions were used alongside GST-SHP-1 (full length) in binding assays. When these GST-SHP-1 proteins were immobilized on glutathione beads and incubated with His-GIV-CT, GIV-CT bound equally to full length SHP-1 and to SHP-1 ΔNSH2, whereas binding to SHP-1 ΔN+CSH2 was dramatically reduced by ~80% (FIG. 20B), indicating that the NSH2 domain is not required for SHP-1 to bind GIV, but the CSH2 domain is, and that the CSH2 domain can account for the observed interaction between GIV-CT and SHP-1 in vitro. Thus, the second (CSH2), but not the first (NSH2) of the two in-tandem SH2 domains of SHP-1 directly binds GIV's C-terminus. Noteworthy, the observed interaction between GST-SHP-1 and His-GIV-CT was not affected by tyrosine phosphorylation of GIV-CT. Taken together with the findings by co-immunoprecipitation assays on cell lysates (FIG. 19), the GIV-SHP-1 interaction was determined to be direct and constitutive.

SHP-1 Attenuates GIV-Dependent Enhancement of PI3K-Akt Signals by Dephosphorylating Tyrosine-Phosphorylated GIV and Inhibiting the Assembly of phosphoGIV-p85α (PI3K) Complexes.

Figure 21:
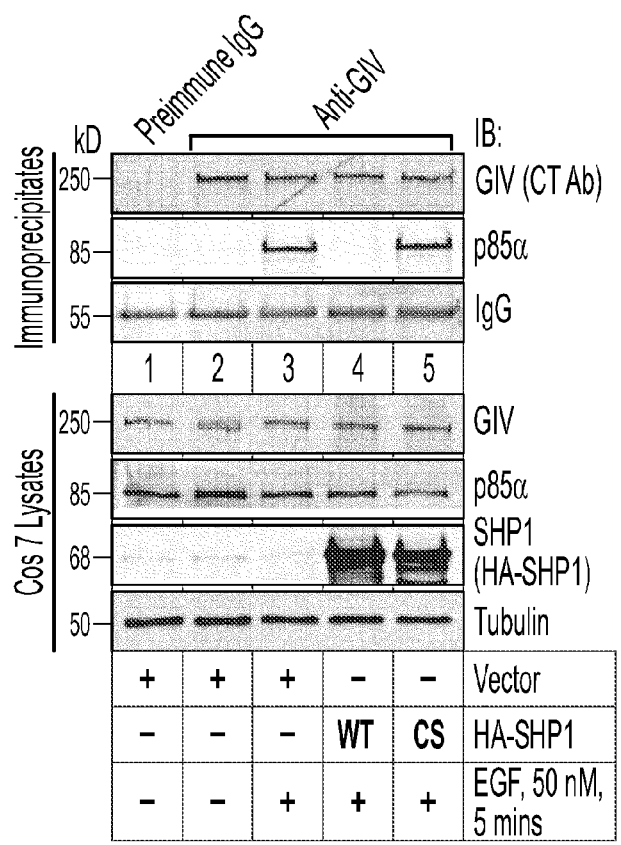
FIG. 21 shows that wild-type (WT) but not the catalytically inactive C453S (CS) mutant of SHP-1 inhibits the formation of GIV-p85α(PI3K) complexes after EGF stimulation. COS7 cells transfected with vector alone (lanes 1-3), HA-SHP-1 WT (lane 4), or HA-SHP-1 CS mutant (lane 5)

As described in Example 1, tyrosine-phosphorylated GIV directly binds the p85α-regulatory subunit of PI3K, activates Class 1 PI3K, enhances the generation of second messenger PIP3 at the PM, and triggers the subsequent recruitment and activation of Akt kinase. Because SHP-1 dephosphorylates tyrosine-phosphorylated GIV, SHP-1 was predicted to inhibit the ligand-dependent assembly of GIV-PI3K complexes in cells. This was determined to be the case, because EGF-induced formation of complexes between p85α(PI3K) and endogenous GIV (FIG. 21) or FLAG-tagged GIV (FIG. 26) in COS7 cells was inhibited in the presence of WT, but not the inactive CS mutant of HA-SHP-1. Of note, the failure to assemble GIV-p85α(PI3K) complexes in cells expressing SHP-1 WT coincided with a dramatic suppression of tyrosine-phosphorylated GIV to virtually undetectable levels. These findings indicate that the catalytic activity is required for SHP-1 to simultaneously dephosphorylate tyrosine-phosphorylated GIV and to inhibit the formation of phosphoGIV-p85α complexes. These results indicate that the catalytic activity of SHP-1 is required to dephosphorylate GIV's phosphotyrosines and thereby, inhibit the formation of phosphoGIV-p85α complexes.

To determine if SHP-1 affects GIV's function as an enhancer of Akt signaling, COS7 cells were co-transfected with GIV-FLAG and either SHP-1-WT or SHP-1-CS mutant, and maintained in 2% FBS prior to lysis. Consistent with the previously established role of GIV as an enhancer of Akt phosphorylation (Example 1), overexpression of GIV-FLAG alone was found to enhance Akt activity by ~2.5 fold, as determined by the extent of Akt phosphorylation at S473 (FIG. 22A, B). Co-expression of WT, but not the inactive CS mutant of SHP-1 returned Akt activity to levels seen in control cells without GIV-FLAG (FIG. 22A, B), indicating that a catalytically active SHP-1 is required to inhibit GIV from enhancing the phosphorylation and subsequent activation of Akt kinase. Furthermore, depletion of endogenous SHP-1 from HeLa cells by siRNA was associated with enhanced Akt phosphorylation at both 5 and 15 min after EGF stimulation (FIG. 22C), temporally coinciding with the enhanced phosphorylation of GIV observed in these cells at those time points (FIG. 17C). Of note, the peak phosphorylation of ERK1/2 in SHP-1-depleted cells was similar to controls, indicating that the observed effect of SHP-1 on Akt signaling is pathway-specific. Based on these findings SHP-1 was determined to antagonize/attenuate GIV-dependent enhancement of Akt signaling, and that enhancement of Akt activity in the absence of SHP-1 was mediated at least in part due to a failure to downregulate tyrosine phosphorylated GIV and the phosphoGIV-PI3K-AKt signaling cascade.

In summary (FIG. 23), SHP-1 is the major cellular phosphatase that downregulates tyrosine-phosphorylated GIV downstream of both growth factor RTKs and GPCRs and attenuates the previously characterized (Example 1) prometastatic phosphoGIV-PI3K-Akt axis of signaling.

REFERENCES

1. Enomoto et al., (2005) Developmental Cell 9(3), 389-402; 2. Ghosh et al., (2010) Mol Biol Cell 21(13), 2338-2354; 3. Jiang et al., (2008) Cancer Research 68(5), 1310-1318; 4. Kitamura et al., (2008) Nature Cell Biology 10(3), 329-337; 5. Anai et al., (2005) J Biol Chem 280(18), 18525-18535; 6. Garcia-Marcos et al., Mol Biol Cell 22(5), 673-686; 7. Garcia-Marcos et al., (2009) Proc Natl Acad Sci USA 106(9), 3178-3183; 8. Ghosh et al., (2008) J Cell Biol 182(2), 381-393; 9. Garcia-Marcos et al., (2010) J Biol Chem 285(17), 12765-12777; 10. Enomoto et al., (2009) Neuron 63(6), 774-787; 11. Enomoto et al (2006) Annals NY Acad Sci 1086, 169-184; 12. Garcia-Marcos et al., FASEB J 25(2), 590-599; 13. Ghosh et al., (2011) Cell Adh Migr 5(3), 237-248; 14. Lin et al. (2011) In press, Science Signaling (STKE); 15. Larsen et al., (2003) Nature Reviews 4(9), 700-711; 16. Cuevas et al., (1999) J Biol Chem 274(39), 27583-27589; 17. Yu et al., (1998) J Biol Chem 273(6), 3687-3694; 18. Lu et al., (2003) J Biol Chem 278(41), 40057-40066; 19. Keilhack et al., (1998) J Biol Chem 273(38), 24839-24846; 20. Tenev et al., (1997) J Biol Chem 272(9), 5966-5973; 21. Le-Niculescu et al., (2005) J Biol Chem 280(23), 22012-22020; 22. Bairstow et al., (2005) J Biol Chem 280(25), 23884-23891; 23. Fawcett and Lorenz, (2005) J Immunol 174(5), 2849-2859; 24. Mizuno et al., (2000) J Immunol 165(3), 1344-1351; 25. Cooper et al., (1986) Science 231(4744), 1431-1434; 26. Kamps and Sefton, (1986) Mol Cell Biol 6(3), 751-757; 27. Ngai et al., (2009) BMC immunology 10, 27; 28. Blanchetot et al., (2005) Methods 35(1), 44-53; 29. Cote et al., (1998) Biochemistry 37(38), 13128-13137; 30. Pei et al., (1996) Proc Natl Acad Sci USA 93(3), 1141-1145; 31. Yaffe, (2002) Nature Reviews 3(3), 177-186; 32. Jones et al., (2004) J Biol Chem 279(39), 40475-40483; 33. Feng et al., (2002) Proc Natl Acad Sci USA 99(19), 12049-12054; 34. Berg et al., (1999) J Biol Chem 274(50), 35855-35865; 35. Jiao et al., (1996) Mol Cell Biol 16(12), 6985-6992; 36. Mizuno et al., (1996) J Exp Med 184(2), 457-463; 37. Yoshida et al., (1999) J Biol Chem 274(49), 34663-34668; 38. Pei et al., (1994) Biochemistry 33(51), 15483-15493; 39. Kharbanda et al., (1996) Proc Natl Acad Sci USA 93(14), 6898-6901; 40. Burshtyn et al., (1999) J Immunol 162(2), 897-902; 41. Dubois et al., (2006) Nature Medicine 12(5), 549-556; 42. Sugano et al., (2005) FASEB J 19(14), 2054-2056; 43. Cui et al., (2002) Molecular Endocrinology 16(9), 2113-2123; 44. Krotz et al., (2005) Journal of the American College of Cardiology 45(10), 1700-1706; 45. Christophi and Massa, (2009) Viral Immunology 22(6), 371-387; 46. Fortin et al., (2006) J Leukocyte Biol 79(5), 1061-1072; 47. Kruger et al., (2000) J Immunol 165(10), 5847-5859; 48. Kim et al., (1999) J Exp Med 190(5), 681-690; 49. Hakak et al., (2000) Oncogene 19(28), 3164-3171; 50. Ivins Zito et al., (2004) J Cell Physiol 199(2), 227-236; 51. Wadley et al., (2007) J Appl Physiol 102(4), 1624-1631; 52. Bard-Chapeau et al., (2006) Mol Cell Biol 26(12), 4664-4674; 53. Burks and Agazie, (2006) Oncogene 25(54), 7166-7179; 54. Laramee et al., (2007) J Biol Chem 282(11), 7758-7769; 55. Banville et al., (1995) Genomics 27(1), 165-173; 56. Garcia-Marcos et al., (2011) FASEB J, 25(2), 590-599; 57. Witkiewicz et al., (2007) Human Pathology 38(3), 462-467; 58. Benali et al., (2000) Proc Natl Acad Sci USA 97(16), 9180-9185; 59. Seo et al., (2006) J Biol Chem 281(6), 3711-3721; 60. Koyama et al., (2003) Lab Invest 83(12), 1849-1858; 61. Tassidis et al., (2010) Int J Cancer 126(10), 2296-2307; 62. Tassidis et al., (2010) Prostate 70(14), 1491-1500; 63. Bradshaw and Porteous, (2010) Neuropharmacology; 64. Porteous and Millar, (2009) Neuron 63(6), 711-713; 65. Miyake et al., (2011) Circulation Research 108(10), 1170-1179; and 66. Frank et al., (2004) J Biol Chem 279(12), 11375-11383.

I claim:

1. A method for assessing risk of metastasis of a solid tumor, the method comprising:
    a) subjecting a sample from the solid tumor to a procedure for quantitation of tyrosine phosphorylation of one or both of pY1764 and pY1798 of human Galpha-interacting protein (GIV), wherein the procedure for the quantitation of tyrosine phosphorylation of GIV comprises an antibody-based assay for measurement of an anti-phosphotyrosine antibody binding specifically to the phosphorylated amino acid sequence of SEQ ID NO:5 (pYFISS) of GIV or the phosphorylated amino acid sequence of SEQ ID NO:6 (pYATLP) of GIV;
    b) detecting an elevated level of tyrosine phosphorylation of GIV in the sample as compared to a control sample; and
    c) determining the subject has metastasis or increased risk of metastasis when the elevated level of tyrosine phosphorylation of GIV is detected.

2. The method of claim 1, wherein the solid tumor is a carcinoma.

3. The method of claim 2, wherein the carcinoma is breast carcinoma.

4. The method of claim 1, wherein the elevated level of tyrosine phosphorylation is further associated with a poor prognosis for disease outcome.

5. The method of claim 1, wherein the anti-phosphotyrosine antibody specifically binds to the phosphorylated amino acid sequence of SEQ ID NO:5 (pYFISS).

6. The method of claim 1, wherein the anti-phosphotyrosine antibody specifically binds to the phosphorylated amino acid sequence of SEQ ID NO:6 (pYATLP).

7. The method of claim 1, wherein the antibody-based assay is selected from the group consisting of immunofluorescence analysis, flow cytometry, immunohistochemistry, immunocytochemistry, antibody microarray, enzyme-linked immunosorbent assay (ELISA), and Western blotting.

8. The method of claim 1, wherein the procedure for the quantitation of tyrosine phosphorylation of GIV comprises the step of contacting the sample with a protein comprising an SH2 domain of p85alpha(PI3K).

9. An isolated antibody that binds specifically to a polypeptide comprising the phosphorylated amino acid sequence of SEQ ID NO:5 (pYFISS) or the phosphorylated amino acid sequence of SEQ ID NO:6 (pYATLP).

10. The isolated antibody of claim 9, wherein the antibody specifically binds to the polypeptide comprising the phosphorylated amino acid sequence of SEQ ID NO:5 (pYFISS).

11. The isolated antibody of claim 9, wherein the antibody specifically binds to the polypeptide comprising the phosphorylated amino acid sequence of SEQ ID NO:6 (pYATLP).

12. The isolated antibody of claim 9, wherein the polypeptide is human Galpha-interacting protein (GIV).

13. The isolated antibody of claim 9, wherein the antibody is a monoclonal antibody.

14. The isolated antibody of claim 9, wherein the antibody is a polyclonal antibody.

15. The isolated antibody of claim 9, wherein the antibody is an antibody fragment.

16. The isolated antibody of claim 15, wherein the antibody fragment is an Fab, F(ab')2, Fv or Sfv fragment.

17. The isolated antibody of claim 9, wherein the antibody is coupled to a detectable marker.

18. The isolated antibody of claim 17, wherein the detectable marker is one of the group consisting of a radioisotope, a metal chelator, an enzyme, a fluorescent compound, a bioluminescent compound, and a chemiluminescent compound.

* * * * *